United States Patent
Brennan et al.

(10) Patent No.: US 10,987,183 B2
(45) Date of Patent: Apr. 27, 2021

(54) OPHTHALMIC SURGICAL SYSTEMS, METHODS, AND DEVICES

(71) Applicant: Alcon Pharmaceuticals Ltd., Fribourg (CH)

(72) Inventors: Jeffrey David Brennan, Los Angeles, CA (US); Mark Humayun, Glendale, CA (US)

(73) Assignee: Alcon Inc., Rue Louis-d'affry ( * ) Notice: Subject to any disclaimer, the term of this patent is extended or adjusted under 35 U.S.C. 154(b) by 226 days.

(21) Appl. No.: 15/970,349

(22) Filed: May 3, 2018

(65) Prior Publication Data

US 2018/0250088 A1    Sep. 6, 2018

Related U.S. Application Data

(63) Continuation of application No. 14/608,915, filed on Jan. 29, 2015, now Pat. No. 9,962,226, which is a
(Continued)

(51) Int. Cl.
*A61B 50/20* (2016.01)
*A61B 46/10* (2016.01)
(Continued)

(52) U.S. Cl.
CPC .............. *A61B 46/10* (2016.02); *A61B 50/20* (2016.02); *A61B 50/30* (2016.02); *A61B 50/33* (2016.02);
(Continued)

(58) Field of Classification Search
CPC .. A61M 1/0003; A61F 9/00736; A61B 50/20; A61B 50/30; A61B 50/33
See application file for complete search history.

(56) References Cited

U.S. PATENT DOCUMENTS

| 3,116,828 A | 1/1964 | Glassman |
| 3,293,430 A | 12/1966 | Wustner |

(Continued)

FOREIGN PATENT DOCUMENTS

| CN | 2289530 Y | 9/1998 |
| EP | 0 876 799 | 11/1998 |

(Continued)

OTHER PUBLICATIONS

Extended European Search Report, dated Nov. 23, 2010, in European Patent Application No. 08746468.1.
(Continued)

*Primary Examiner* — Lynnsy M Summitt

(57) ABSTRACT

The disclosure herein provides ophthalmic surgical systems, methods, and devices. In one embodiment, a surgical apparatus for use by a surgeon during a surgical procedure comprises one or more sealed sterilized surgical packs configured to be disposed of after a single or a limited number of surgical procedures, the one or more sealed sterilized surgical packs comprising: a sterile surgical instrument; and a sterile surgical tray comprising a top surface configured to be part of a sterile field of the surgical procedure, the top surface comprising a receiving structure for positioning therein of the sterile surgical instrument, the sterile surgical tray further comprising walls that define a recess sized and configured to receive a reusable non-sterile module, the recess configured to encapsulate the reusable non-sterile module to isolate the reusable non-sterile module from the sterile field of the surgical procedure.

5 Claims, 38 Drawing Sheets

Related U.S. Application Data continuation-in-part of application No. 14/554,865, filed on Nov. 26, 2014.

(60) Provisional application No. 62/091,384, filed on Dec. 12, 2014, provisional application No. 61/990,021, filed on May 7, 2014, provisional application No. 61/924,164, filed on Jan. 6, 2014, provisional application No. 61/910,112, filed on Nov. 28, 2013.

(51) Int. Cl.
| | |
|---|---|
| *A61F 9/007* | (2006.01) |
| *A61F 9/008* | (2006.01) |
| *A61B 90/50* | (2016.01) |
| *A61B 50/30* | (2016.01) |
| *A61B 50/33* | (2016.01) |
| *A61B 90/30* | (2016.01) |
| *A61B 17/00* | (2006.01) |
| *A61B 17/32* | (2006.01) |
| *A61B 50/00* | (2016.01) |
| *A61B 46/00* | (2016.01) |
| *A61B 90/20* | (2016.01) |
| *A61B 90/00* | (2016.01) |

(52) U.S. Cl.
CPC ............. *A61B 90/30* (2016.02); *A61B 90/50* (2016.02); *A61F 9/00736* (2013.01); *A61F 9/00821* (2013.01); *A61B 17/32002* (2013.01); *A61B 46/00* (2016.02); *A61B 90/20* (2016.02); *A61B 2017/00115* (2013.01); *A61B 2017/00207* (2013.01); *A61B 2017/00367* (2013.01); *A61B 2017/00398* (2013.01); *A61B 2017/00477* (2013.01); *A61B 2017/00902* (2013.01); *A61B 2050/0051* (2016.02); *A61B 2050/3008* (2016.02); *A61B 2090/065* (2016.02); *A61B 2217/007* (2013.01)

(56) References Cited

U.S. PATENT DOCUMENTS

| | | | |
|---|---|---|---|
| 3,304,609 A | 2/1967 | Horowitz et al. | |
| 3,366,230 A | 1/1968 | Loran | |
| 3,702,940 A | 11/1972 | Stewart | |
| 3,820,656 A | 6/1974 | Orr | |
| 3,884,238 A | 5/1975 | O'Malley et al. | |
| 3,976,195 A | 8/1976 | Cohen | |
| 3,986,263 A | 10/1976 | Borgelt et al. | |
| 4,011,944 A | 3/1977 | Cooley et al. | |
| 4,014,342 A | 3/1977 | Staub et al. | |
| 4,019,514 A | 4/1977 | Banko | |
| 4,108,182 A | 8/1978 | Hartman et al. | |
| 4,112,947 A | 9/1978 | Nehring | |
| 4,117,843 A | 10/1978 | Banko | |
| 4,266,669 A | 5/1981 | Watson | |
| 4,288,733 A | 9/1981 | Bilanceri et al. | |
| 4,293,074 A | 10/1981 | Dunsky | |
| 4,320,761 A | 3/1982 | Haddad | |
| 4,324,243 A | 4/1982 | Helfgott et al. | |
| 4,378,108 A | 3/1983 | Bailey, Jr. | |
| 4,428,748 A | 1/1984 | Peyman et al. | |
| 4,430,062 A | 2/1984 | Henrichsen et al. | |
| 4,479,762 A | 10/1984 | Bilstad et al. | |
| 4,523,679 A * | 6/1985 | Paikoff | A61L 2/04 |
| | | | 206/363 |
| 4,595,102 A * | 6/1986 | Cianci | A61B 50/33 |
| | | | 206/370 |
| 4,713,051 A * | 12/1987 | Steppe | A61F 9/00736 |
| | | | 604/30 |
| 4,735,610 A | 4/1988 | Akkas et al. | |
| 4,798,580 A | 1/1989 | DeMeo et al. | |
| 4,869,266 A | 9/1989 | Taylor et al. | |
| 4,889,231 A | 12/1989 | Foote et al. | |
| 4,903,710 A | 2/1990 | Jessamine et al. | |
| 4,930,997 A | 6/1990 | Bennett | |
| 4,974,728 A | 12/1990 | Colton | |
| 5,007,535 A | 4/1991 | Meseke et al. | |
| 5,013,240 A | 5/1991 | Bailey et al. | |
| 5,078,677 A | 1/1992 | Gentelia et al. | |
| 5,392,917 A | 2/1995 | Alpern et al. | |
| 5,399,007 A | 3/1995 | Marconet | |
| 5,433,702 A | 7/1995 | Zelman et al. | |
| 5,455,766 A | 10/1995 | Scheller et al. | |
| 5,508,836 A | 4/1996 | DeCaro et al. | |
| 5,554,097 A | 9/1996 | Guy | |
| 5,586,163 A | 12/1996 | Goldstein | |
| 5,627,584 A | 5/1997 | Nishikori et al. | |
| 5,746,719 A | 5/1998 | Farra et al. | |
| 5,779,053 A * | 7/1998 | Partika | A61B 50/33 |
| | | | 206/370 |
| 5,800,396 A * | 9/1998 | Fanney | A61M 1/0058 |
| | | | 604/151 |
| 5,873,717 A | 2/1999 | Behringer | |
| 5,910,110 A | 6/1999 | Bastable | |
| 5,989,262 A | 11/1999 | Josephberg | |
| 6,022,088 A | 2/2000 | Metzler | |
| 6,024,699 A | 2/2000 | Surwit et al. | |
| 6,037,724 A | 3/2000 | Buss et al. | |
| 6,051,011 A | 4/2000 | Weidenbenner | |
| 6,059,792 A | 5/2000 | Josephberg | |
| 6,059,795 A | 5/2000 | Wallace et al. | |
| 6,074,399 A | 6/2000 | Wallace et al. | |
| 6,102,044 A | 8/2000 | Naidyhorki | |
| 6,117,127 A | 9/2000 | Helmreich et al. | |
| 6,158,437 A | 12/2000 | Vagley | |
| 6,185,096 B1 | 2/2001 | Helot et al. | |
| 6,206,014 B1 | 3/2001 | Cameron, III et al. | |
| 6,217,584 B1 | 4/2001 | Nun | |
| 6,251,113 B1 | 6/2001 | Appelbaum et al. | |
| 6,258,111 B1 | 7/2001 | Ross et al. | |
| 6,282,442 B1 | 8/2001 | Destefano et al. | |
| 6,312,258 B1 | 11/2001 | Ashman | |
| 6,355,047 B1 | 3/2002 | Wallace et al. | |
| 6,405,863 B1 | 6/2002 | Dhindsa | |
| 6,428,487 B1 | 8/2002 | Burdorff | |
| 6,508,823 B1 | 1/2003 | Gonon | |
| 6,579,255 B2 | 6/2003 | Kadziauskas et al. | |
| 6,616,606 B1 | 9/2003 | Petersen et al. | |
| 6,623,500 B1 | 9/2003 | Cook et al. | |
| 6,641,039 B2 | 11/2003 | Southard | |
| 6,648,223 B2 | 11/2003 | Boukhny et al. | |
| 6,666,875 B1 | 12/2003 | Sakurai et al. | |
| 6,716,219 B1 | 4/2004 | Koch | |
| 6,769,546 B2 | 8/2004 | Busch | |
| 6,896,141 B2 | 5/2005 | McMichael et al. | |
| 6,945,981 B2 | 9/2005 | Donofrio et al. | |
| 6,979,328 B2 | 12/2005 | Baerveldt et al. | |
| 7,100,771 B2 | 9/2006 | Massengale et al. | |
| 7,114,500 B2 | 10/2006 | Bonutti | |
| 7,165,555 B2 | 1/2007 | Lee | |
| 7,267,246 B2 | 9/2007 | Eiskant et al. | |
| 7,331,463 B2 | 2/2008 | Hickey | |
| 7,362,228 B2 | 4/2008 | Nycz et al. | |
| 7,401,703 B2 | 7/2008 | McMichael et al. | |
| 7,431,157 B2 | 10/2008 | Porret et al. | |
| 7,578,391 B2 | 8/2009 | Nakamura | |
| 7,604,007 B1 | 10/2009 | Wooley | |
| D626,238 S | 10/2010 | Zinnanti | |
| 7,883,465 B2 | 2/2011 | Donofrio et al. | |
| 7,886,743 B2 | 2/2011 | Cooper et al. | |
| 7,965,185 B2 * | 6/2011 | Cambre | G09B 23/28 |
| | | | 235/375 |
| 8,002,783 B2 | 8/2011 | Vercellotti et al. | |
| 8,172,834 B2 | 5/2012 | Bhadri et al. | |
| 8,177,064 B2 * | 5/2012 | McCormick | A61B 50/33 |
| | | | 206/370 |
| 8,177,776 B2 | 5/2012 | Humayun et al. | |
| 8,242,398 B2 | 8/2012 | Young et al. | |
| 8,323,271 B2 | 12/2012 | Humayun et al. | |
| 8,444,629 B2 | 5/2013 | Manna et al. | |
| 8,496,681 B2 | 7/2013 | Easley | |

(56) References Cited

U.S. PATENT DOCUMENTS

| | | | |
|---|---|---|---|
| 8,525,059 B2 | 9/2013 | Berger et al. | |
| 8,545,440 B2 | 10/2013 | Patrick et al. | |
| 8,568,391 B2 | 10/2013 | Kerns et al. | |
| 8,623,000 B2 | 1/2014 | Humayun et al. | |
| 8,827,945 B2 | 9/2014 | Baker et al. | |
| 9,126,270 B2 | 9/2015 | Nishio et al. | |
| 9,138,128 B2 | 9/2015 | Teichtmann | |
| 9,345,490 B2 | 5/2016 | Ippisch | |
| 9,393,075 B2 | 7/2016 | Ghosh | |
| 9,474,579 B2* | 10/2016 | Richman | A61B 50/20 |
| 9,526,580 B2 | 12/2016 | Humayun | |
| 9,745,180 B2 | 8/2017 | Beijer et al. | |
| 9,878,427 B2 | 1/2018 | Fuchs et al. | |
| 2001/0022615 A1 | 9/2001 | Fernandez et al. | |
| 2002/0013517 A1 | 1/2002 | West et al. | |
| 2003/0093503 A1 | 5/2003 | Yamaki et al. | |
| 2003/0159969 A1 | 8/2003 | McMichael et al. | |
| 2003/0165794 A1 | 9/2003 | Matoba | |
| 2003/0178488 A1 | 9/2003 | Southard | |
| 2003/0205233 A1 | 11/2003 | Aboul-Hosn et al. | |
| 2004/0004019 A1 | 1/2004 | Busch | |
| 2004/0116952 A1 | 6/2004 | Sakurai et al. | |
| 2004/0138518 A1 | 7/2004 | Rise et al. | |
| 2004/0139048 A1 | 7/2004 | Kerr, II et al. | |
| 2004/0186683 A1 | 9/2004 | Farber et al. | |
| 2004/0208780 A1 | 10/2004 | Faries, Jr. et al. | |
| 2004/0243147 A1 | 12/2004 | Lipow | |
| 2005/0100719 A1 | 5/2005 | KanaKarajan | |
| 2005/0128987 A1 | 6/2005 | Liang | |
| 2005/0228326 A1 | 10/2005 | Kalfas et al. | |
| 2005/0245888 A1 | 11/2005 | Cull | |
| 2005/0283138 A1 | 12/2005 | Tashiro et al. | |
| 2006/0002258 A1 | 1/2006 | Nakamura et al. | |
| 2006/0046226 A1 | 3/2006 | Bergler et al. | |
| 2006/0086634 A1 | 4/2006 | Steppe | |
| 2006/0095066 A1 | 5/2006 | Chang et al. | |
| 2006/0100497 A1 | 5/2006 | Sawazaki et al. | |
| 2006/0109105 A1 | 5/2006 | Varner et al. | |
| 2006/0119481 A1 | 6/2006 | Tethrake et al. | |
| 2006/0142739 A1 | 6/2006 | DiSilestro et al. | |
| 2006/0235436 A1* | 10/2006 | Anderson | A61B 34/71 606/130 |
| 2006/0244593 A1 | 11/2006 | Nycz et al. | |
| 2006/0255938 A1 | 11/2006 | Van den Brink | |
| 2006/0272979 A1 | 12/2006 | Lubbers et al. | |
| 2006/0289016 A1 | 12/2006 | Kammer et al. | |
| 2007/0167787 A1 | 7/2007 | Glossop et al. | |
| 2007/0282353 A1 | 12/2007 | Surti et al. | |
| 2007/0290654 A1 | 12/2007 | Govari et al. | |
| 2008/0004608 A1 | 1/2008 | Dacquay et al. | |
| 2008/0030345 A1 | 2/2008 | Austin et al. | |
| 2008/0041282 A1 | 2/2008 | Goschy et al. | |
| 2008/0077123 A1 | 3/2008 | Boyden et al. | |
| 2008/0077145 A1 | 3/2008 | Boyden | |
| 2008/0120137 A1 | 5/2008 | Nyholm | |
| 2008/0125761 A1 | 5/2008 | Weston et al. | |
| 2008/0167644 A1 | 7/2008 | Shelton et al. | |
| 2008/0208233 A1 | 8/2008 | Barnes et al. | |
| 2008/0272023 A1* | 11/2008 | McCormick | A61B 50/33 206/570 |
| 2008/0281254 A1 | 11/2008 | Humayun et al. | |
| 2008/0281301 A1 | 11/2008 | DeBoer et al. | |
| 2008/0308698 A1 | 12/2008 | Steppe | |
| 2009/0163897 A1 | 6/2009 | Skinner | |
| 2009/0313773 A1 | 12/2009 | Filsouf | |
| 2010/0069825 A1 | 3/2010 | Raney | |
| 2010/0134303 A1 | 6/2010 | Perkins | |
| 2010/0174415 A1 | 7/2010 | Humayun et al. | |
| 2011/0105999 A1 | 5/2011 | Akahoshi | |
| 2011/0112518 A1 | 5/2011 | Stanton | |
| 2011/0130632 A1 | 6/2011 | McGrail | |
| 2011/0144567 A1 | 6/2011 | Sorensen et al. | |
| 2011/0203821 A1 | 8/2011 | Puzio et al. | |
| 2011/0257481 A1 | 10/2011 | Ogawa | |
| 2011/0276340 A1 | 11/2011 | DeBoer et al. | |
| 2011/0295193 A1 | 12/2011 | Fitzgerald et al. | |
| 2012/0022510 A1 | 1/2012 | Welches et al. | |
| 2012/0232540 A1 | 9/2012 | Baur et al. | |
| 2013/0009606 A1 | 1/2013 | Smith et al. | |
| 2014/0238890 A1 | 8/2014 | Kerns et al. | |
| 2014/0271251 A1 | 9/2014 | Bourne et al. | |
| 2014/0271273 A1 | 9/2014 | Carpenter | |
| 2014/0323813 A1 | 10/2014 | Humayun et al. | |
| 2014/0365235 A1 | 12/2014 | DeBoer et al. | |
| 2014/0378952 A1 | 12/2014 | Humayun et al. | |
| 2015/0144514 A1 | 5/2015 | Brennan | |
| 2015/0148615 A1 | 5/2015 | Brennan et al. | |
| 2015/0238264 A1 | 8/2015 | Kerns | |

FOREIGN PATENT DOCUMENTS

| | | |
|---|---|---|
| EP | 1 236 439 | 9/2002 |
| EP | 1 813 199 | 8/2007 |
| EP | 2 441 393 | 4/2012 |
| JP | 05-044111 U | 6/1993 |
| JP | 2004-250108 | 6/1993 |
| JP | 3 310 360 | 5/2002 |
| JP | 2002-515293 | 5/2002 |
| JP | 2002/233534 | 8/2002 |
| JP | 3 088 841 | 10/2002 |
| JP | 2002/345839 | 12/2002 |
| JP | 2005-046412 | 2/2005 |
| JP | 2006-511285 | 4/2006 |
| JP | 2007-501055 | 1/2007 |
| JP | 2007167644 A | 7/2007 |
| JP | 2009-219718 | 10/2009 |
| JP | 2010-503513 | 2/2010 |
| JP | 2011/045961 | 3/2011 |
| JP | 2011516120 A | 5/2011 |
| JP | 2012/223243 | 11/2012 |
| JP | 2013516287 A | 5/2013 |
| WO | WO 92/20310 | 11/1992 |
| WO | WO 95/01135 | 1/1995 |
| WO | WO 98/06338 | 2/1998 |
| WO | WO 99/59510 | 11/1999 |
| WO | WO 99/66444 | 12/1999 |
| WO | WO 2000/32115 | 6/2000 |
| WO | WO 01/12098 | 2/2001 |
| WO | WO 02/083021 | 10/2002 |
| WO | WO 03/034213 | 4/2003 |
| WO | WO 2004/060184 | 7/2004 |
| WO | WO 2004/105631 | 12/2004 |
| WO | WO 2005/016183 | 2/2005 |
| WO | WO 2008/036453 | 3/2008 |
| WO | WO 2008/131357 | 10/2008 |
| WO | WO 2008/152378 | 12/2008 |
| WO | WO 2010/030850 | 3/2010 |
| WO | 2012/151062 | 11/2012 |
| WO | 2014/025702 | 2/2014 |

OTHER PUBLICATIONS

International Preliminary Report on Patentability and Written Opinion, dated Apr. 26, 2011, in PCT Application No. PCT/US2008/080832.

International Preliminary Report on Patentability and Written Opinion, dated Oct. 20, 2009, in PCT Application No. PCT/US2008/061058.

International Preliminary Report on Patentability, dated Jan. 10, 2012, in PCT Application No. PCT/US2011/20415.

International Preliminary Report on Patentability, dated Nov. 5, 2013, in PCT Application No. PCT/US2012/034480.

International Search Report and Written Opinion, dated Sep. 2, 2008, in PCT Application No. PCT/US 2008/061043.

International Search Report and Written Opinion, dated Aug. 27, 2008, in PCT Application No. PCT/US2008/061058.

International Search Report and Written Opinion, dated Dec. 22, 2008, in PCT Application No. PCT/US2008/061065.

International Search Report and Written Opinion, dated Jul. 29, 2010, in PCT Application No. PCT/US2008/080832.

International Search Report and Written Opinion, dated Jun. 2, 2011, in PCT Application No. PCT/US2011/020415.

(56) References Cited

OTHER PUBLICATIONS

International Search Report and Written Opinion, dated Oct. 18, 2012, in PCT Application No. PCT/US2012/034480.
International Search Report and Written Opinion, dated May 20, 2015, in PCT Application No. PCT/US2015/013567.
Merriam-Webster.com definition of "tray"; http://www.merriam-webster.comidictionary/tray.
Partial International Search Report, dated Apr. 27, 2010, in PCT Application No. PCT/US2008/080832.
Partial International Search Report, dated Jul. 6, 2012, in PCT Application No. PCT/US2012/034480.
Supplementary European Search Reported, dated Dec. 10, 2010, in European Patent Application No. 08746468.1.
International Search Report and Written Opinion issued in PCT Application No. PCT/US2014/067717, dated Mar. 5, 2015.
Extended European Search Report for European Patent Application No. 14866168.9, dated Apr. 7, 2017; 6 pages.
International Preliminary Report on Patentability and Written Opinion received for International Application No. PCT/US2014/067717, dated Jun. 9, 2016; 11 pages.
International Preliminary Report on Patentability and Written Opinion received for International Application No. PCT/US2015/013567, dated Nov. 17, 2016; 14 pages.
Partial Supplementary European Search Report for European Patent Application No. 15789716.6, dated Jan. 3, 2018; 12 pages.
Office Action for Japanese Patent Application No. 2016-534948, dated Aug. 7, 2018, no English translation; 3 pages.

\* cited by examiner

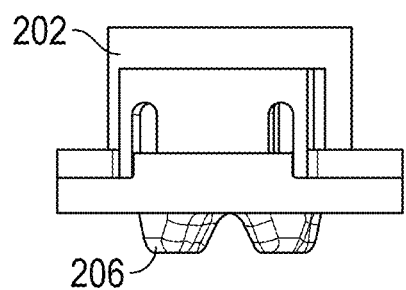
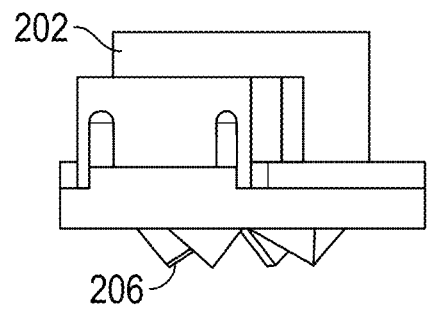
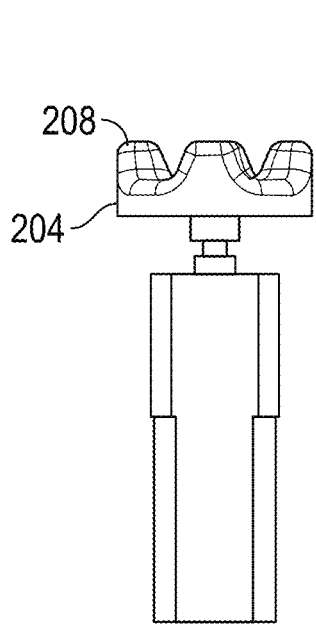
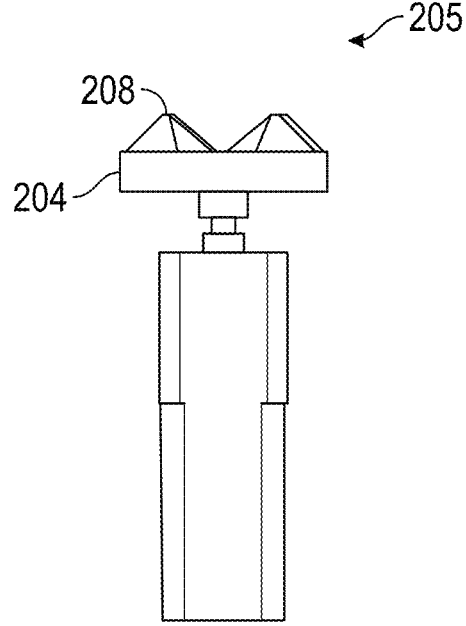
FIG. 2J FIG. 2K

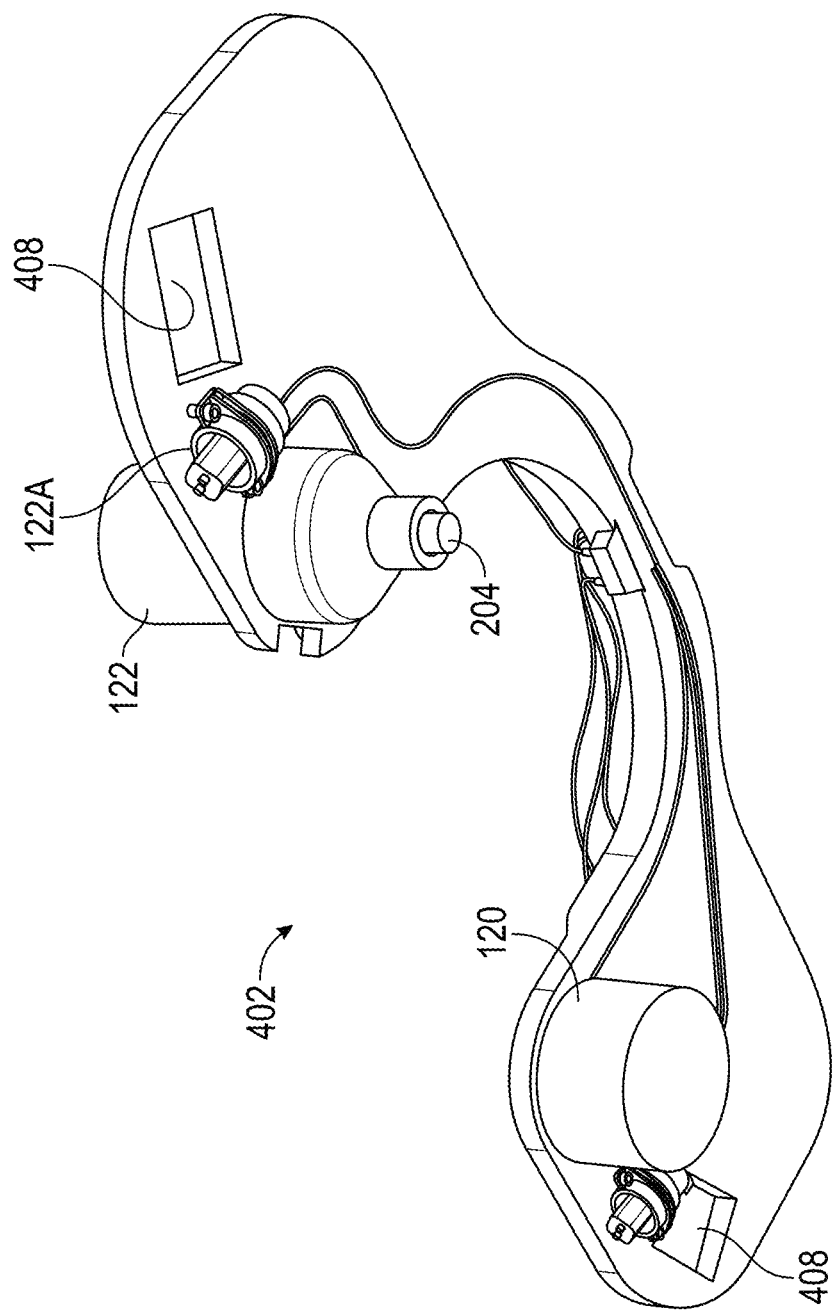

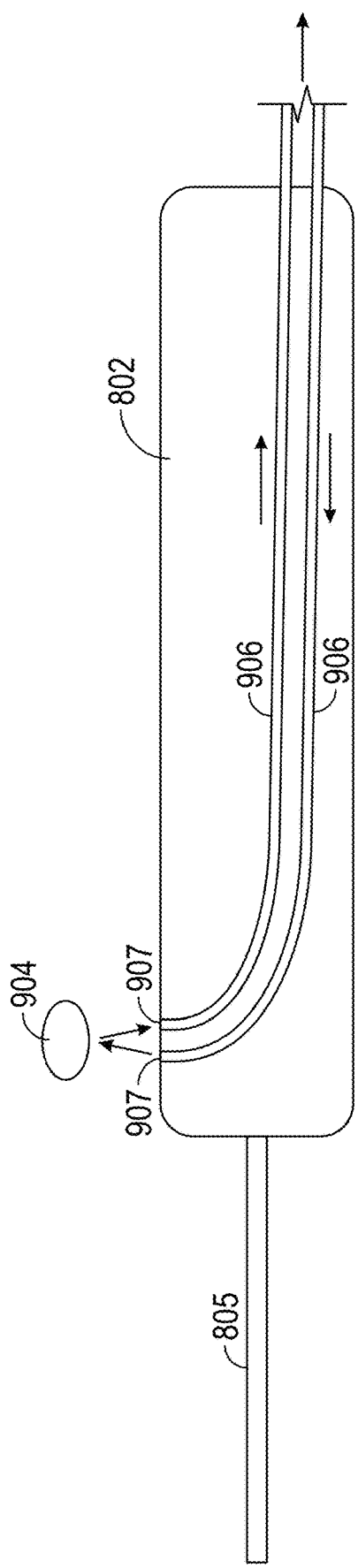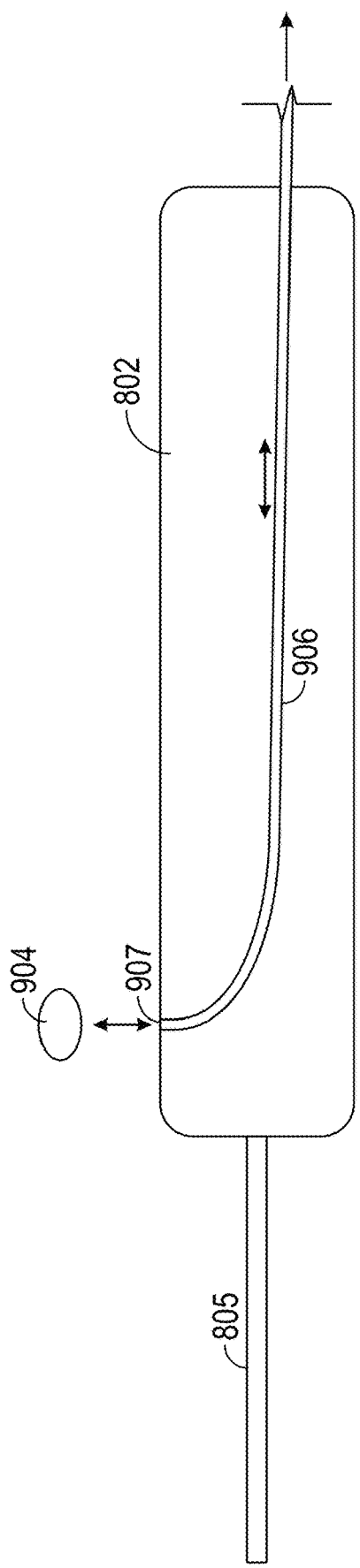

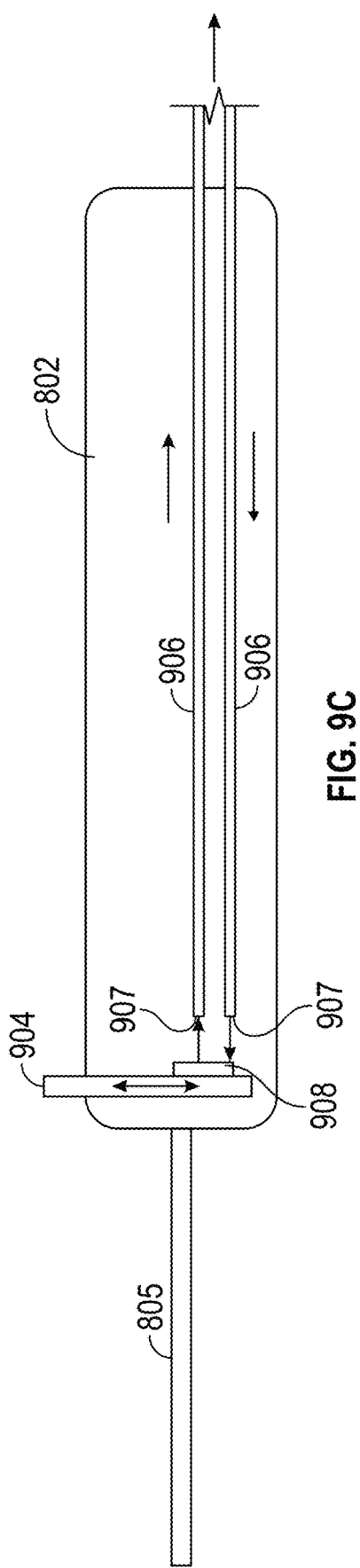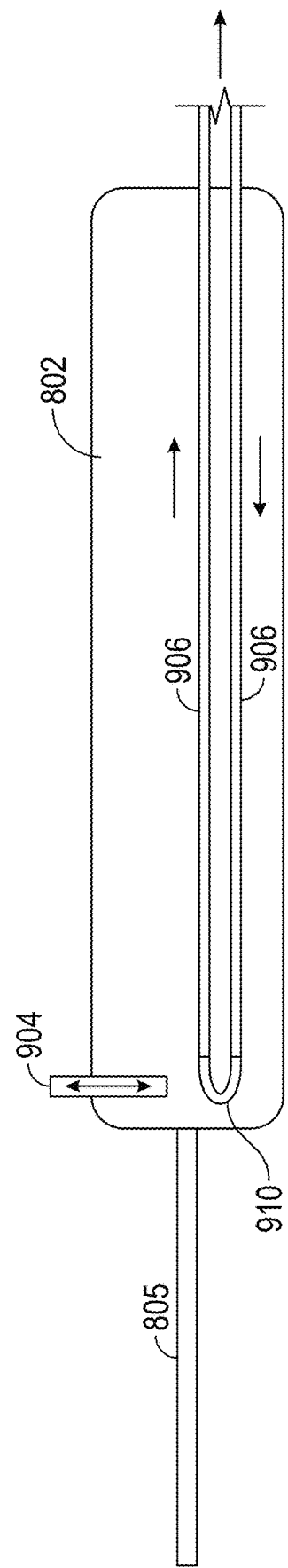

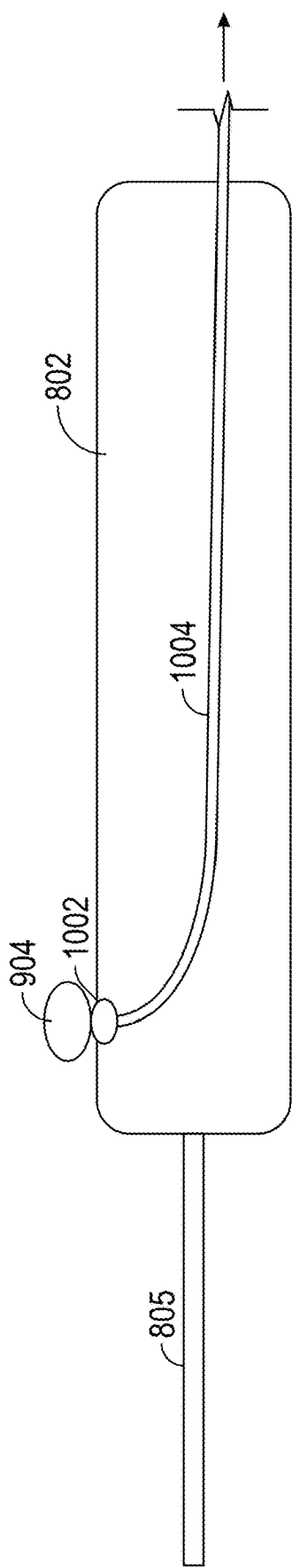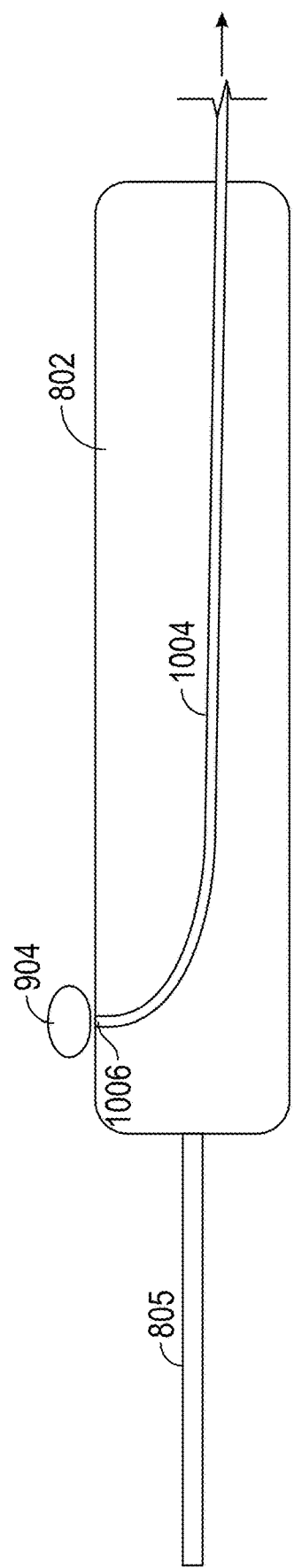

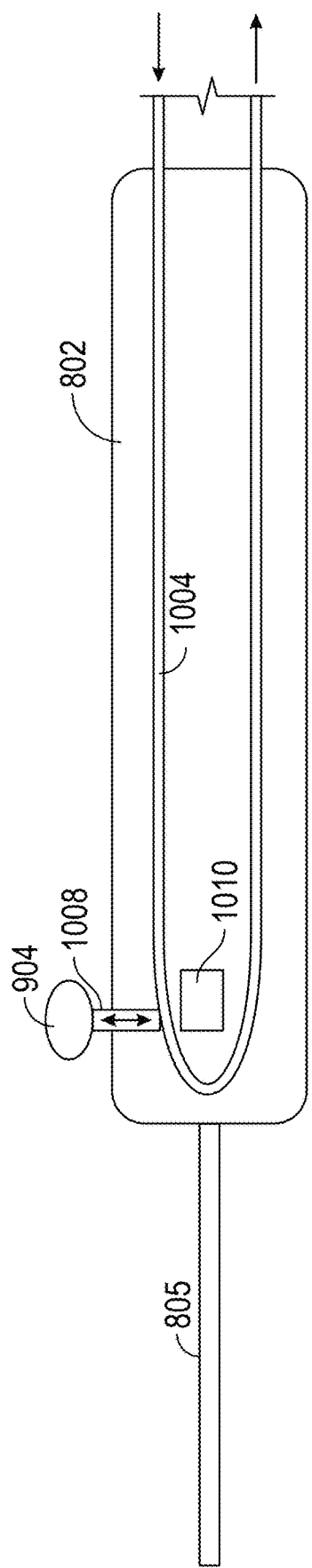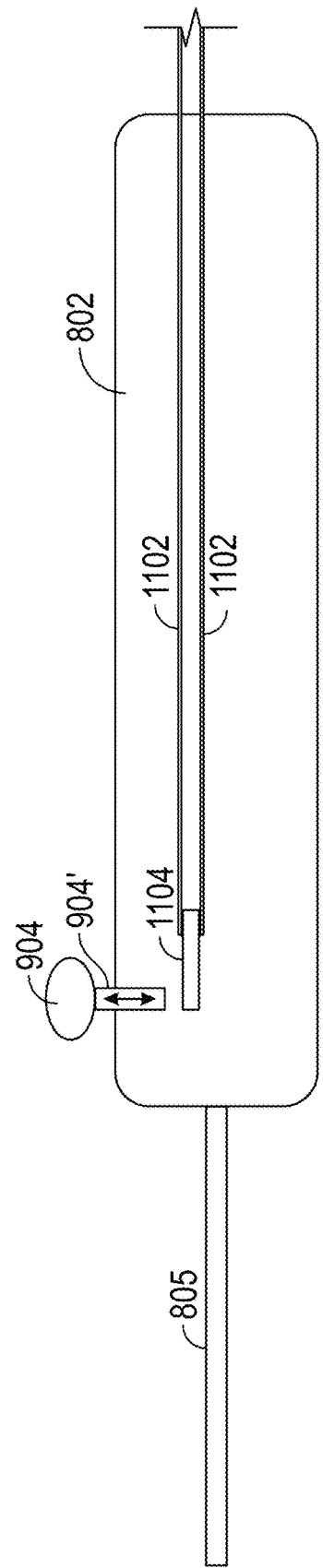
FIG. 10C
FIG. 11

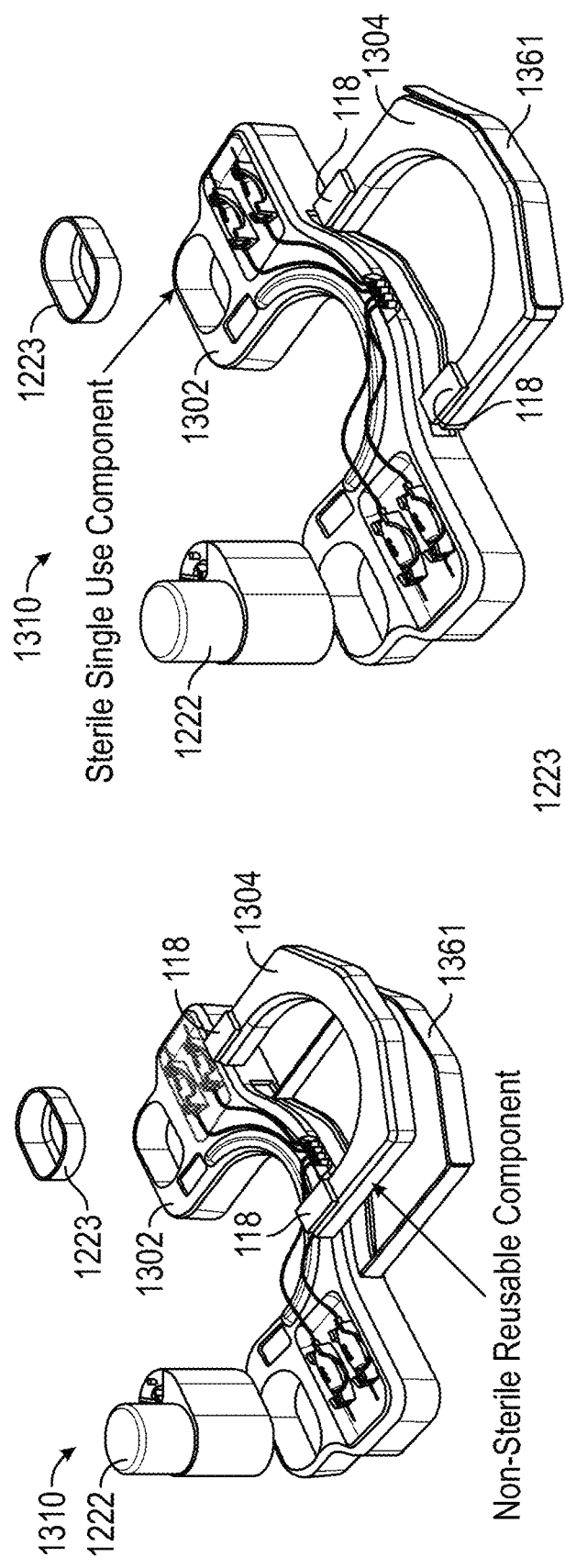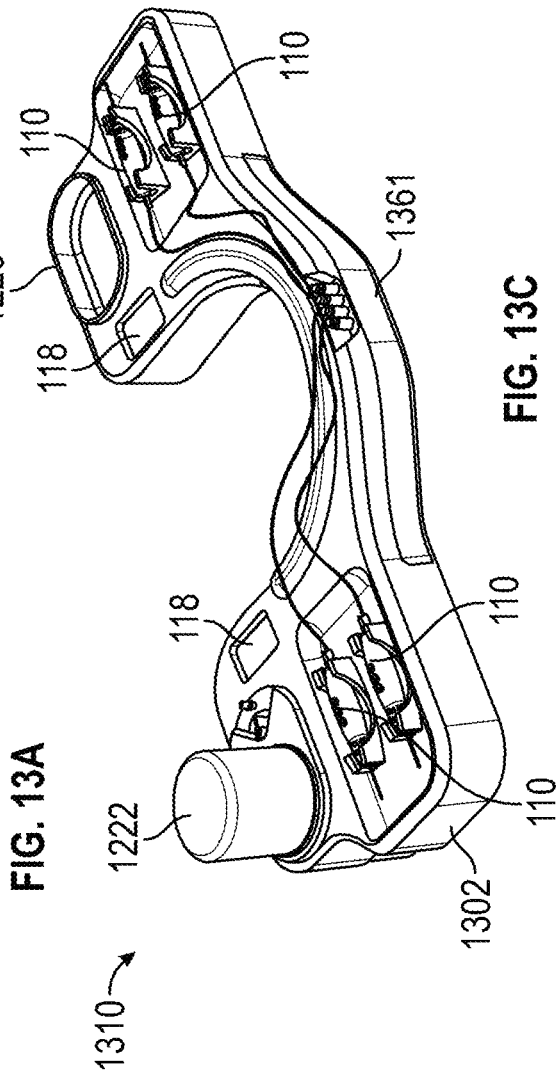
FIG. 13A
FIG. 13B
FIG. 13C

OPHTHALMIC SURGICAL SYSTEMS, METHODS, AND DEVICES

CROSS-REFERENCE TO RELATED APPLICATIONS

This application is a is a continuation of U.S. patent application Ser. No. 14/608,915, filed Jan. 29, 2015, which is a continuation-in-part of U.S. patent application Ser. No. 14/554,865, filed Nov. 26, 2014, which claims the benefit of U.S. Provisional Application No. 61/990,021, filed May 7, 2014, and of U.S. Provisional Application No. 61/924,164, filed Jan. 6, 2014, and of U.S. Provisional Application No. 61/910,112, filed Nov. 28, 2013. U.S. patent application Ser. No. 14/608,915 claims the benefit of U.S. Provisional Application No. 62/091,384, filed Dec. 12, 2014. Each of the foregoing applications is hereby incorporated by reference herein in its entirety.

BACKGROUND

Field

The disclosure relates generally to the field of ophthalmic surgery, and more specifically to ophthalmic surgical systems, methods, and devices.

Description

The field of ophthalmology has become increasingly important in today's society as adults are living longer and older generations comprise a growing proportion of the world population. Vision care and the treatment of ocular diseases or conditions have benefited in recent years from advancements in both pharmacology and medical device technologies. Microsurgical instruments and innovative surgical techniques enable surgeons to repair or replace parts of the eye previously considered inaccessible and off-limits. In particular, console systems that provide a variety of functions dedicated to a specific set of procedures (such as vitrectomy or cataract removal procedures) are now available to surgeons, with improvements and updates to the technology occurring on a regular basis. Often times these consoles are very expensive, requiring a large capital expenditure by a surgeon, hospital, or ambulatory surgical center. They also often have high recurring costs for the single-use disposable elements of the system, and may have high maintenance costs as well. The consoles often incorporate a lot of unnecessary or infrequently used functionality in order to differentiate from competing products. Hence, in addition to being costly, the consoles are often large, heavy, bulky, noisy, power-hungry, and bloated machines that contrast sharply with the small, delicate eye they are designed to treat. Furthermore, the drawbacks of these systems often require them to be located some distance from the surgeon, resulting in long tubing sets and/or cables that negatively impact the performance of the system while increasing the cost. Hence, there is a need for smaller, more portable, more self-contained, and more cost-effective systems that incorporate the major functions required to perform certain procedures.

SUMMARY

The disclosure herein provides ophthalmic surgical systems, methods, and devices. In some embodiments, a surgical apparatus or tray comprises one or more reusable components and one or more disposable components configured to be used with the reusable components. In some embodiments, the disposable components can be configured to be disposed of after a single use or a limited number of uses. In some embodiments, the one or more reusable portions comprise a non-sterile component configured to not be in a sterile surgical environment, while the one or more disposable components are configured to be used in the sterile surgical environment. In some embodiments, a sterile disposable portion is configured to encapsulate or otherwise isolate a non-sterile reusable portion from a sterile surgical environment. In some embodiments, a handheld surgical instrument comprises a pressure sensitive button for controlling a surgical function. In some embodiments, the pressure sensitive button is positioned circumferentially around a body of the surgical tool, such that external pressure applied to the button at any or substantially any location around the circumference (or at any location within a predefined range, such as, for example, about 350, 325, 300, 275, 250, 225, 200, or 180 degrees of the full circumference) is detectable by the pressure sensitive button. In some embodiments, a handheld surgical instrument comprises a nonelectric button, such as, for example, a pneumatic, hydraulic, optical, and/or the like button. In some embodiments, an ophthalmic surgical system is configured to utilize a reusable base and a disposable sterile surgical tray coupled thereto. In some embodiments, some functions are contained within or coupled to the disposable tray, such as, for example, fluidics and/or handpieces; and reusable components, such as, for example, a power source (for example, electrical, mechanical, hydraulic, pneumatic, optical, and/or the like) for the handpieces located in the reusable base. In some embodiments, a custom surgical drape is provided which comprises one or more functional interfaces enabling a function to pass therethrough. In some embodiments, the function configured to pass therethrough may comprise an electrical current, light, pneumatic or fluidic coupling, and/or a mechanical coupling or other feature. In some embodiments, an ophthalmic surgical system is configured to be automatically updated or configured in response to detection of a tag, such as an RFID tag, a near field communication device, a memory card/USB, or other storage device, and/or the like.

According to some embodiments, a surgical apparatus for use by a surgeon during a surgical procedure comprises: one or more sealed sterilized surgical packs configured to be unsealed before a surgical procedure and disposed of after a single or a limited number of surgical procedures, the one or more sealed sterilized surgical packs comprising: a sterile surgical instrument; and a sterile surgical tray comprising a top surface configured to be part of a sterile field of the surgical procedure, the sterile surgical tray further comprising walls that define a recess sized and configured to receive a reusable non-sterile module, the recess configured to fully or partially encapsulate the reusable non-sterile module to isolate the reusable non-sterile module from the sterile field of the surgical procedure, wherein the walls of the sterile surgical tray comprises one or more interfaces positioned and configured to enable one or more functions of the reusable non-sterile module to be utilized in the sterile field of the surgical procedure outside of the recess. In some embodiments, the one or more interfaces comprises at least an electronic communication interface configured to enable an electronic controller of the reusable non-sterile module to electronically communicate with the sterile surgical tray or the sterile surgical instrument.

In some embodiments, the recess is centrally located in the sterile surgical tray. In some embodiments, the sterile surgical tray comprises at least two pieces selectively coupleable together to form the recess that encapsulates the reusable non-sterile module. In some embodiments, the sterile surgical tray comprises a hinged opening for access to the recess. In some embodiments, the one or more interfaces comprises a mechanical coupling for transmission of rotational motion from a motor of the reusable non-sterile module to a fluid pump connected to the sterile surgical tray. In some embodiments, the one or more interfaces comprises a light transmission coupling for transmission of light from a light source of the reusable non-sterile module to the sterile surgical instrument. In some embodiments, the one or more interfaces comprises an electrically conductive coupling for transmission of electrical power from the non-sterile module to the sterile surgical tray. In some embodiments, the one or more interfaces comprises an electronic communication coupling for enabling electronic communication between the non-sterile module and the sterile surgical tray or sterile surgical instrument. In some embodiments, the one or more functions of the reusable non-sterile module comprise at least one of the following: providing mechanical power, providing electrical power, providing electronic processing or control, providing a laser source, providing a light source, and displaying information. In some embodiments, the top surface of the sterile surgical tray comprises a receiving structure for positioning therein of the sterile surgical instrument.

According to some embodiments, a surgical apparatus for use by a surgeon during a surgical procedure comprises: one or more sealed sterilized surgical packs configured to be unsealed before a surgical procedure and disposed of after a single or a limited number of surgical procedures, the one or more sealed sterilized surgical packs comprising: a sterile surgical instrument; and a sterile surgical tray comprising a top surface configured to be part of a sterile field of the surgical procedure, and a bottom surface sized and configured to couple to and be supported by an upper surface of a reusable support structure, the reusable support structure comprising at least one of: a motor, a light source, and a user interface display, wherein the sterile surgical tray comprises at least one of: a mechanical coupling for transmission of rotational motion from the motor of the support structure to a fluid pump connected to the sterile surgical tray, a light transmission coupling for transmission of light from the light source of the support structure to the sterile surgical instrument, and a transparent material positioned to enable the user interface display of the support structure to be visible therethrough in the sterile field of the surgical procedure.

In some embodiments, the one or more sealed sterilized surgical packs further comprises a sterile drape sized to be positioned between the bottom surface of the sterile surgical tray and the upper surface of the reusable support structure. In some embodiments, the sterile drape comprises a conductive interface configured to enable electrical current to pass from the reusable support structure to the sterile surgical tray. In some embodiments, the reusable support structure is non-sterile. In some embodiments, the sterile surgical tray comprises a collapsed shipping configuration and an expanded surgical use configuration. In some embodiments, at least a portion of the sterile surgical tray is configured to, in the collapsed shipping configuration, protect the sterile surgical tool from damage. In some embodiments, the reusable support structure comprises the motor, and the one or more sealed sterilized surgical packs further comprises a sterile pump module separate from the sterile surgical tray and configured to separately couple to and be supported by the reusable support structure, wherein the sterile pump module comprises a rotational coupling for transmission of rotational motion from the motor to a fluid pump of the pump module. In some embodiments, the top surface of the sterile surgical tray comprises a receiving structure for positioning therein of the sterile surgical instrument.

According to some embodiments, a surgical apparatus for use by a surgeon during a surgical procedure comprises: one or more sealed sterilized surgical packs configured to be unsealed before a surgical procedure and disposed of after a single or a limited number of surgical procedures, the one or more sealed sterilized surgical packs comprising: a sterile surgical instrument; a sterile surgical instrument holder comprising a top surface configured to be part of a sterile field of the surgical procedure, the top surface comprising a receiving structure for positioning therein of the sterile surgical instrument, the sterile surgical instrument holder further comprising a bottom surface sized and configured to be received in a first recess of a reusable support structure; and a sterile infusion module sized and configured to be received in a second recess of the reusable support structure, the sterile infusion module comprising a pump head configured to couple with a motor of the reusable support structure to enable pumping of fluids into the sterile field or surgical site. In some embodiments, the one or more sealed sterilized surgical packs further comprises (or the sterile surgical instrument, sterile surgical instrument holder, and/or sterile infusion modules is replaced with) a sterile aspiration module comprising a pump head configured to couple with the motor of the reusable support structure to enable pumping of fluids out of the sterile field or surgical site. In some embodiments, the sterile infusion module and/or sterile aspiration module comprises a pump head coupled to a motor, instead of a pump head configured to couple with a motor of the reusable support structure.

In some embodiments, the sterile surgical instrument holder comprises a collapsed configuration and an expanded configuration, the collapsed configuration configured to protect the surgical instrument in shipping, the expanded configuration configured to enable access to the surgical instrument in the sterile field of the surgical procedure. In some embodiments, the one or more sealed sterilized surgical packs further comprises a second sterile surgical instrument holder comprising a receiving structure for positioning therein of a second sterile surgical instrument, the surgical instrument holders shaped and configured to couple together in a collapsed configuration for protection of the surgical instruments in shipping. In some embodiments, the surgical instrument is configured to couple with one or more of: a light source of the reusable support structure, an electronic controller of the reusable support structure, a mechanical driver of the reusable support structure (for example, a transmission cable or torque coil, and/or the like), and a pneumatic or fluidic driver of the reusable support structure (for example, a pump, compressed source, and/or the like). In some embodiments, the reusable support structure is non-sterile. In some embodiments, the one or more sealed sterilized surgical packs further comprises a surgical drape configured be positioned between the non-sterile reusable support structure and at least one of the surgical instrument holder and the infusion module.

According to some embodiments, a surgical apparatus for use by a surgeon during a surgical procedure comprises: one or more sealed sterilized surgical packs configured to be unsealed before a surgical procedure and disposed of after a single or a limited number of surgical procedures, the one or more sealed sterilized surgical packs comprising one or more of a sterile infusion module and a sterile aspiration module, the sterile infusion and aspiration modules each comprising: a housing comprising walls sized and configured to be removably received in a recess of a reusable support structure, and at least one outer surface configured to be part of the sterile field of the surgical procedure; a pump for pumping fluids into or out of a surgical site; and a motor coupled to the pump for rotating a rotor of the pump, wherein the housing further comprises an electrical interface configured to receive electrical power from the reusable support structure for powering the motor, wherein the sterile infusion module is configured to pump fluids into the surgical site, and the sterile aspiration module is configured to pump fluids out of the surgical site.

In some embodiments, the one or more sealed sterilized surgical packs comprises at least one of each of the sterile infusion module and the sterile aspiration module. In some embodiments, the pump comprises a sterilization configuration wherein at most one pinch-point is created in peristaltic tubing of the pump. In some embodiments, the pump comprises a plurality of rollers repositionable from a sterilization position to an operating position, wherein, in the sterilization position, the rollers are closer to a central axis of the pump than in the operating position. In some embodiments, the one or more sealed sterilized surgical packs further comprises: a sterile surgical instrument; and a sterile surgical instrument holder comprising a top surface configured to be part of the sterile field of the surgical procedure, the top surface comprising a receiving portion for positioning therein or thereon of the sterile surgical instrument, the sterile surgical instrument holder further comprising a bottom surface sized and configured to be received in a different recess of the reusable support structure. In some embodiments, the reusable support structure is non-sterile, and the one or more sealed sterilized surgical packs further comprises a surgical drape configured be positioned between the non-sterile reusable support structure and at least one of the modules.

According to some embodiments, a handheld medical instrument for surgical procedures comprises: a body having an exterior surface shaped to be held and manipulated by a human hand; a surgical tool extending from a distal end of the body; and a pressure-sensitive button for controlling operation of the surgical tool, the pressure-sensitive button comprising an actuation surface positioned adjacent the exterior surface of the body, the pressure-sensitive button further comprising a pressure detection device, the pressure detection device configured to enable output of a signal for controlling a function of the surgical tool, the signal being proportional to a position of the actuation surface.

In some embodiments, the pressure detection device comprises a force sensitive resistor that changes a resistance based on the position of the actuation surface. In some embodiments, the actuation surface extends circumferentially around an exterior of the body and is positioned at least partially around a conductive surface of the force sensitive resistor. In some embodiments, the pressure detection device comprises an optical fiber positioned such that movement of the actuation surface with respect to the body causes the optical fiber to deform. In some embodiments, the pressure detection device comprises an optical fiber and an optical detection member, wherein movement of the actuation surface with respect to the body causes the optical detection member to move in a way that affects a light signal of the optical fiber. In some embodiments, the pressure detection device comprises a deformable member coupled to the actuation surface such that movement of the actuation surface with respect to the body deforms the deformable member, causing a change in pressure within the deformable member. In some embodiments, the pressure detection device comprises a piezoelectric material coupled to the actuation surface such that movement of the actuation surface with respect to the body causes deformation of the piezoelectric material. In some embodiments, the surgical tool comprises at least one of: an aspiration device, an endoillumination device, a laser therapy device, a lens removal device, a trabecular meshwork removal device, and a vitreous cutting device. In some embodiments, the controlled function of the surgical tool comprises at least one of: a speed and an intensity. For example, the controlled function can be configured to be controlling the intensity of infusion pressure or aspiration vacuum. In some embodiments, the proportionality of the signal in relation to the position of the actuation surface is linear. The term "linear" as used herein is a broad term, and unless otherwise indicated, the term can include within its meanings, without limitation, a reference to the concept of a variable output that is proportional to some input (for example, the applied force or deflection), but in some embodiments, the term "linear" can refer to a response that is not necessarily a linearly proportional response and can include a non-linear response (for example, logarithmic or exponential response based on a linear input), and in some embodiments, the term "linear" can refer to a response that is a combination of a linear and non-linear response (for example, the initial range of an input produces an initial response that is linear and a second range of the input produces a response that is non-linear). In some embodiments, the actuation surface is movable between a fully outward position and a fully depressed position, wherein the actuation surface is biased outward, such that the actuation surface remains in the fully outward position until an external force is applied that overcomes a biasing force. In some embodiments, the signal is configured to control simultaneously the function of the surgical tool and at least one other surgical function. In some embodiments, the handheld medical instrument further comprises a second pressure-sensitive button comprising a second actuation surface and second pressure detection device configured to enable controlling of a second surgical function. In some embodiments, the handheld medical instrument further comprises a tether coupled to a surgical tray. In some embodiments, the pressure detection device is configured to transmit the signal to a processor (for example, a computer process, controller, microelectronics, and/or the like) external to the medical instrument for interpretation of the signal for controlling of the function of the surgical tool. In some embodiments, the signal controls the function of the surgical tool without the signal being transmitted to a processor external to the medical instrument for interpretation. In some embodiments, the body comprises at least one of the following: an elongate cylindrical shape and an elongate rounded shape.

According to some embodiments, a handheld medical instrument for surgical procedures comprises: a body having an exterior surface shaped to be held and manipulated by a human hand; a surgical tool extending from a distal end of the body; a button for controlling operation of the surgical tool, the button positioned adjacent the exterior surface of the body, wherein the button comprises a non-electrical detection mechanism; and a signal transfer conduit configured to enable output of a signal from the non-electrical detection mechanism for controlling a function of the surgical tool.

In some embodiments, the signal transfer conduit comprises an optical fiber, and the detection mechanism comprises an end surface of the optical fiber. In some embodiments, the signal transfer conduit comprises an optical fiber, and the detection mechanism comprises an optical detection member, wherein movement of the optical detection member with respect to the body affects a light signal of the optical fiber. In some embodiments, the signal transfer conduit comprises an optical fiber, and the detection mechanism comprises a portion of the optical fiber that is deformable by movement of an actuation surface with respect to the body. In some embodiments, the signal transfer conduit comprises one of a pneumatic and a hydraulic tube, and the detection mechanism comprises an opening of the tube or an opening fluidly coupled to the tube, the opening positioned adjacent the exterior surface of the body. In some embodiments, the signal transfer conduit comprises one of a pneumatic and a hydraulic tube, and the detection mechanism comprises an actuation surface movably coupled to the body, wherein movement of the actuation surface with respect to the body causes to deform one of a portion of the tube and a deformable member fluidly coupled to the tube. In some embodiments, the surgical tool comprises at least one of: an aspiration device, an endoillumination device, a laser therapy device, a lens removal device, a trabecular meshwork removal device, and a vitreous cutting device. In some embodiments, the controlled function of the surgical tool comprises at least one of: a speed and an intensity. In some embodiments, the handheld medical instrument further comprises a tether coupled to a surgical tray. In some embodiments, the pressure detection device is configured to transmit the signal to a processor external to the medical instrument for interpretation of the signal for controlling of the function of the surgical tool. In some embodiments, the body comprises at least one of the following: an elongate cylindrical shape and an elongate rounded shape.

According to some embodiments, a surgical drape for use in a sterile operating field comprises: a flexible sheet sized to be at least partially sandwiched between first and second surgical devices and to at least partially cover the second surgical device to maintain a sterile barrier between the first and second surgical devices; and at least one access interface integrally formed or coupled to the flexible sheet, wherein the access interface is configured to enable at least one of the following to pass therethrough while maintaining the sterile barrier: electrical current, light, a mechanical coupling, an optical coupling, a fluid coupling, and a pneumatic coupling.

In some embodiments, the access interface is positionable at an electrical interface of the first and second surgical devices, and the access interface comprises electrical contacts configured to enable electrical current to pass therethrough. In some embodiments, the access interface is positionable at an electrical interface of the first and second surgical devices, and the access interface comprises an anisotropically conductive material. In some embodiments, the access interface comprises an optically-transparent window. In some embodiments, the access interface comprises a perforated region. In some embodiments, the functional interface comprises a sealing feature that forms a seal around the perforated region. In some embodiments, the access interface comprises a region to be punctured. In some embodiments, the functional interface comprises a sealing feature that forms a seal around the punctured region. In some embodiments, the second surgical device comprises a reusable base, and the first surgical device comprises a sterile surgical tray configured to be releasably coupled to the base, wherein the flexible sheet is form-fitted to the reusable base.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The foregoing and other features, aspects, and advantages of the present invention are described in detail below with reference to the drawings of various embodiments, which are intended to illustrate and not to limit the invention. The drawings comprise the following figures in which:

FIGS. 2A-2K illustrate a variety of embodiments of coupling mechanisms.

FIGS. 4A-4F illustrate embodiments of a modular surgical tray system.

FIGS. 9A-9D illustrate example embodiments of handpieces comprising one or more optical buttons.

FIGS. 10A-10C illustrate example embodiments of handpieces comprising pneumatic or hydraulic buttons.

FIG. 11 illustrates an embodiment of a handpiece comprising a piezoelectric button.

FIGS. 13A-13C illustrate another embodiment of a surgical tray system that isolates a non-sterile reusable component from a sterile surgical field.

DETAILED DESCRIPTION OF THE EMBODIMENTS

Figure 1A:
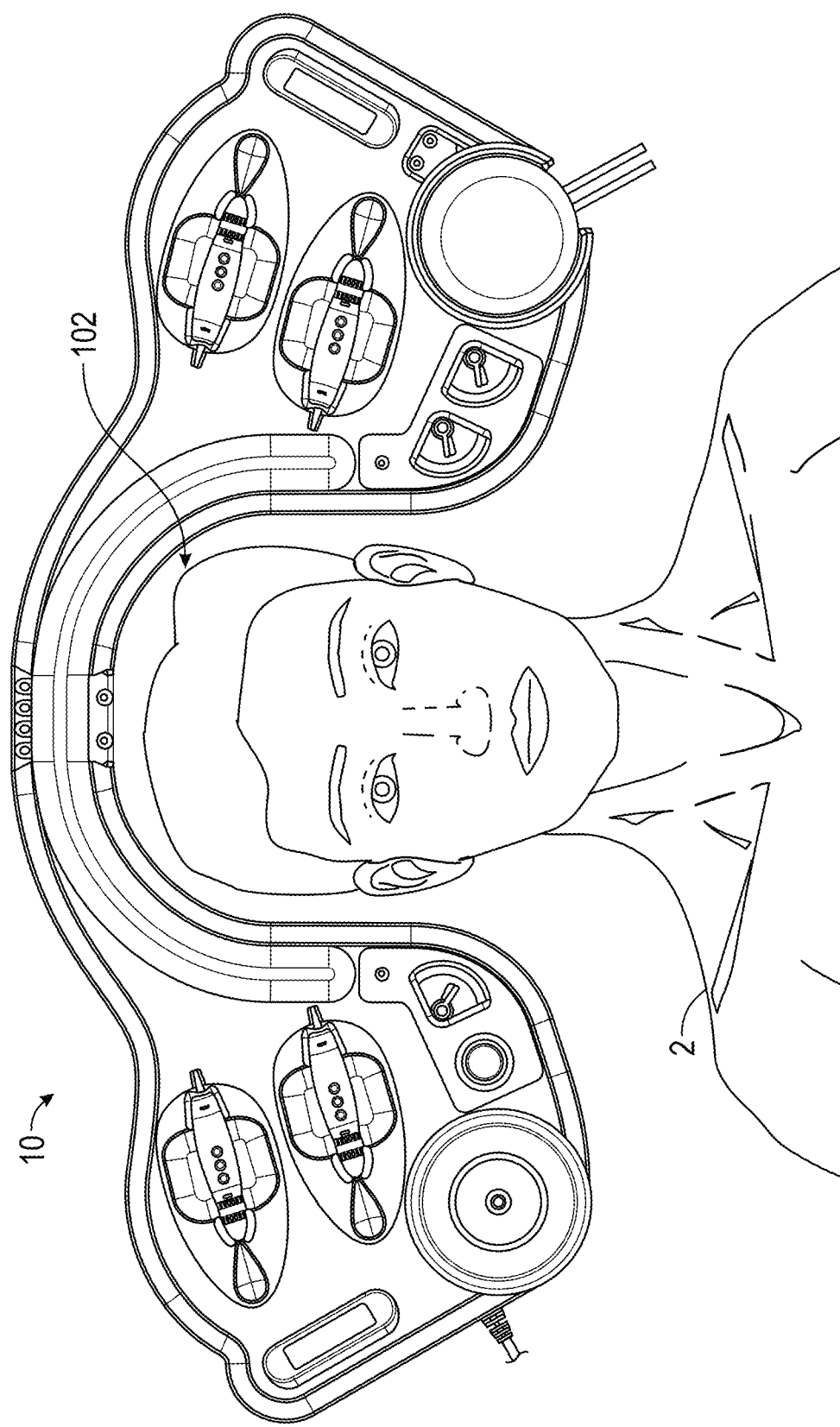
FIGS. 1A-1F illustrate an embodiment of a surgical tray that may be used for an ophthalmic surgical procedure.

Although several embodiments, examples, and illustrations are disclosed below, it will be understood by those of ordinary skill in the art that the invention described herein extends beyond the specifically disclosed embodiments, examples, and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

Some embodiments comprise a surgical tray or console that is located adjacent to the surgical site or nearby (e.g. adjacent to or around the patient's head during eye surgery). The tray may be U-shaped, L-shaped, or otherwise curved or angled to accommodate the anatomy of the surgical site. Some embodiments comprise a surgical tray that is mounted, secured, or otherwise attached to the patient gurney, patient headrest, surgeon's armrest, or surgical microscope through a temporary, semi-permanent, or permanent means. Some embodiments comprise a separate permanent or semi-permanent base unit that is securely mounted to the gurney, armrest, or other fixture such that the tray can be securely seated or positioned on the base. In some embodiments, the base replaces the surgeon's armrest or is mounted to the armrest and is therefore designed with the strength to support the surgeon's arms and hands. In other embodiments, the tray itself mounts directly to the fixture (armrest, gurney, microscope, etc.), for example using clips, straps, clamps, or other features to enable a secure mounting.

Modular or Hybrid Surgical Tray

In some embodiments, a modular or hybrid surgical apparatus or tray comprises one or more reusable components and one or more disposable components (which in some embodiments can be disposed of after a single use or in some embodiments can be disposed of after a limited number of uses) with at least portions of each contained within or in close proximity to the sterile work area. For example, one or more disposable components may comprise sterile components configured to be present within the sterile work area, and one or more reusable components may be configured to be at least partially contained within a disposable sterile component, encapsulated within a disposable sterile component, or otherwise isolated from the sterile work area (for example, using a sterile drape) while remaining in close proximity to the sterile work area.

In a typical use scenario, the one or more reusable components are not necessarily considered sterile, while the one or more disposable portions are provided in sterile packaging for use during a surgical procedure. A non-sterile reusable portion provides one or more functions in conjunction with the sterile portion of the system, but for one or more reasons, the reusable portion is not designed to be single use or disposable. For example, the reusable portion may include components that are or may be perceived to be too expensive, too large, too valuable, too wasteful, or too hazardous to dispose of after a single use. There are several benefits with a hybrid surgical tray system that integrates both disposable and reusable aspects, including but not limited to costs savings, reduced environmental impact, and higher sales margins.

The disposable portion(s) may in some embodiments comprise components of the system that are contaminated during use, wear out after a single use, or are otherwise not appropriate for extended use or multiple uses. These components may include (but are not limited to) fluidic tubing lines, fluidic components including fluidic connectors, stopcocks, check valves, filters, pumps or portions thereof (for example, pump tubing, peristaltic pump rotor and rollers, and/or the like), pressure and flow sensors, and/or the like; instruments that are inserted into the eye or other surgical site (or portions of the instruments, such as a removable needle); sterile drapes, bags, shells, or other coverings; trays, enclosures, work surfaces, instrument holders, and/or other structural elements of the surgical tray. In some embodiments, the disposables may also include electronics, electrical interconnects, and/or batteries. In some embodiments the disposables may include optical components, including but not limited to fibers, fiber bundles, light pipes, LEDs, lenses, and/or the like.

Reusable portion(s) may in some embodiments comprise components that are not contaminated during a surgical procedure (in some embodiments by the design of the hybrid/modular surgical apparatus) or can be sterilized or otherwise decontaminated after use. These components may comprise (but are not limited to) electronics, displays, power supplies, batteries, pumps or portions thereof (for example, motor and/or gear assembly), lasers, light sources, optical components, compressors, gas sources, enclosures, work surfaces, instrument holders, other structural elements of the surgical tray, and/or the like.

A significant challenge associated with a "multi-use" surgical tray system as described in this disclosure (such as, for example, a hybrid or modular system comprising both disposable and reusable components) is ensuring the design and the usage of the system adheres to proper sterile procedures and risk of contamination considerations. In particular, the interfacing requirements between the sterile disposable portion(s) of the tray and the non-sterile reusable portion(s) poses a challenge. In many current state of the art surgical systems, a reusable surgical assembly would be located some distance away from the sterile field and surgical site, with an extended length interface (for example, electrical cable, optical fiber, pneumatic/fluidic tubing, and/or the like) crossing the sterile and non-sterile barrier to connect the reusable assembly to a disposable assembly (for example, a surgical handheld instrument). Embodiments of the present disclosure, however, include both a non-sterile reusable portion and a sterile disposable portion within or in close proximity to the sterile work area.

One technique to accomplish this functional interfacing is a drape or cover that allows for interfacing of one or more types (for example, electrical, mechanical, optical, fluidic, and/or the like) through the drape or cover such that a sterile barrier between the sterile disposable portion and non-sterile reusable portion is maintained. An example of this functional drape technique is described in more detail below with reference to FIGS. 3A-3C.

Other techniques to accomplish this functional interfacing of the sterile and non-sterile components (or disposable and reusable components) within or in close proximity to the sterile work area, while adhering to standard sterile practices in a surgical operating room setting, are also disclosed herein. In some embodiments, a sterile disposable portion of the system (either alone or in combination with one or more other disposable or reusable portions) serves as a sterile aseptic container that encloses, covers, or otherwise protects or isolates the non-sterile reusable portion (or multiple non-sterile portions) such that a sterile barrier is always maintained during a surgical procedure. This can be preferable to the drape solution in that, in some embodiments, there is no need for a more costly or custom designed drape, and, in some embodiments, there is no need to penetrate, puncture, or otherwise pass something through the sterile drape, since, in some embodiments, the sterile disposable portion surrounds or encases the non-sterile reusable portion, and any required functional interfaces between the two or more portions can be made directly. In some embodiments, however, it can be desirable to combine both concepts, namely, utilizing both a drape having functional interfaces and a sterile component that at least partially isolates a non-sterile component.

In an example use scenario of a sterile component that isolates a non-sterile component from the sterile work area, an aseptic transfer procedure is used to unpackage and set up a multi-use surgical tray. A surgeon who has "scrubbed in" and is properly gowned (and therefore uncontaminated) would be present within the sterile work area, and an assistant (who is not considered to be sterile) would be present outside the sterile work area. The assistant would open and present a sterile packaged tray (disposable portion) to the surgeon, the assistant only touching the outer packaging (which is not considered sterile) and not the sterile tray itself. The surgeon would remove the disposable tray from the packaging without touching the outside of the packaging. In a single use tray embodiment (whereby the entire tray is disposed of after a surgical procedure, thus requiring no interfacing between a disposable and reusable portion) the tray would now be set up near the patient and the surgery would commence. In a multi-use or hybrid embodiment, the surgeon would then open or otherwise enable access to an aseptic enclosure that is part of the sterile tray into which the assistant would place the non-sterile reusable module. Various embodiments disclosed herein, for example FIGS. 12A-12C, 13A-13C, and 14A-14C, described in further detail below, illustrate such a multi-use or hybrid surgical tray that comprises an aseptic enclosure or cavity for insertion therein of a non-sterile reusable module.

In some embodiments, to reduce the size of a disposable portion of a surgical tray (which can, for example, help reduce overall cost and waste), the disposable portion may be designed to be large enough to contain (for example, to fully or partially encapsulate) the reusable module (containing functional elements), but other structural or supporting aspects of the tray that do not require functional interfacing to the reusable module can be designed to also be reusable and, for example, draped prior to a surgical procedure. The disposable portion may also in some embodiments comprise a relatively thin plastic or similar material (for example, injection molding or vacuum forming being preferred options for low cost and thin plastic features), with additional structural support being provided by the reusable portion upon which it rests or otherwise couples to. The disposable portion may in some embodiments function as a drape or sterile barrier (reducing or eliminating the need for a normal drape), or in some embodiments a standard sterile drape may be used on the reusable portion before the disposable portion is placed on the reusable portion.

Certain embodiments also divide the handheld instruments into reusable and disposable components. For example, the needle of an endoilluminator instrument or other instrument (for example, the instrument illustrated in FIG. 8A) that is inserted into the eye may be disconnected from the rest of the handpiece, allowing the contaminated portion (for example, the needle) to be disposed of while the rest of the handpiece (which, for example, may be undesirable to dispose of because of cost or other considerations) can be wiped down or otherwise sterilized, or alternately "bagged" or draped during the procedure to avoid contamination. Likewise the needle(s) and aspiration fluidic components of a handheld vitreous or tissue cutter, soft-tip extrusion instrument, or lens removal device may in some embodiments be configured to be disconnected from the rest of the handpiece for replacement with a new sterile component. Likewise a diathermy needle assembly may be configured to be disconnected from the rest of the handpiece to separate the disposable from the reusable element.

Functional Interfaces

Figure 2C:
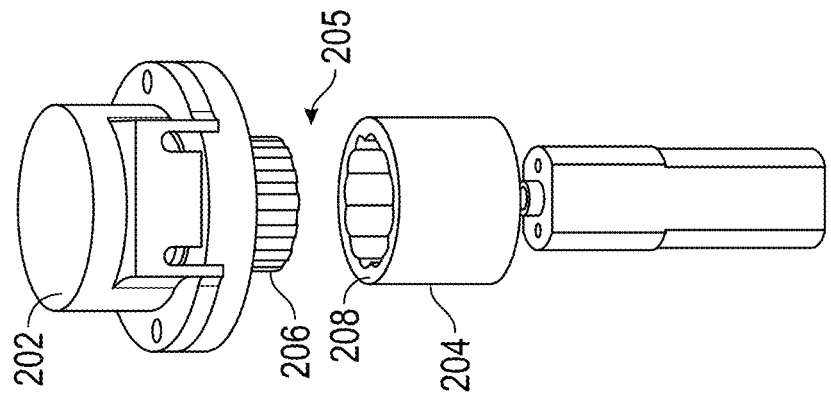
Figure 2B:
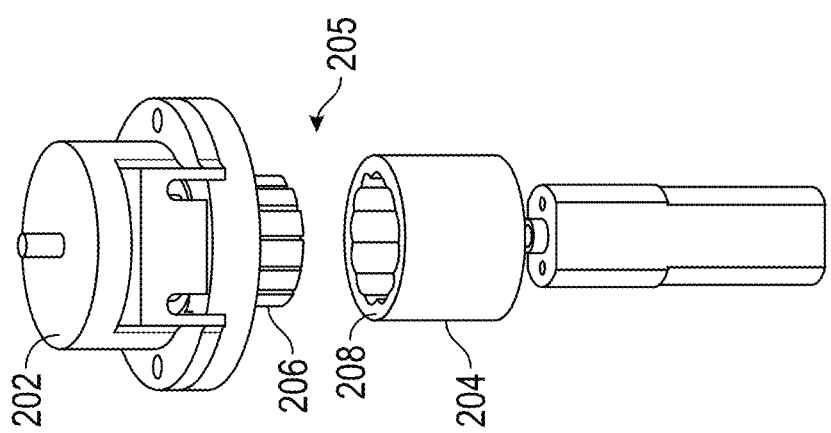
Figure 2A:
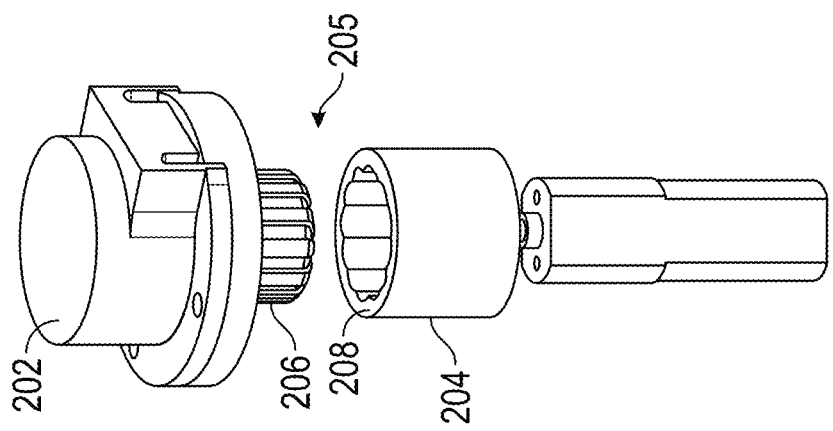
Figure 2F:
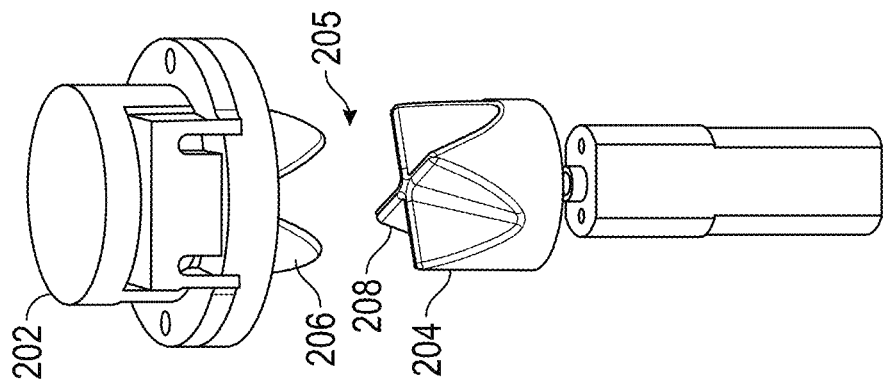
Figure 2E:
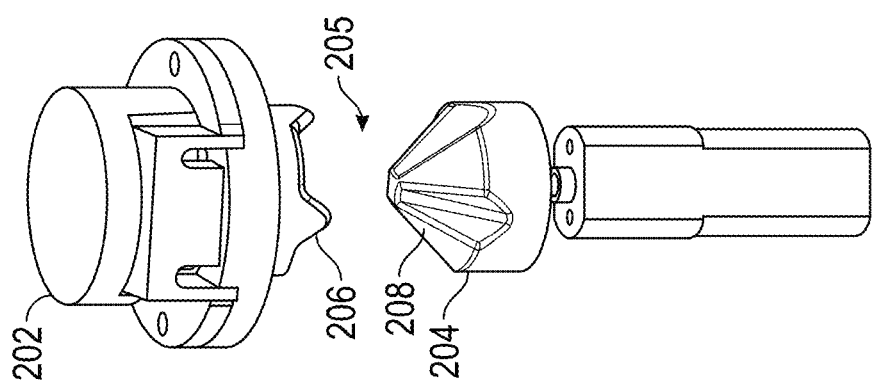
Figure 2D:
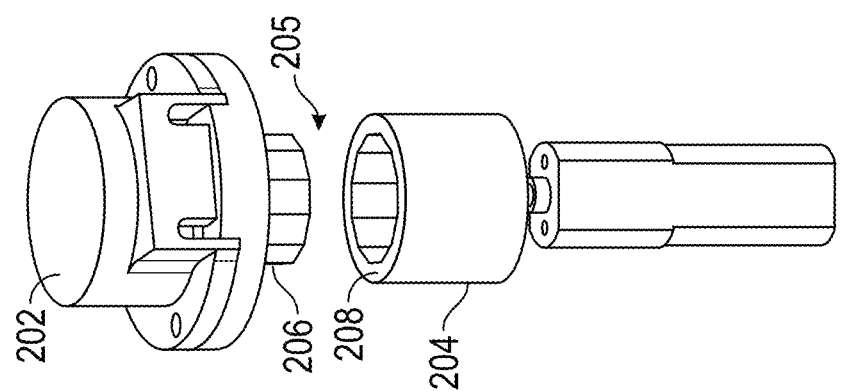
Figure 2I:
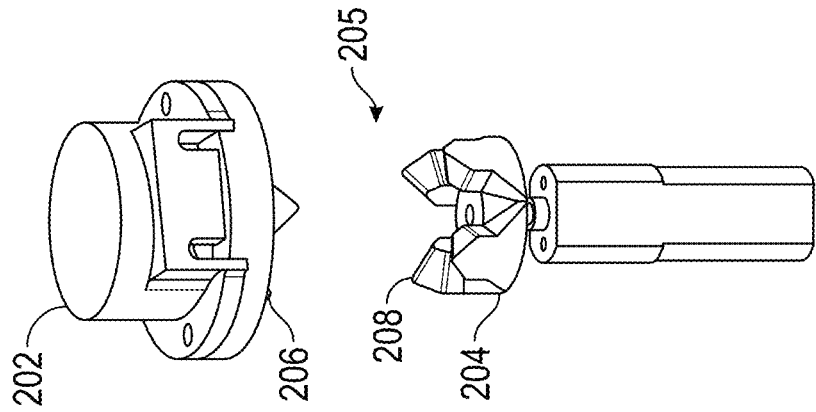
Figure 2H:
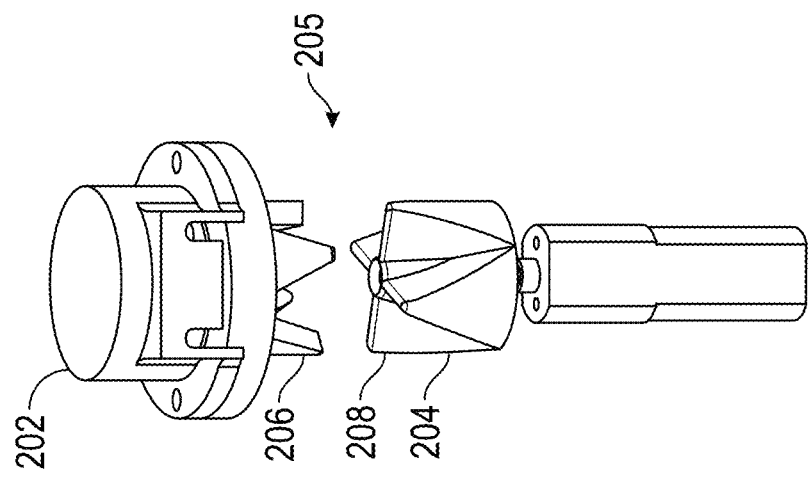
Figure 2G:
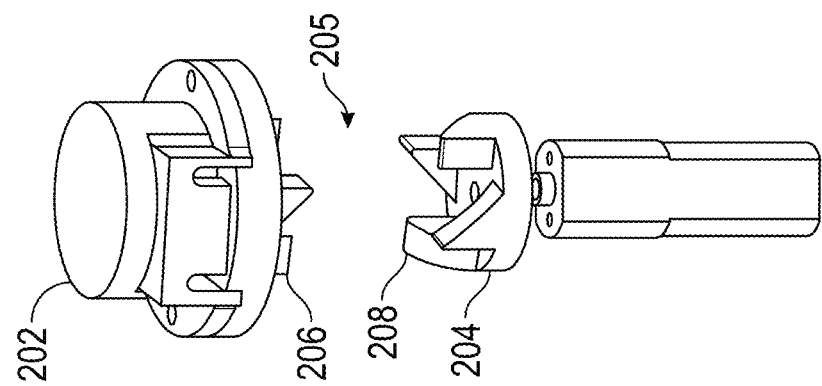
Figure 3A:
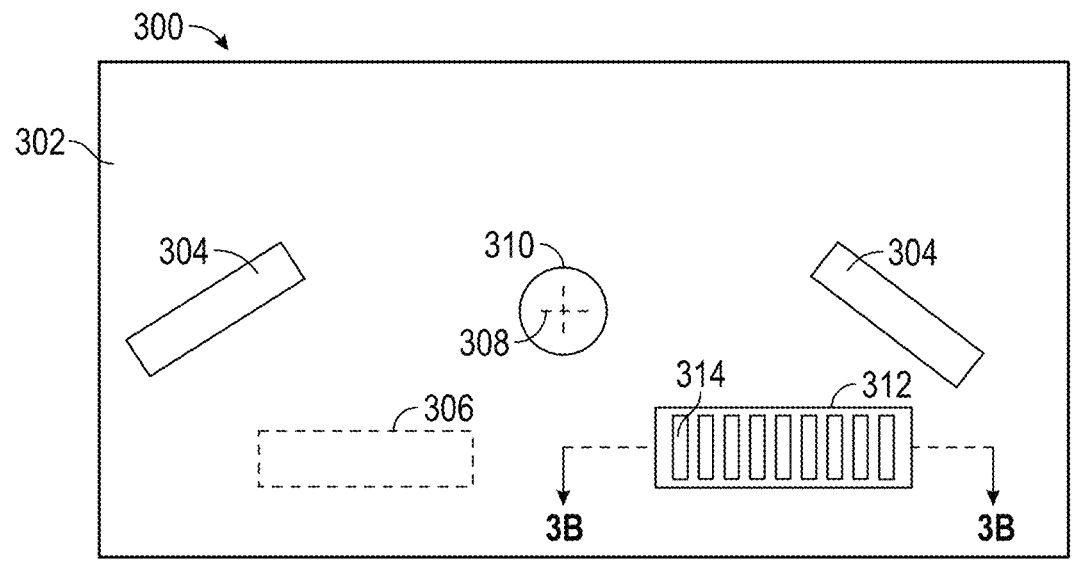
FIGS. 3A-3C illustrates embodiments of functional surgical drapes.
Figure 3B:
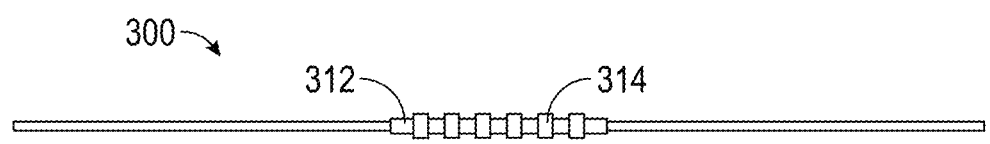
Figure 3C:
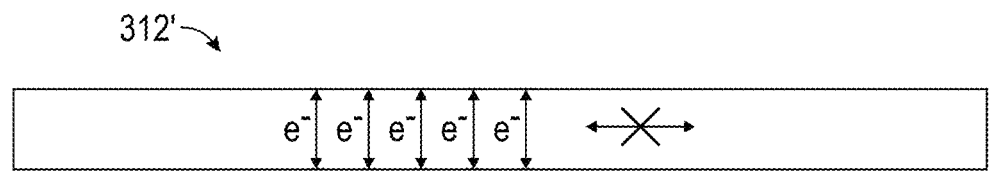

Various embodiments of surgical systems disclosed herein comprise one or more functional interfaces to enable a disposable and/or sterile component to functionally couple with a reusable and/or non-sterile component. Such a functional interface may, for example, enable the reusable and/or non-sterile component to provide power, light, fluids, electronic communications, and/or various other functions to the disposable and/or sterile component, enable the disposable and/or sterile component to perform one or more surgical functions. Several examples of functional connections or interfaces that may be utilized between a sterile component and a non-sterile component are disclosed herein. For example, FIGS. 2A-2K, as further described below, illustrate various mechanical rotational couplings. Such couplings may enable, for example, a reusable motor or gearbox to couple with a disposable pump head. FIGS. 3A-3C illustrate various functional interfaces in a custom surgical drape. The concepts illustrated may also in some embodiments be utilized in direct functional connections between a sterile component and a non-sterile component. FIG. 4C illustrates an example of an electrical functional interface that may be utilized with various embodiments, including, for example, embodiments that utilize the electrical interface to transmit electrical power and/or electronic communications. The embodiment illustrated in FIG. 4C illustrates an example of using mating electrically-conductive contacts to provide a pathway for electrical power and/or electronic communications. In some embodiments, however, power and/or communications are transmitted through non-contact or non-electrical means. For example, electrical power may be transmitted in some embodiments using a wireless and/or inductive coupling. Communications may in some embodiments be transmitted wirelessly, through an optical coupling, and/or the like. In some embodiments, a functional interface may comprise a transparent (or at least partially transparent) window, opening, or portion of a sterile component (for example, openings 408 shown in FIG. 4E) that enables a user of the system to see an electronic display, light, and/or the like of a reusable component. In some embodiments, an electrical functional interface comprises conductive connectors, an inductive interface, and/or the like. In some embodiments, an optical functional interface comprise light piping components and/or the like that enable transfer of light from a reusable component to a disposable component. In some embodiments, a functional interface comprises a fluidic connector to enable fluid to be transferred from or to a reusable component.

In some embodiments, an interface between a sterile disposable tray (or a component of the tray) and a non-sterile reusable component or module can be one or more of the following: electrical; mechanical; optical; fluidic; and/or the like. An electrical functional interface may in some embodiments comprise single or multi-conductor connectors (for example, as illustrated in FIG. 4C), springs or spring contacts, "gold finger" connectors, edge connectors, and/or the like. An electrical interface may also be accomplished in some embodiments through an inductive or wireless link. An electrical interface may also in some embodiments comprise single or multi-conductor cables or cords, jacks, plugs, and/or the like. An electrical interface (or other type of functional interface) may in some embodiments be designed such that electrical contacts on a disposable tray (or component thereof) and electrical contacts on a reusable module are aligned by mechanical features on the tray and/or the module. The reusable module may also in some embodiments connect via a wired or wireless interface with externally located components, such as a footpedal, externally located power supply, or separate surgical console.

Figure 18:
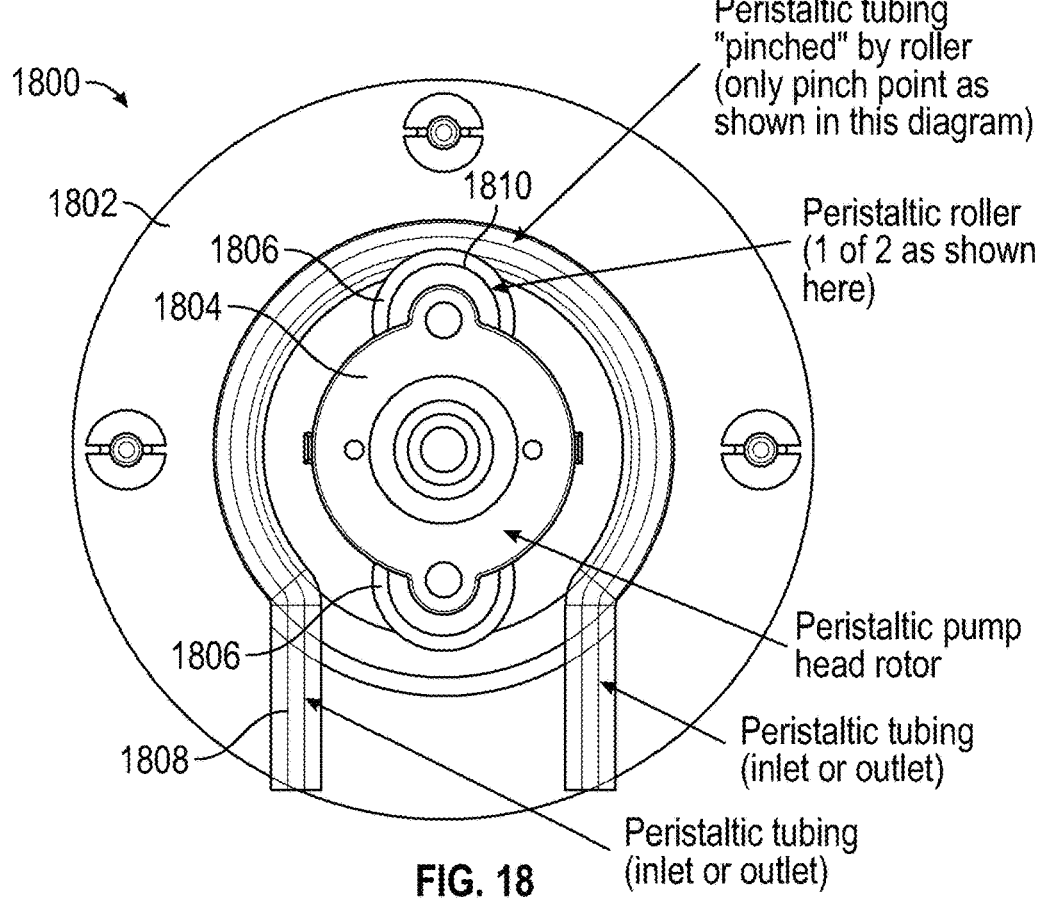
FIG. 18 illustrates an embodiment of a peristaltic pump head configured to accommodate gas sterilization.

A mechanical functional interface may in some embodiments comprise a coupling between a reusable motor and a disposable pump head (for example, comprising a peristaltic pump rotor, rollers, and tubing, as illustrated in FIG. 18) or reusable pump head and disposable peristaltic tubing (wherein, for example, a surgeon or other user would stretch or otherwise install single-use or limited-use peristaltic tubing over a reusable pump head). A mechanical interface may also in some embodiments comprise a motor or other actuator connected to a belt, chain, transmission coil, torque coil, rotary cable, and/or the like for actuating a non-adjacent system such as, for example, a handheld instrument. In some embodiments, the interface between the motor or actuator and its mating component may be a mechanical linkage or coupling such as a spline coupling, spider coupling, shaft coupling, etc. Some examples of rotary mechanical couplings are illustrated in FIGS. 2A-2K, as described below.

An optical functional interface may in some embodiments comprise a coupling between a reusable light source and a disposable fiber, fiber bundle, light pipe, and/or other waveguide. The light source may in some embodiments be an LED (in some embodiments, either RGB or white) or white light lamp for endoillumination, a treatment laser (for example, 532 nm or 1064 nm photocoagulation), or an imaging laser (for example, for optical coherence tomography). The interface may in some embodiments comprise lenses, mirrors, fibers, fiber bundles, prisms, light pipes and waveguides, and/or other optical elements to help guide and couple the light from the reusable portion to the disposable portion of the system.

A fluid functional interface may in some embodiments comprise an interface between disposable flexible tubing and a reusable sensor (for example, pressure sensor, flow sensor, fluid sensor, and/or the like) or between disposable flexible tubing and a pneumatic or fluidic source such as a compressor, compressed gas, pressurized liquid, pump, and/or the like. The interface may in some embodiments comprise fluid connectors that are mated when the reusable and disposable components are coupled, combined, or otherwise placed in a desired position with respect to each other.

In some embodiments, a sterile disposable tray (or a component thereof) may comprise an optical functional interface comprising a transparent or partially transparent material, for example to enable viewing by a user of one or more displays that are integrated into the reusable module. In some embodiments, the sterile disposable tray (or a component thereof) may comprise a thin, flexible, or otherwise pliable or compliant material, configured to enable the user to activate buttons located on the reusable module through the sterile disposable tray. In some embodiments, a sterile disposable tray may comprise thin vacuum formed plastic, and/or the like. In some embodiments, portions of the transparent material may be painted, dyed, or otherwise made opaque, such that only a portion of the material (such as at the optical interface) remains transparent in use.

Any of the functional interfaces disclosed herein may be configured or positioned to be automatically engaged or placed in a desired position or configuration when the reusable component is coupled to the disposable component (or otherwise placed in a desired position relative to the disposable component). Alternatively, one or more functional interfaces may be configured to be manually engaged by a user before or after the reusable component is coupled to the disposable component.

In some embodiments, a reusable portion(s) and/or disposable portion(s) may comprise features that help align, register, or otherwise position themselves to aid in mating or interconnecting the portions and/or their functional interfaces. For example, one or both portions may include features to help align or connect electrical contacts or interconnects, mechanical interconnects (for example, between a reusable motor shaft and disposable peristaltic pump rotor, cam, and/or the like, or between a reusable pump rotor and rollers and disposable peristaltic tubing), pneumatic or fluidic interconnects (for example, to connect disposable portions to reusable sensors, pneumatic or fluid sources, compressed gases, peristaltic pumps, venturi pumps, and other pumps, and/or the like) and/or optical interconnects (for example, to connect disposable portions to reusable light sources, lasers, and/or the like). Magnets may also be used in some embodiments to align or secure different components of the system. A reusable module may in some embodiments be powered on or otherwise activated or enabled automatically or have a means to determine that it is properly "docked" when installed within or mounted to (or otherwise coupled with) the sterile disposable tray (or a component thereof).

Surgical Tray Console

Figure 1C:
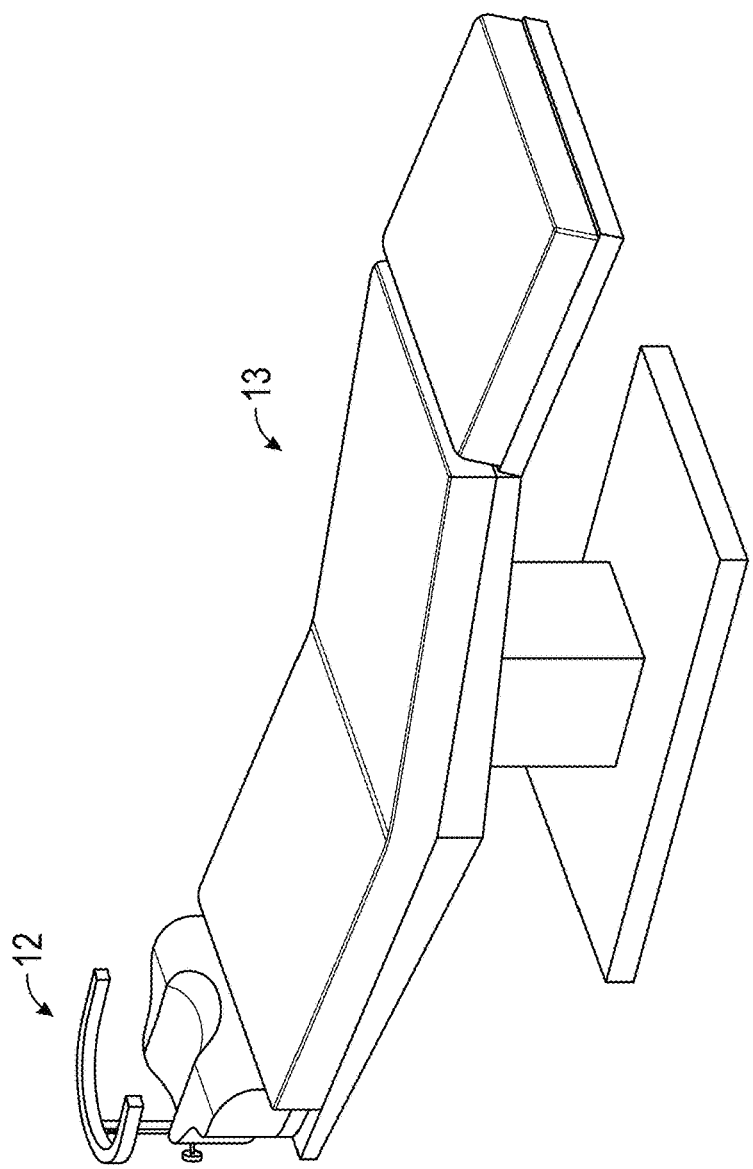
Figure 1B:
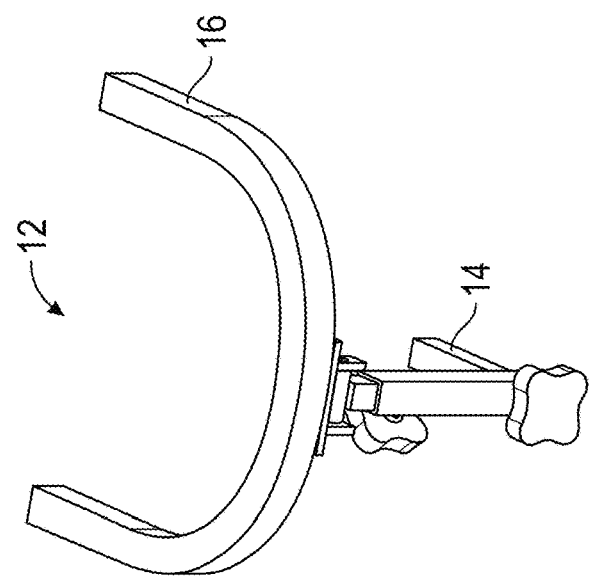
Figure 1D:
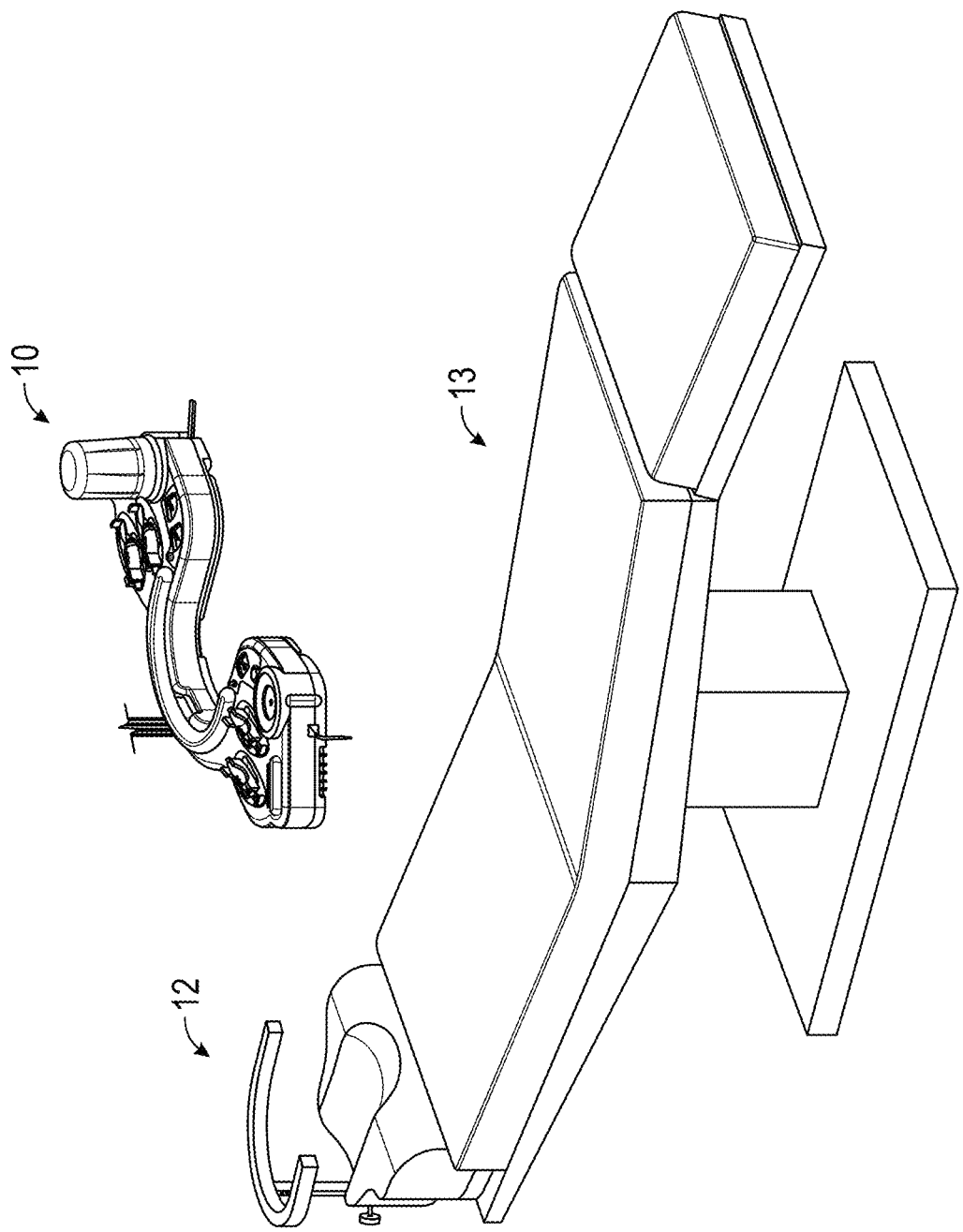
Figure 1E:
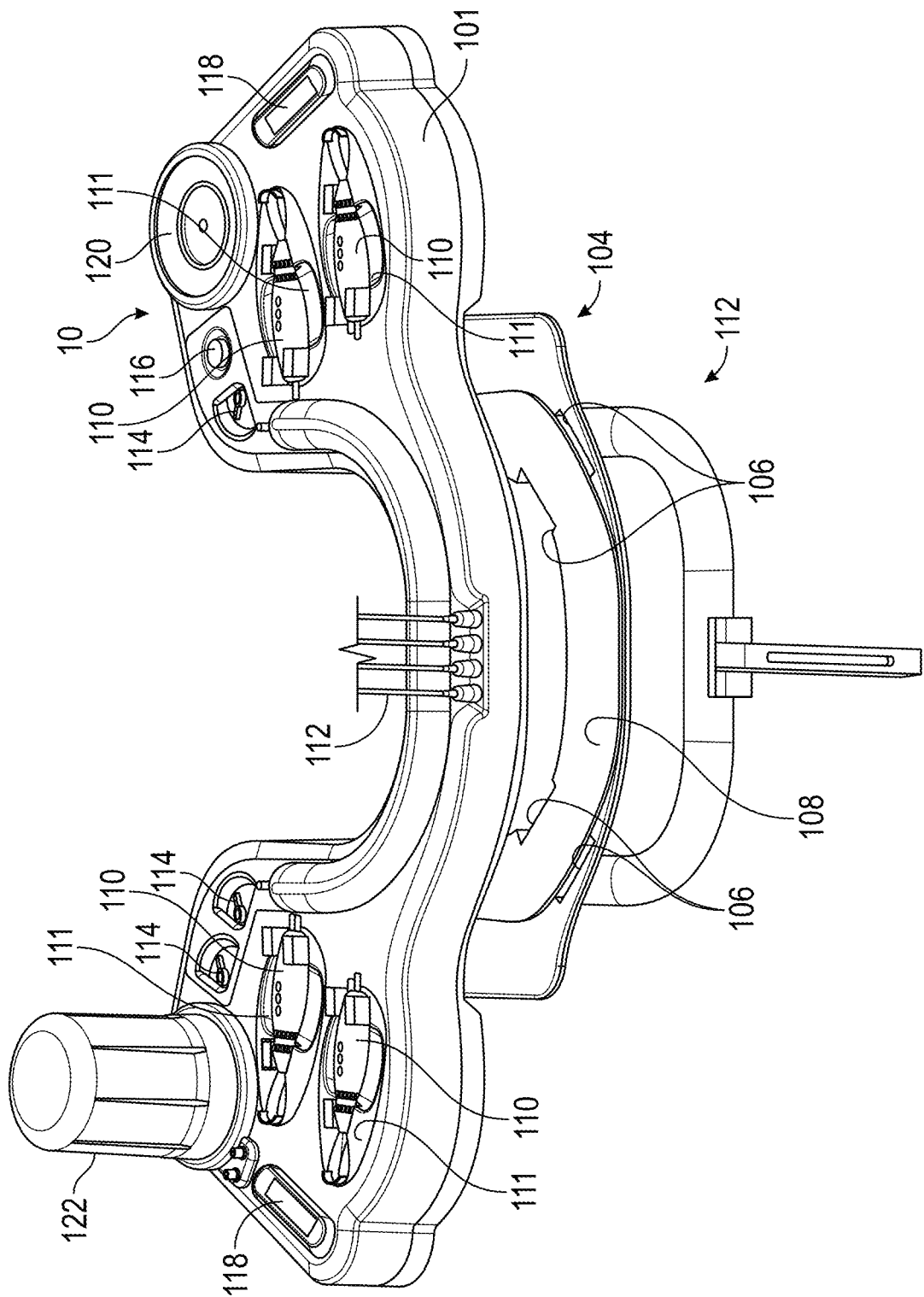

FIGS. 1A-1F illustrate an embodiment of a surgical tray 10 that may be used for an ophthalmic surgical procedure. FIG. 1A illustrates an overhead or top view of the surgical tray 10 in use with a patient 2. In this embodiment, the surgical tray 10 comprises a void or cutout 102 shaped to be positioned around the patient's head. FIGS. 1B-1F further illustrate the surgical tray 10 and one way the surgical tray 10 may be mounted to a surgical table, chair, or gurney 13. In some embodiments, a surgical table 13 as shown in FIG. 1C comprises a support 12, such as a wrist support, shown in more detail in FIG. 1B. The support 12 comprises a support bar 16 and an end 14 configured to connect to a head of the surgical table 13. As shown in FIG. 1E, in some embodiments, a surgical tray 10 may comprise a top portion 101 configured to mate with a base portion 104. In the presently illustrated embodiment, the base 104 is desirably intended as a mounting structure to enable efficient and configurable mounting of the top portion 101 to the table 13. In some embodiments, as further described herein, a base portion may comprise more functional features, such as, for example, a motor and/or pump, electronics, and/or the like. The base 104 may comprise one or more slots 106 or other features configured to enable the base 104 to attach or couple to the support 112 of the table 13. In some embodiments, straps are used to hold the base 104 to the support 112, with the straps passing through the slots, grooves, or recesses 106. In some embodiments, the surgical tray 10 comprises a pad 108 positioned on top of the base 104 to, among other things, help remove any slack between the top portion 101 and the base 104 to maintain a sturdier connection between the top portion 101 and base 104.

Figure 1F:
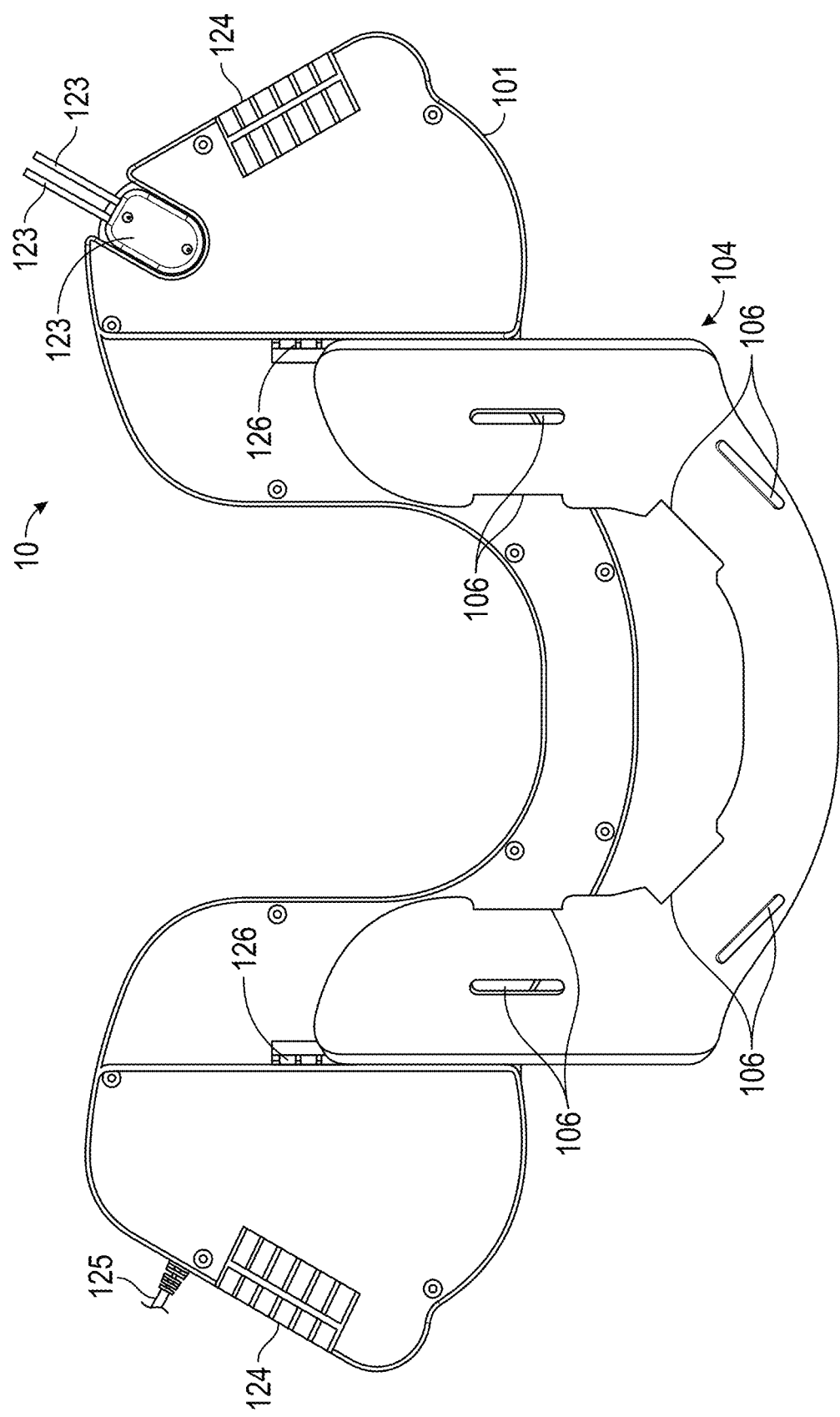

As can be seen in FIG. 1F, in some embodiments, a surgical tray is configured to slidably engage a base. In this embodiment, the surgical tray top portion 101 comprises latches 126 which engage the base 104. In some embodiments, levers or switches or handles 124 enable a user of the surgical tray 10 to selectively engage or lock the top portion 101 in position with the base 104. In some embodiments, the latches 126 are adjustable to enable the top portion 101 to lock in a plurality of positions, such as to accommodate patients of different sizes and/or a preference of the user. For example, in the embodiment illustrated in FIG. 1F, which is a bottom view of the surgical tray 10, the top portion 101 is illustrated locked in place in a position approximately halfway to a full engagement position.

FIG. 1E, which is an exploded view of the top portion 101, base 104, and support 112, illustrates several features of the surgical tray 10. For example, the surgical tray 10 comprises one or more handpieces or surgical tools 110, in this embodiment four handpieces 110. The handpieces 110 may comprise one or more tools for performing surgical functions, such as, for example, vitreous cutting, diathermy or electrocautery, illumination, and/or the like. In some embodiments, the handpieces 110 are tethered to the top portion 101 through cables or tethers 112. In some embodiments, a cable or tether 112 comprises one or more features, such as, for example, power transmission, electronic communication, communication through other methods, such as pneumatic or optical, and/or the like.

The surgical tray 10 further comprises a plurality of recesses or storage structures 111 configured to engage the handpieces 110 to hold the handpieces in place until they are needed and/or between surgical procedures. The surgical tray 10 further comprises a plurality of controls 114 to control a plurality of functions of the surgical tray 10, such as, for example, fluid infusion, oil infusion, air infusion, and/or the like. The surgical tray 10 further comprises a power button 116 configured to operate power to one or more devices of the surgical tray 10. One or more displays or indicators and/or light sources 118 of the surgical tray 10 enable information to be communicated to, for example, a user or surgeon during a surgical procedure. In some embodiments, one or more displays or indicators 118 may be located separate from the surgical tray 10, for example on the microscope or on the wall and connected to the tray via a wired or wireless connection. The surgical tray 10 further comprises a fluid reservoir receiver 120 and a balanced salt solution (BSS) bottle, container, sterile enclosure, or other holder 122. In this embodiment, a motor may be configured to be removable and/or removably coupled to a pump head 123, shown in FIG. 1F. The pump head further comprises pump input and/or output tubes 123. In some embodiments, it may be desirable to make a motor removable from the surgical tray 10 and/or pump head 123, so that, for example, a relatively expensive and/or higher-quality motor may be utilized, while a rest of the surgical tray 10, including the pump head 123, is disposable after a single procedure or a predetermined number of procedures. Various embodiments of coupling mechanisms that may be used to couple the motor to the pump head 123 are described in further detail below with reference to FIGS. 2A-2K.

In some embodiments, one or more surgical trays disclosed herein, such as, for example, the surgical tray 10 illustrated in FIGS. 1A-1F, may comprise one or more features similar to and/or one or more features that may operate similarly to those disclosed in U.S. Pat. No. 8,568,391, entitled STERILE SURGICAL TRAY, which is hereby incorporated by reference herein in its entirety.

Different embodiments may comprise removable and/or non-removable electronics that control the functions of the tray. The electronics may comprise one or more microcontroller(s), microprocessor(s), microelectronics, and/or the like; the electronics may include any of a variety of sensors, including but not limited to pressure, vacuum, flow, temperature, light intensity, voltage/current/power, and inertial measurement. The electronics may also be designed to be low cost and therefore disposable after a single use or a limited number of uses. The electronics may comprise software or hardware features that prevent the use of the electronics beyond what was intended by the manufacturer. For example, the electronics may become inoperable after a single use to prevent reuse which can pose a safety risk to the patient (for example, because the system is no longer sterile) and protect sales revenue for the manufacturer. The electronics may also in some embodiments be designed to work for a limited number of uses, a limited amount of time, or until a pre-defined expiration date. For example, this would be useful to prevent the use of the system beyond what is considered reliable (for example, certain components may have a limited number of uses before the probability of failure becomes a risk, or the efficacy or sterility of certain components of the system may have a limited shelf-life). This could also be used in a subscription-style sales model, wherein the surgeon or hospital can purchase additional credits to use the system for additional surgical procedures or add/unlock additional functionality of the system. Some embodiments may also utilize non-electronic and non-software means of limiting reuse; for example the handpieces and/or tray components may be manufactured from materials that do not survive autoclave sterilization.

A tray in some embodiments may incorporate an internal power supply or transformer and rectifier that converts AC wall power to lower voltage DC. The tray may alternatively utilize a power supply separate from the tray (e.g. a "wall-wart" transformer or external brick power supply). The tray may also be powered by one or more single-use (primary) batteries (for example, alkaline, lithium manganese, or other chemistry) or rechargeable (secondary) batteries (for example, Li-ion, Li-Poly, NiMH, NiCd, or other chemistry). The batteries may, in some embodiments, be configured as a self-contained battery pack that can be removed from the tray itself. The tray may also derive power (electrical, pneumatic, and/or otherwise) from a separate console system to which the tray is coupled or from the surgical microscope.

In embodiments that comprise a reusable permanent or semi-permanent base that is separate from the tray itself, the base may be designed to incorporate any one or several of the following for benefits that include reducing the manufacturing cost of the tray, reducing waste, and using higher quality reusable components: electronics; displays; sensors (e.g. pressure, flow); power supply; one or more primary or secondary batteries or battery packs; pumps or components and sub-assemblies of a pump (e.g. the motor and drive circuitry) for example to be used for infusion, aspiration, and/or driving a pneumatic or hydraulic instrument; handpiece drive motors (e.g. for moving or rotating a transmission cable or torque coil connected to a vitreous cutter or other mechanical instrument); endoillumination light source; photocoagulation laser. The base and tray may implement features that allow the tray to be temporarily but reliably attached to the base, as well as to adjust or otherwise translate the position of the tray, for example to accommodate different patient geometries. In yet another embodiment, some or all of these features may be located in a footpedal (or more than one footpedal) that is used to control the functions of the surgical tray and handpieces. The footpedal may be tethered to the tray and/or handpieces through electrical connections (e.g. a cable assembly), pneumatic/hydraulic connections (e.g. tubing), optical connections (e.g. one or multiple optical fibers for broadband or narrow wavelength light that can be used for illumination, laser therapy, imaging, etc.), and mechanical linkage connections (e.g. transmission cables or torque coils for transferring the motion of a motor, piston, etc. located in the footpedal enclosure to the tray or handpieces.) In related embodiments, the footpedal may contain some of these elements but connect to pumps (e.g. for infusion and/or aspiration) that are located in the base unit or tray such that the tubing lengths between the pump and the patient are minimized.

In embodiments with pump motors and/or handpiece drive motors in a separate base, the pump motors may couple to the pump heads in the tray and the drive motors may couple to the transmission cable or torque coil via spline couplings, shaft couplings, or similar that are aligned and engage when the tray is mounted or positioned on the base. FIGS. 2A-2K illustrate a variety of embodiments of couplings or coupling mechanisms 205 that may be configured to enable removable coupling of a motor output shaft and/or torque transfer mechanism 204 to a pump head 202. The embodiments illustrated herein comprises a pump-side coupling portion 206 and a motor-side coupling portion 208. In the embodiments illustrated in FIGS. 2A-2C, the pump-side coupling portion 206 comprises a male spline configured to couple with a female spline of the motor coupling portion 208. The male splines 206 are configured to slidably coupled with the female splines 208 to enable a torque to be transferred from the motor to the pump head 202. FIG. 2D illustrates an embodiment of a coupling 205 wherein a male portion 206 and a female portion 208 comprise mating flats, similar to a hex head bolt and socket that enable transfer of torque therethrough. FIGS. 2E-2K illustrate a variety of embodiments wherein alternating peaks and voids of a pump-side portion 206 engage alternating peaks and voids of a motor-side portion 208 to enable transfer of torque therethrough. Various other removable torque transfer couplings may alternatively be used. In other embodiments, the pump motors and pump heads are not readily separable and instead the pump tubing is separable from the pump head.

Functional Sterile Barrier

In some embodiments, an ophthalmic surgical system comprises a custom sterile barrier, such as a drape, that can be used to drape the non-sterile permanent base to create a sterile barrier before placing the tray on the base. The drape may in some embodiments be form-fitted to the base and tray. The drape may in some embodiments comprise one or more functional features, such as one or more features enabling light, electricity, a mechanical device, and/or the like to pass therethrough. For example, the drape may comprise one or more transparent windows to enable displays in the base to be viewed. In some embodiments, the drape may comprise perforations that are broken or pierced when the tray is mounted to the base to enable electrical, mechanical, and/or fluidic/pneumatic connections to be made between the tray and the base. In some embodiments, the drape may lack any perforations but nonetheless be punctured or perforated in specific areas when the tray and the base are mated. In some embodiments, the tray and the base may form a seal around the area to be perforated before the perforation occurs to ensure that a sterile barrier is maintained during the setup process. In some embodiments, the drape may have integrated electrical contacts such that one or more electrical connections can be made between the base and the tray without breaking or piercing the drape or otherwise compromising the sterile barrier. These electrical contacts may be formed, in some embodiments, by integrating separate contacts into the drape material, or the drape material itself may be made of a material or incorporate a material in the appropriate regions that is anisotropically conductive, such that electrical current can flow through the thin drape material but multiple adjacent current paths do not interact with each other. In other embodiments, electrical power is wirelessly transferred through the drape via inductive coupling of two antennas located on opposite sides of the drape or via similar wireless power transmission methods.

FIG. 3A illustrates a top view of an embodiment of a drape 300 incorporating a plurality of functional features. Drape 300 comprises a sheet of flexible material 302 configured and/or shaped and/or sized to be draped over, for example, a base portion of a surgical tray and or a patient's head to enable maintaining a sterile barrier during surgery. In some embodiments, the drape is configured to be positioned at least partially between a base portion and a top portion of a surgical tray, such as is illustrated in FIG. 4F, as further discussed below. In the embodiment illustrated in FIG. 3A, the drape 300 is illustrated as a rectangle for simplicity; however, in other embodiments, the drape 300 may be shaped differently and/or custom-fitted such that the drape is able to be positioned in a predetermined configuration over at least a portion of a surgical tray.

The drape 300 comprises two windows 304, such as transparent regions positioned to enable a user to view one or more displays of a surgical tray therethrough. For example, the windows 304 may be positioned to enable a user to view the displays 118 illustrated in FIG. 4A, as further described below. The drape 300 further comprises a perforated area 306 comprising a perforation enabling the perforated area 306 to be breached and/or removed when the drape 300 is placed into position, enabling a functional device to pass therethrough. For example, an electrical connection may pass therethrough, a mechanical coupling may pass therethrough, a pneumatic and/or hydraulic coupling may pass therethrough, an optical coupling may pass therethrough, and/or the like. The drape 300 further comprises an alternative perforation configuration 308. The perforation 308 comprises a perforation in the shape of a cross, such as to enable a tubular or other functional member to pass therethrough.

In some embodiments, one or more functional areas of a drape 300 comprise a sealing portion 310, shown in FIG. 3A as a circular area around the perforation 308. The sealing portion 310 may comprise, for example, a material that enables or aids in forming a sterile seal between, for example, a top portion and bottom portion of a surgical tray prior to the perforation 308 being breached or torn or opened. In some embodiments, the sealing portion 310 may comprise a resilient material, such as a rubber. In some embodiments, the sealing portion 310 comprises a ring of material (or otherwise shaped) that is stiffer than the primary drape material 302.

In some embodiments, the drape 300 comprises an electrical contact portion or region or block 312. The electrical contact portion 312 in this embodiment comprises a plurality of electrical contacts 314, such as electrically conductive material that enables a mating contact on one side of the drape 300 to be in electrical communication with a mating contact on an opposite side of the drape 300. FIG. 3B illustrates a cross section of the electrical contact portion 312. It can be seen in FIG. 3B that, in this embodiment, the plurality of electrical contacts 314 pass from one side of the drape 300 to another side of the drape 300, thus enabling electrical current to pass also from one side of the street 300, such as a sterile side, to another side of the drape 300, such as a nonsterile side.

FIG. 3C illustrates a cross section of an alternative embodiment of an electrical contact portion 312'. In this embodiment, the electrical contact portion 312' comprises an anisotropically conductive material that, as illustrated schematically in FIG. 3C, enables electrical current to pass in one direction, such as from one side of the drape 300 to another side of the drape 300, but not in a transverse or perpendicular direction. Accordingly, a plurality of electrical contacts of a top portion of a tray may be configured to be in electrical communication with a plurality of electrical contacts of a bottom portion of a surgical tray through the electrical contact portion 312' without requiring a plurality of discrete electrical contacts on the electrical contact portion. This may, among other things, enable reduced manufacturing costs and/or an increased tolerance of positioning of the drape with respect to the surgical tray.

Modular Surgical Tray System

In some embodiments, a surgical tray as disclosed herein may be a modular system, with a base or reusable portion that is configured to have one or more modules coupled to it. In some embodiments, a base portion is configured to be reusable, at least for a predetermined number of procedures and/or length of use, while one or more in embodiments of modules are configured to be disposable, such as after a single use. In some embodiments, a module surgical tray system comprises a disposable top tray portion that couples to a reusable bottom tray portion. In some embodiments, a modular surgical tray system comprises a reusable tray having one or more locations for insertion of one or more functional modules, such as a motor/pump module, a fluid reservoir receiver module, a power adapter module, a modular tool insert comprising one or more handpieces, and/or the like.

In some embodiments, a reusable portion of a modular surgical tray system, such as a base portion, comprises one or more reusable functional units configured to couple to, communicate with, and/or the like, one or more disposable functional units of one or more modules. For example, in some embodiments, a reusable base portion may comprise a motor that is configured to couple with a disposable pump housing of a disposable module portion. In some embodiments, a reusable portion, such as a base portion of a surgical tray system or assembly, may comprise an electrical processing unit configured to control operation of one or more surgical tools and/or to detect inputs or conditions from one or more controls and/or surgical tools of a disposable portion. In some embodiments, a modular surgical tray system comprises a custom surgical drape, such as described above with reference to FIGS. 3A-3C, that is configured to be positioned between a reusable or base portion and a disposable or top portion or module.

Figure 4A:
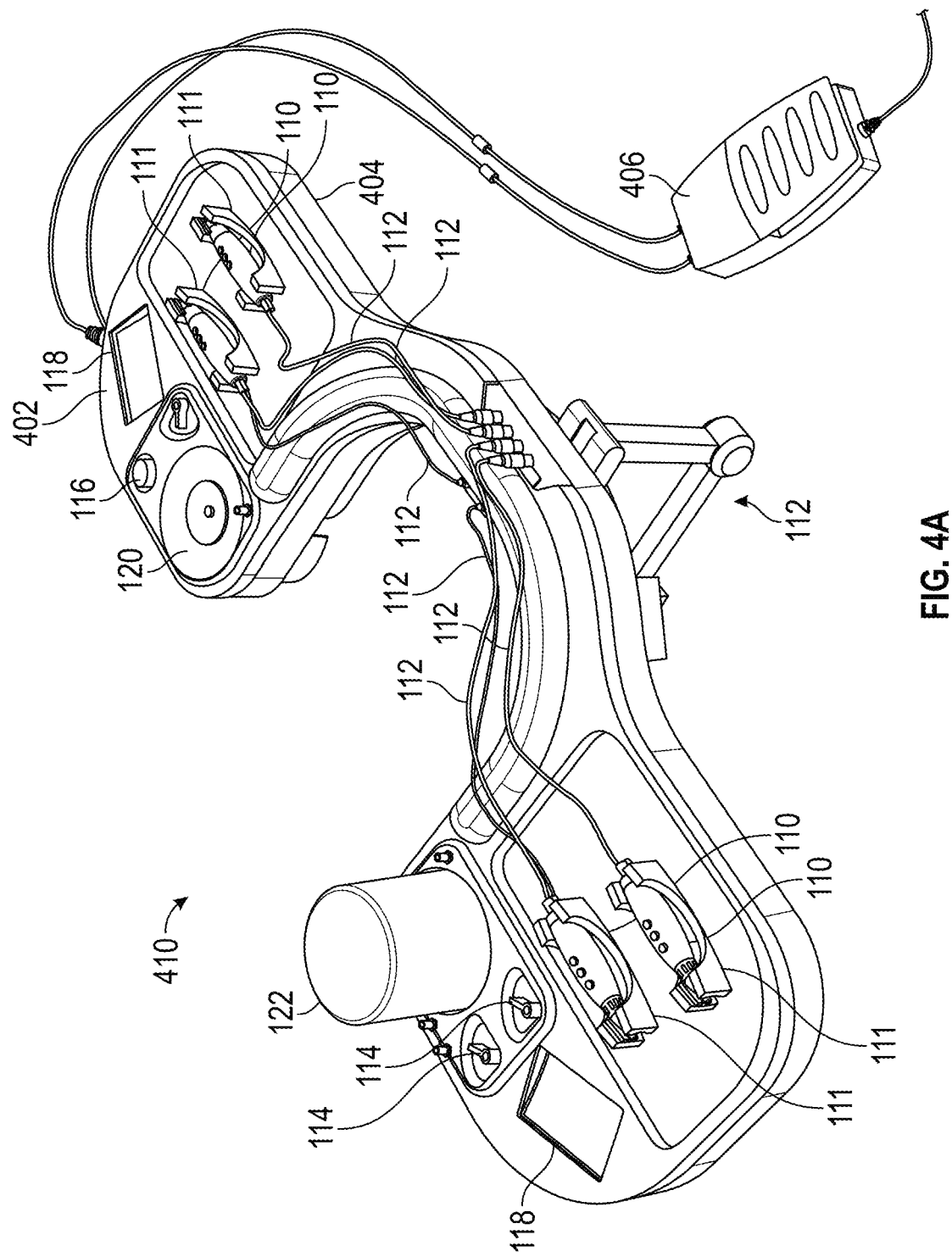

FIG. 4A illustrates a perspective view of an embodiment of a modular surgical tray system comprising a top or disposable portion 402 coupled with a bottom or reusable portion 404. The bottom portion 404 is coupled to a support 112, such as a support at a head of a surgical table. The bottom portion 404 may be configured to mate with the support 112 in a variety of ways, such as, for example, straps that pass through slots, such as the straps 412 illustrated in FIG. 4B. The surgical tray 410 illustrated in FIG. 4A comprises a plurality of features similar in design to those of other embodiments described herein, such as, for example, a plurality of handpieces 110, storage or support locations for the handpieces 111, a plurality of tethers or cables 112 connecting the handpieces 110 to, in this embodiment, the bottom portion 404, a plurality of controls 114, a power button 116, two displays 118, a fluid reservoir receiver 120, and a BSS bottle 122. The embodiment illustrated in FIG. 4A additionally comprises a foot pedal 406 tethered to or in communication with the bottom portion 404 to enable control of one or more features of the surgical tray system 410.

Figure 4B:
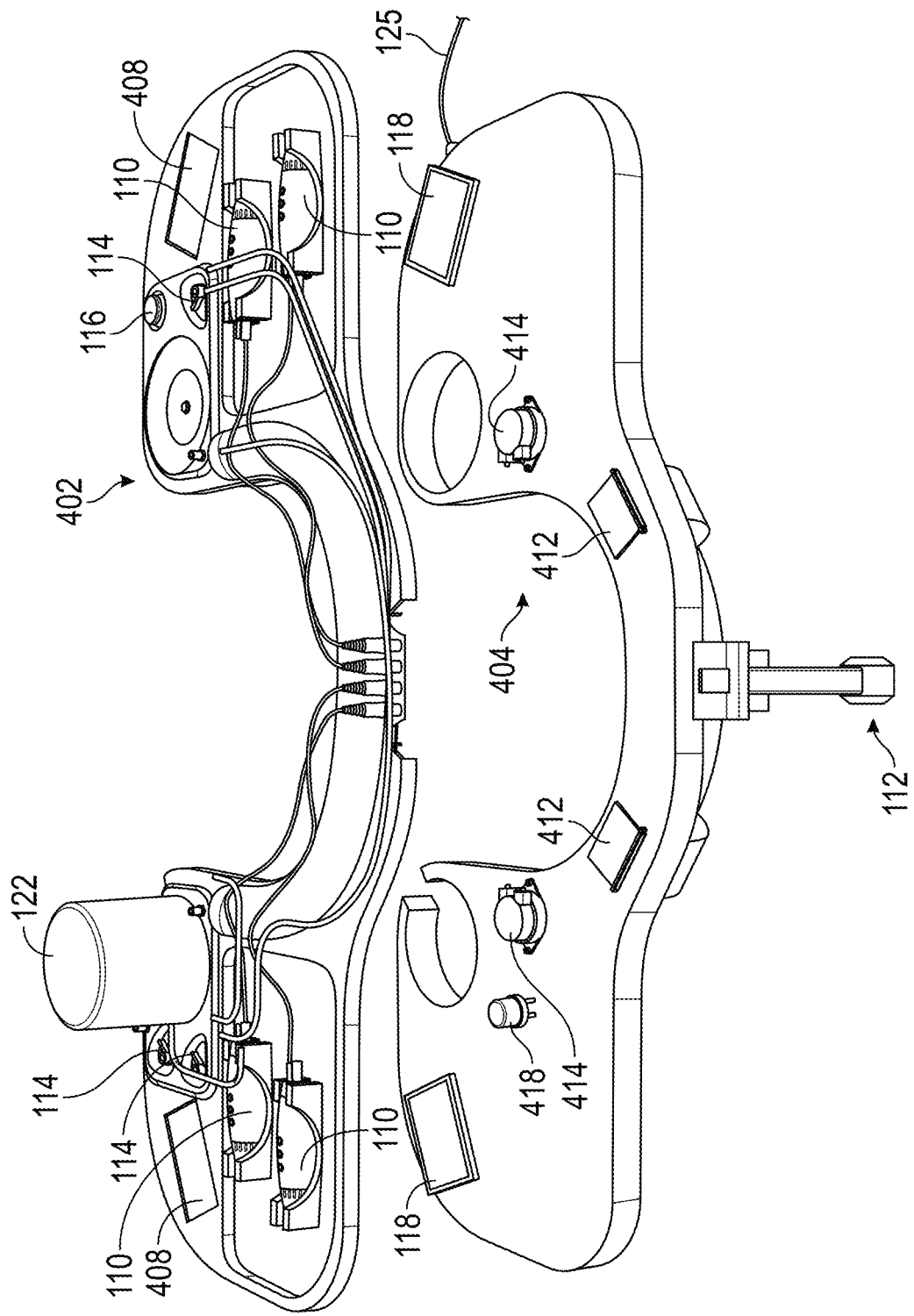
Figure 4C:
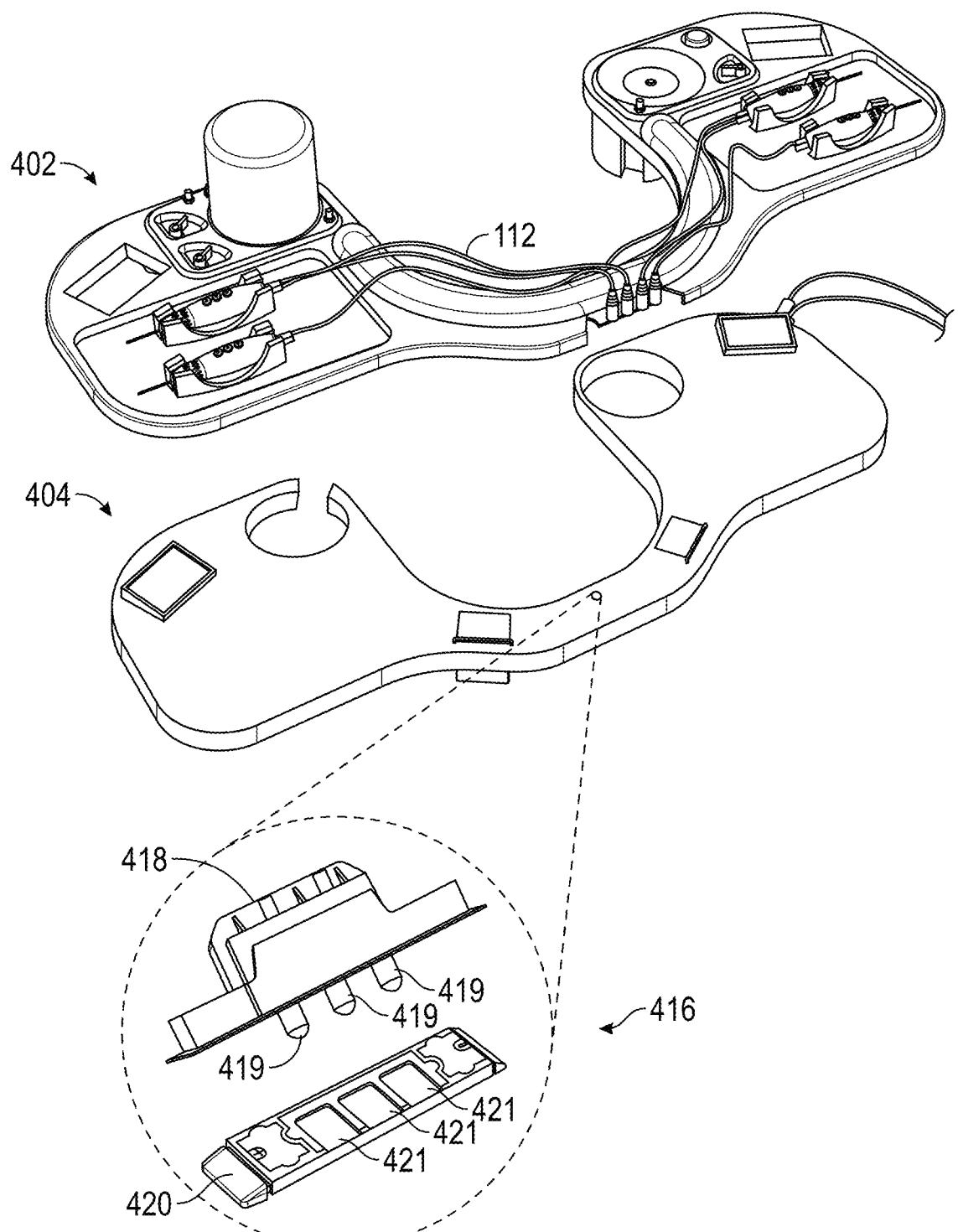

FIG. 4B illustrates an exploded view of the surgical tray system 410 showing the base portion 404 attached to the support 112, but the top or disposable portion 402 not yet coupled to the base portion 404. In this embodiment, some functional features of the base portion 404 are illustrated, including the displays 118, a light source 418 (in this embodiment an LED and in other embodiments the light source can be a laser, halogen lamp, or the like), and two pumps 414. FIG. 4C illustrates another example of a functional feature that enables electrical connection between the top portion 402 and the base portion 404. In this embodiment, the tethers or cables 112 are connected to a top electrical connector 418 that is part of or coupled to the disposable tray portion 402. The top connector portion 418 comprises a plurality of electrical contacts or pins 419 protruding therefrom and configured to engage mating electrical contacts 421 of a bottom connector portion 420 that is part of or coupled to the base portion 404. Accordingly, in this embodiment, the handpieces may be automatically connected to electronics or other features of the base portion 404 upon coupling of the top portion 402 to the base portion 404. In other words, a user of the system may not have to individually plug-in each handpiece after positioning the surgical tray top portion 402 over the base portion 404. In some embodiments, such a configuration can be advantageous to enable, for example, more expensive and/or durable components to be part of or coupled to the base or reusable portion 404, while the top or disposable portion 402 may be supplied as a single sterile assembly ready to be utilized for a single surgery and disposed of after surgery.

Figure 4D:
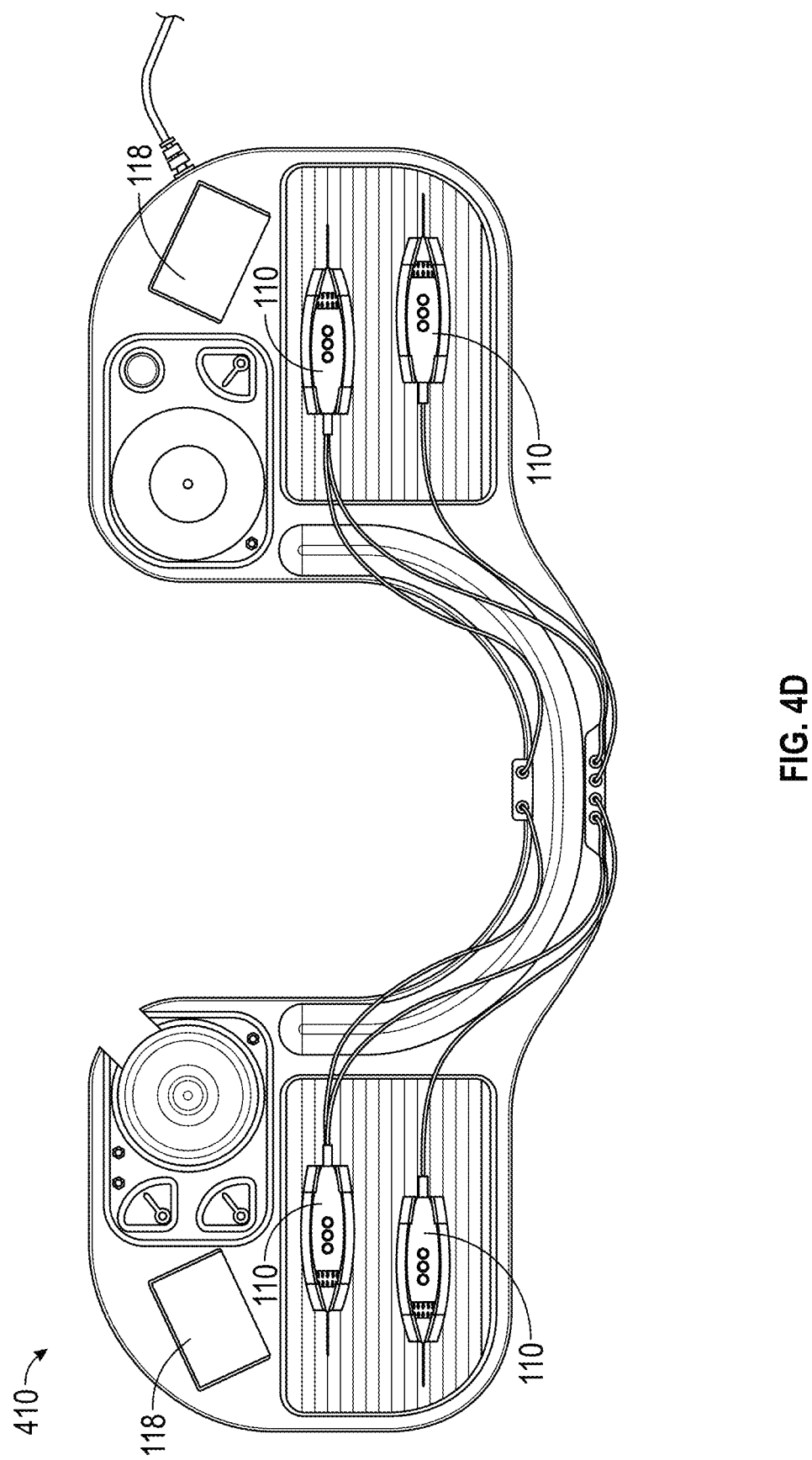
Figure 4F:
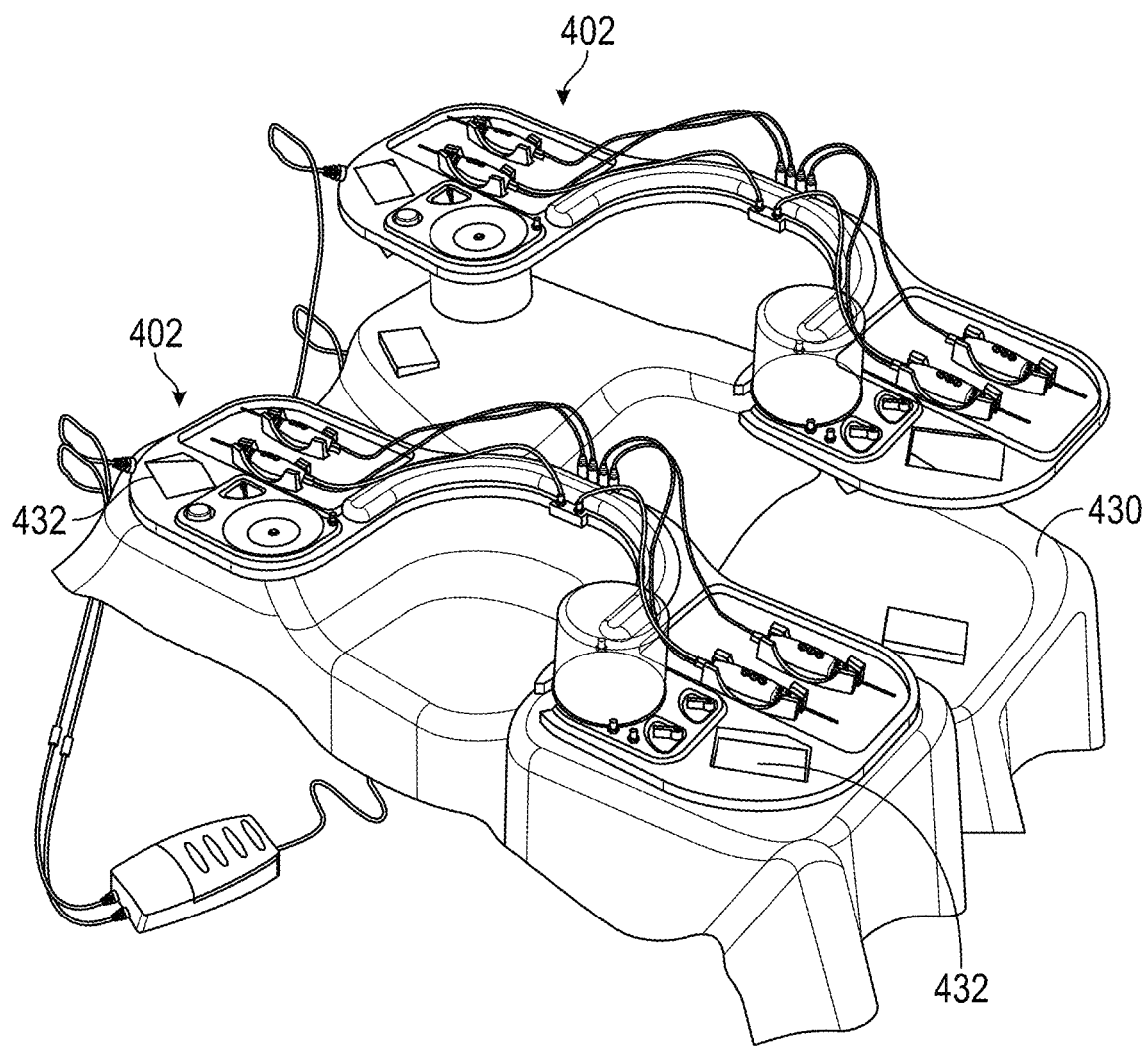

FIG. 4D illustrates a top view of the surgical tray system 410. FIG. 4E illustrates a bottom perspective view of the top or disposable portion 402 of the surgical tray system 410. The view in FIG. 4E illustrates in more detail openings 408 for viewing of the displays 118, and a drive portion 204 of the motor 122A, such as a coupling configured to mechanically coupled to a pump head coupled to a BSS bottle 122. In some embodiments, as described above, the motor 122A may be configured to be reusable and/or may be configured to be removable from the top or disposable portion 402 for use with another disposable portion 402.

FIG. 4F illustrates a fully assembled view and an exploded view of the top or disposable portion 402 of the surgical tray system 410 being positioned over the bottom portion 404 with a drape 430 positioned therebetween. It can be seen in FIG. 4F that the drape 430 comprises display windows 432 enabling viewing of displays of the bottom portion 404 through the drape 430. The drape 430 may further comprise one or more additional functional interfaces, as described above with reference to FIGS. 3A-3C.

Figure 5A:
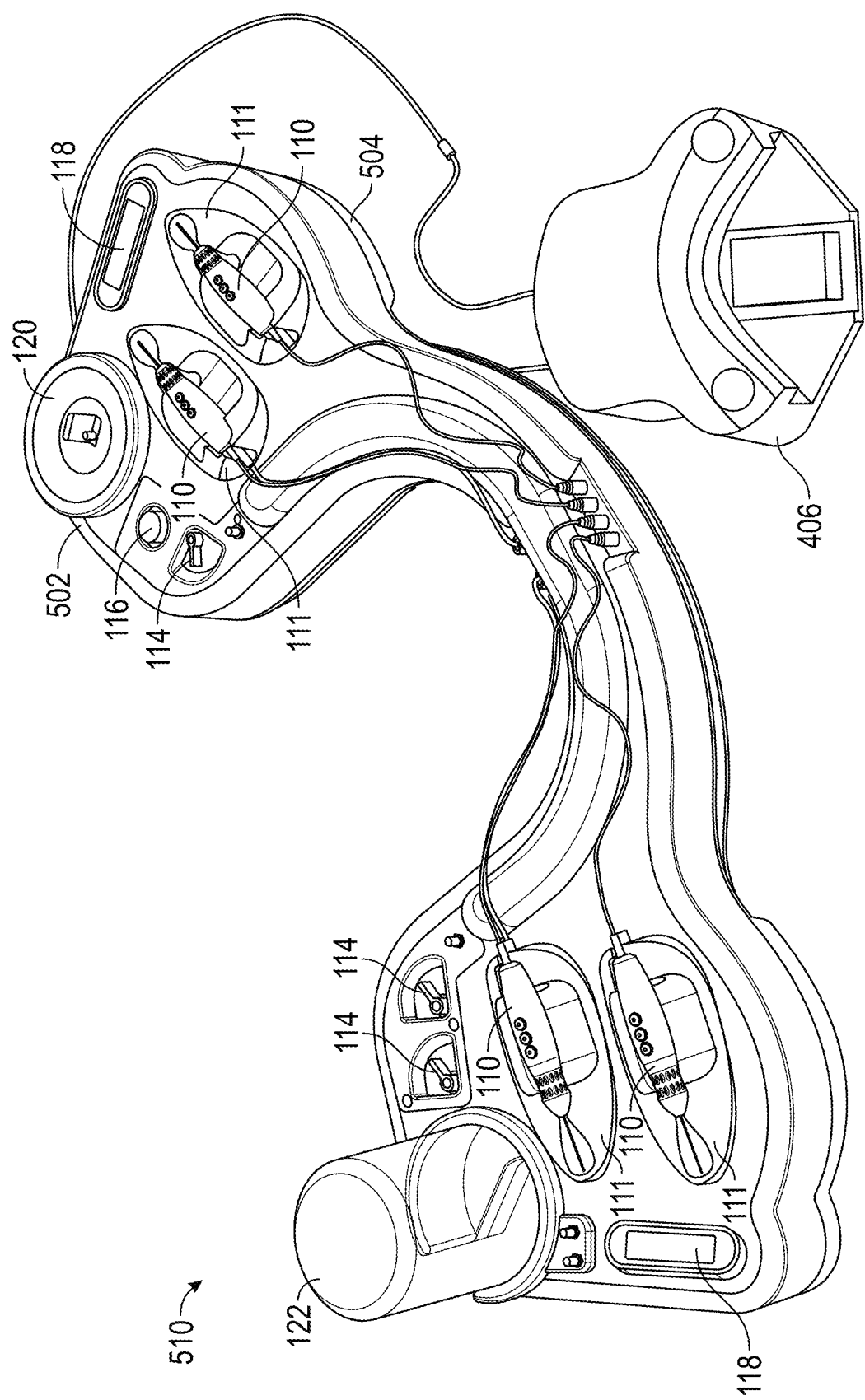
FIGS. 5A and 5B illustrate another embodiment of a modular surgical tray system.
Figure 5B:
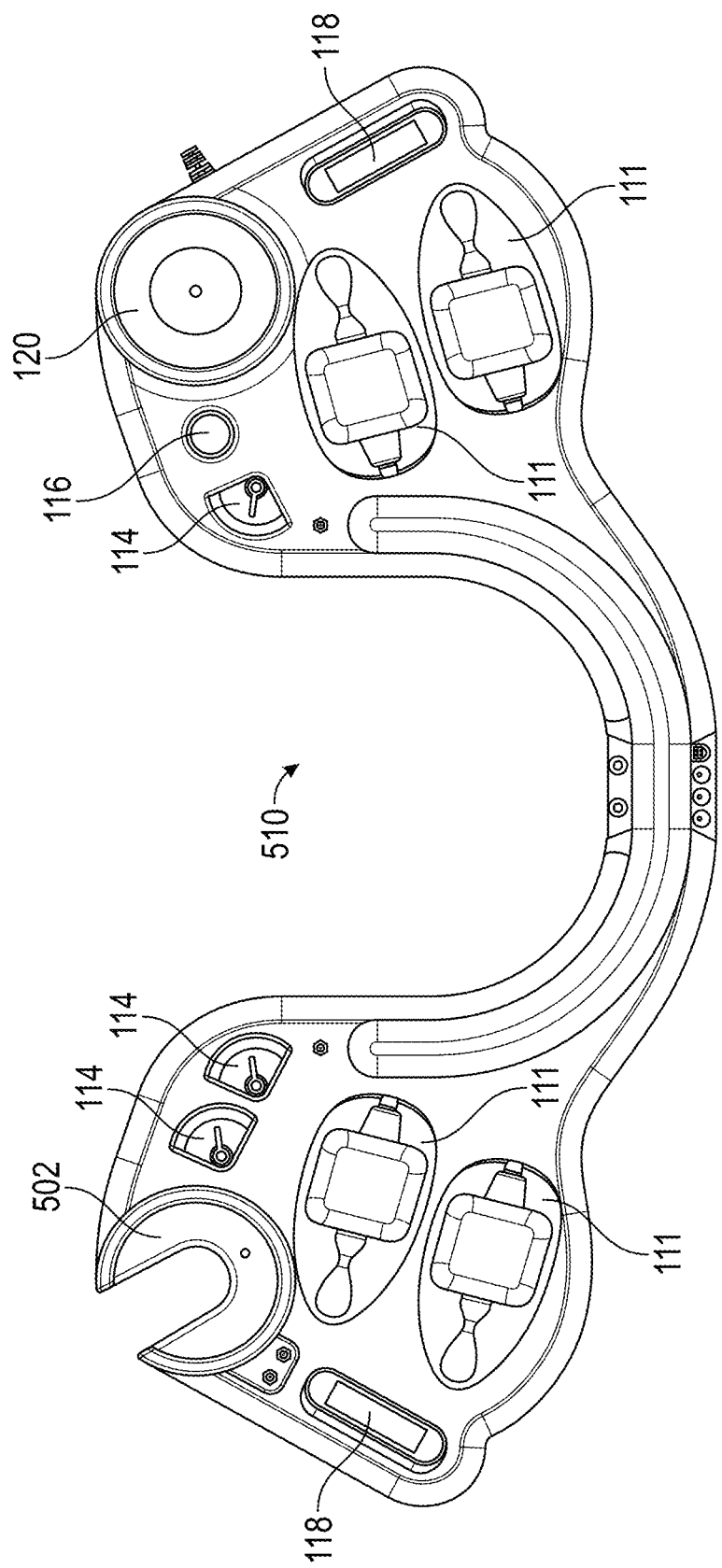

FIG. 5A illustrates another embodiment of a modular surgical tray system 510 comprising a top or disposable portion 502 coupled to a bottom or reusable portion 504. The modular surgical tray system 510 is similar functionally to the modular surgical tray system 410 described above, but with a different layout of and/or design of some of the features. Various elements of the surgical tray system 510 utilize similar reference numerals to represent features similar to those of the surgical tray system 410. FIG. 5B illustrates a top view of the surgical tray system 510 wherein the handpieces have been removed, illustrating the full handpiece support or storage locations 111. Further, the BSS bottle 122 has been removed, showing more detail of the motor receiving pocket or area 502.

Figure 6A:
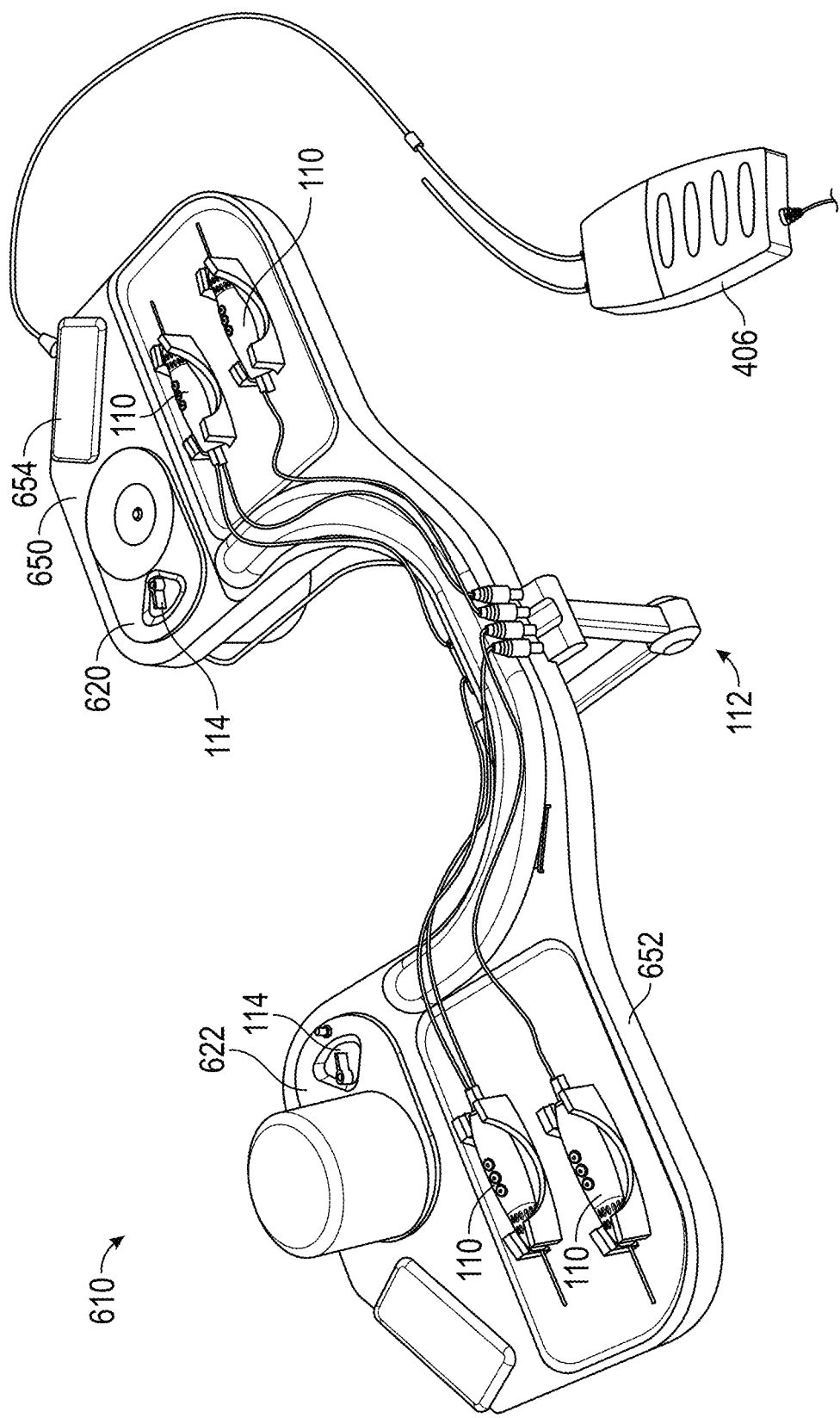
FIGS. 6A-6F illustrate another embodiment of a modular surgical tray system.
Figure 6B:
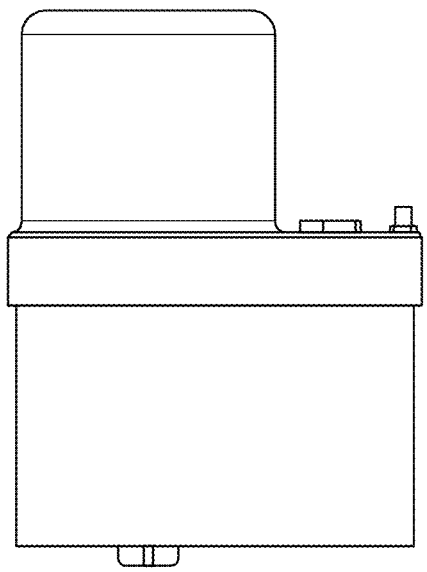
Figure 6C:
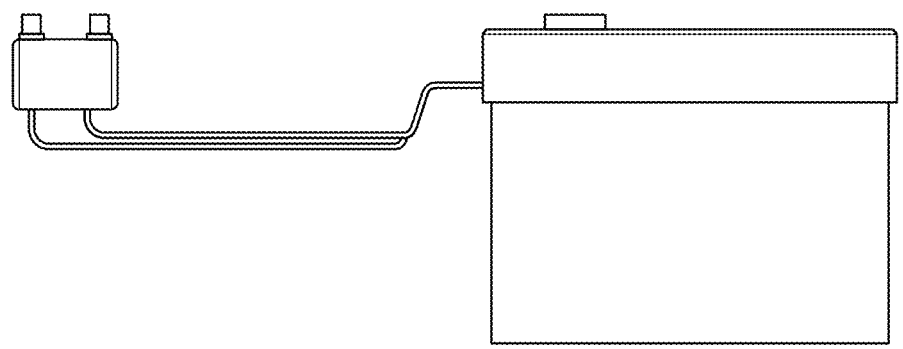
Figure 6D:
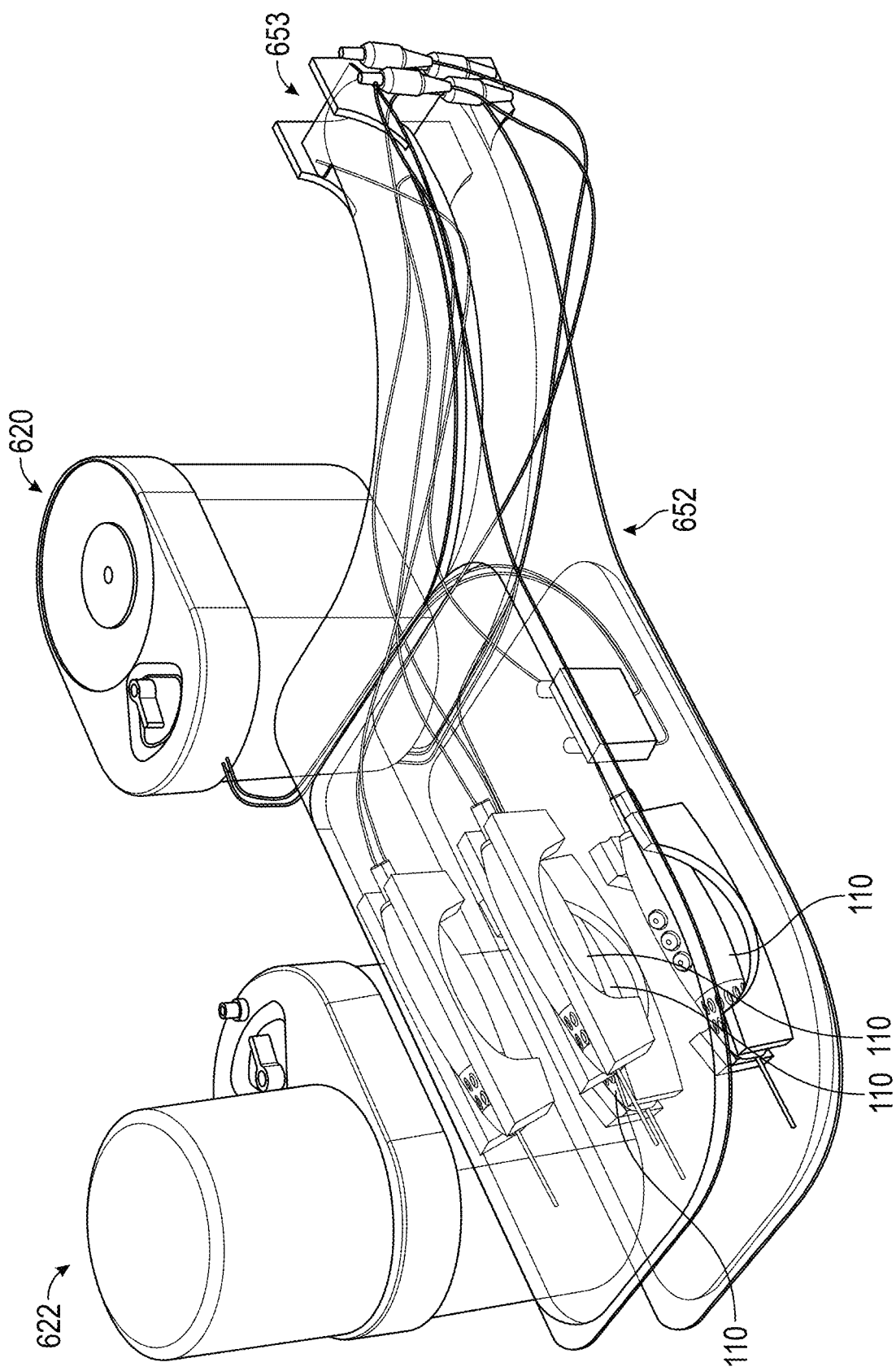

FIGS. 6A-6F illustrate another embodiment of a modular surgical tray system 610. In this embodiment, the modular surgical tray system 610 comprises a reusable or base portion 650 having a plurality of locations or interfaces configured for acceptance of or coupling to one or more modules. In this embodiment, the system 610 comprises a motor and pump module 622, a fluid reservoir receiver module 620, a power adapter module 654, and a modular tool insert 652. In an embodiment, the motor and pump module 622 can comprise a BSS bottle holder. In an embodiment, the motor and pump module 622 can comprise drive electronics for the infusion pump and/or the pressure sensor. In an embodiment, the drive electronics and/or the pressure sensor can be located in the reusable portion of the tray. In an embodiment, the fluid reservoir receiver module 620 can comprise the aspirated fluid reservoir and the aspiration pump. In an embodiment, the fluid reservoir receiver module 620 can comprise the drive electronics for the aspiration pump and the pressure sensor (or one or both of these may be instead located in the reusable portion of the tray). In an embodiment, the power adapter module 654 can be incorporated into one of the displays. In an embodiment, the power adapter module 654 can be located underneath the tray (in the reusable portion) or elsewhere (for example, on the ground, or the like). FIG. 6B illustrates a side view of the motor and pump module 622 (or in some embodiments a BSS bottle holder 622). FIG. 6C illustrates a side view of the fluid reservoir receiver module 620. FIG. 6D illustrates a perspective view of the motor and pump module 622 (or in some embodiments a BSS bottle holder 622), the fluid receiver module 620, and the modular tool insert 652, such as may come as a sterile package or assembly ready for use in a sterile operating environment. In this embodiment, it can be seen that the modular tool insert 652 comprises a folding or hinged joint 653 enabling the insert to be folded upon itself to reduce an overall package size of the insert, for example, to reduce a size during storage or shipping.

Figure 6E:
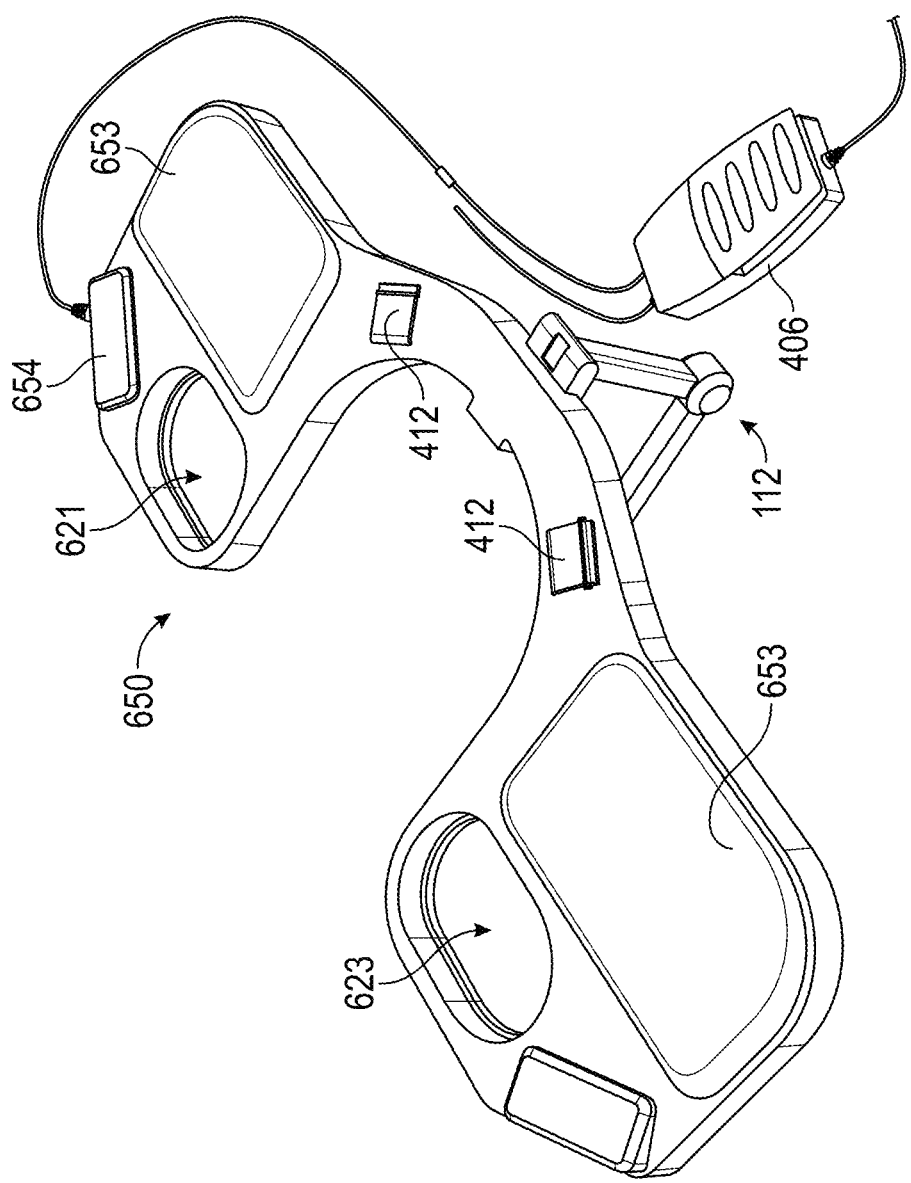
Figure 6F:
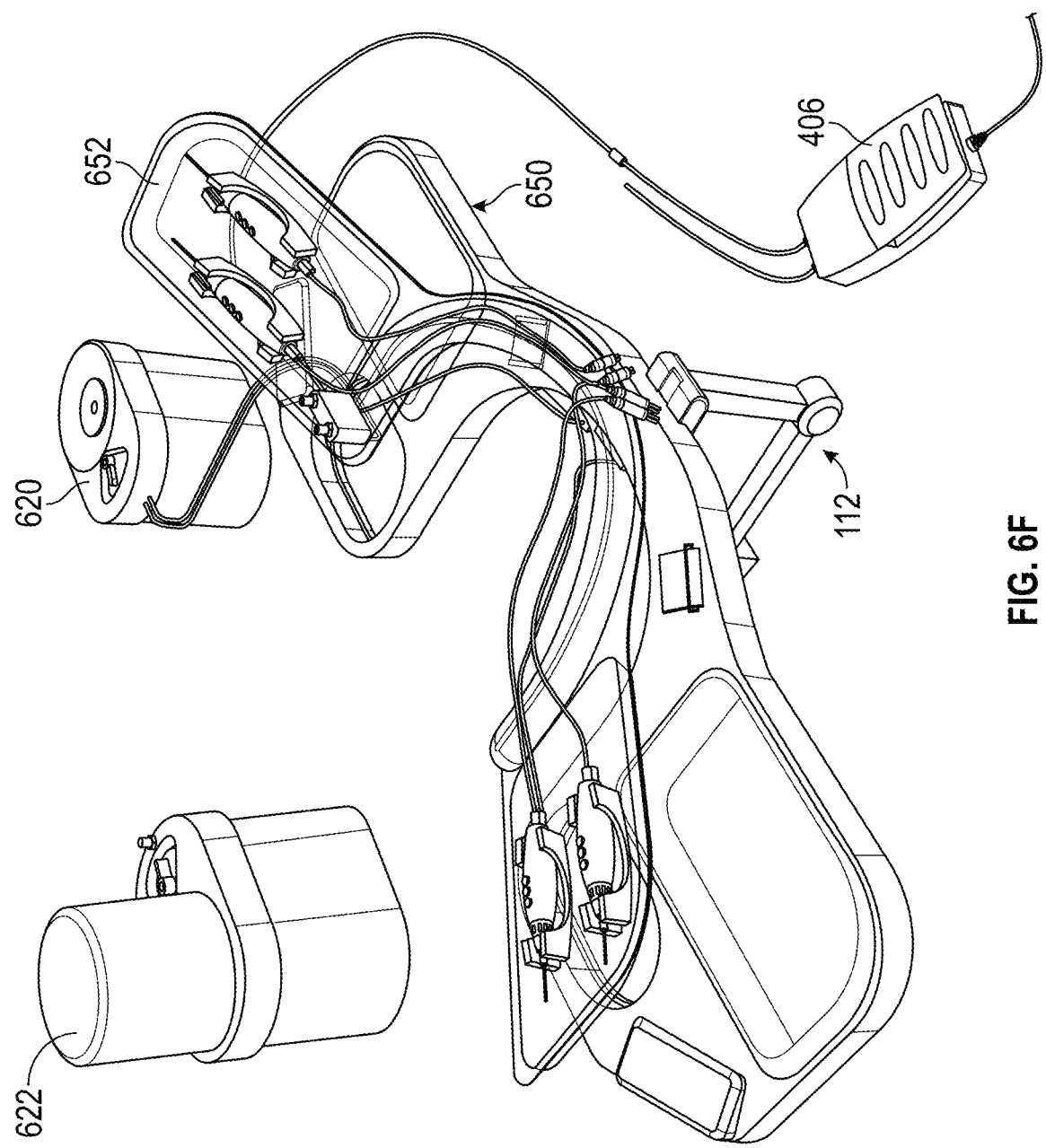

FIG. 6E illustrates a perspective view of the base portion 650 without the BSS holder, fluid receiver, or tool insert modules coupled thereto. The base portion 650 comprises a fluid receiver interface 621 shaped or configured to couple with the fluid receiver module 620, and a motor interface 623 (or BSS interface 623) configured or shaped to couple with the motor and pump module 622 (or BSS module 622). The base portion 650 further comprises two tool insert interfaces 653 comprising recessed areas for locating and/or retention of the tool insert 652. FIG. 6A further illustrates straps 412 configured to retain the base portion 652 to a support 112. In some embodiments, the straps 412 (or another portion of the base 650) may comprise a feature that helps to retain the modular tool insert 652 to the base portion 650, such as a hook and loop fastener, a magnet, and/or the like. FIG. 6F illustrates an exploded view of the modular surgical tray system 610.

In the example embodiment illustrated in FIGS. 6A-6E, the reusable portion 650 comprises a base that mounts directly or indirectly to the surgical bed or chair. The reusable portion 650 may comprise electronics, displays, motors, pumps, compressors or compressed gas sources, sensors, light sources, power supplies, batteries, and/or the like. The disposable portion 652 may comprise a tray that may be folded or hinged in half (for example, a vacuum formed or molded plastic tray) and upon opening, unfolding, or removal from packaging can be placed into the reusable tray 650, either directly or with a sterile drape between the two. The disposable tray 652 may comprise handpieces 110, fluidic components, optical components, pumps, electronics, motors and actuators, and/or portions of these or other components. The disposable tray 652 may in some embodiments be mounted or attached to the reusable portion 650 with aligning features, cutouts, wells, pockets, magnets, and/or the like.

In other embodiments, the reusable base 650 incorporates fewer or no active components (for example, electronics, displays, motors, pumps, compressors or compressed gas sources, sensors, and/or the like) but simply provides structural support to the disposable tray 652 (and/or BSS bottle and reservoir modules 622, 620). The reusable tray 650 may in some embodiments be draped with a standard drape to provide a sterile barrier upon which the disposable tray 652 is placed, since no functional interfacing is required through the drape in an embodiment where the reusable base 650 incorporates no active or functional components. In such a case, the reusable tray 652 may include features (for example, similar to those described below with reference to FIGS. 12A-12C and 13A-13C) to accommodate a reusable functional module, for example within a cavity isolated from the sterile environment.

Additional components may also be present in other related embodiments. For example, modular components 620, 622 (either disposable or reusable) as shown in FIGS. 6A-6F can be placed into the reusable tray 650. In some embodiments, the infusion function and aspiration function are separated into separate modules 620, 622 that include a portion of or substantially all components required for either function. In FIGS. 6A-6F, the aspiration and infusion modules 620, 622 are two distinct modules that share the same form factor and can be installed on either side of the reusable tray 650. This can be beneficial, for example, to enable placement of the infusion module 622 adjacent to the eye undergoing the surgical procedure and possibly using the opposite space to hold the aspiration module 620 or other functional component or module.

FIG. 6F shows an example of unfolding the disposable tray 652 (for example injection molded or vacuum formed) that is placed or otherwise supported on a reusable or separate disposable part 650, possibly separated by a sterile drape, bag, or similar. The unfolded disposable tray 652 may in some embodiments align on the bottom reusable part 650 through various aligning features or magnets for example, as further discussed with respect to other embodiments disclosed herein. The foldable disposable tray 652 may include handpieces 110 and/or it may also contain other functional elements such as an aspiration function module and/or infusion function module (including some or all of the following: pump, motor, pump head, fluid reservoir tank, electronics, fluidic components including tubing, filter(s), stopcock(s), fluid connector(s), and/or the like). Alternately, in some embodiments, some or all of the functional modules can be separate from the disposable tray portion 652 that holds the handpieces 110.

The tray in some embodiments may also be designed to connect to or otherwise mate with a separate surgical console. The tray and console may share electrical, mechanical, pneumatic, hydraulic, wireless, or other interfaces with each other. For example, in some embodiments the tray may provide a "docking station" or hub for the handpieces that can be conveniently located near the patient. This hub can be connected to the separate surgical console (electrically, pneumatically, and/or the like) and distribute the power (electricity, illumination, pneumatic/compressed air, hydraulic, mechanical, and/or the like) to the appropriate handpieces. The tray can also in some embodiments communicate information to the console, for example to control the power sources (voltage, current, pneumatic pressure, light intensity, and/or the like) and/or to display information on the surgical console's display.

The tray may also be designed in some embodiments to connect, mount, or otherwise mate to a surgical microscope or portion thereof. For example, the tray may be mounted to the optical head of the surgical microscope so that it hangs adjacent to the surgical site, or the tray may be mounted to the base or upright section of the microscope so that it is positioned adjacent to the surgical site. The tray may also be designed in some embodiments to tether power (electrical, laser, illumination, pneumatic, hydraulic, or other) and/or other functionality (e.g. data communication) from the microscope or a module connected to or mounted on the microscope.

Configuration of Profiles

The tray and/or base unit may also in some embodiments comprise a method of enabling the user to load specific settings and/or a user profile. For example, the tray or base may in some embodiments comprise a wireless RFID reader or near field communication (NFC) link that reads a "tag" (e.g. located on the user's ID badge) which is programmed with the user's preferences such as aspiration and infusion ranges, button functions, handpiece settings, and/or the like. In some embodiments, the tag comprises an identifier associated with the user's preferences, instead of the tag itself being programmed with the user's preferences. In some embodiments, the system is configured to automatically apply a user's preferences and/or to load settings associated with a specific user or tag when the tag is read by the wireless reader. In some embodiments, the tray comprises an antenna portion of the wireless reader, and the base comprises another portion of the wireless reader, such as a processing unit, which can be electrically connected to the antenna portion when the tray is connected to the base. Such a design can be advantageous to enable a more expensive portion of the wireless reader, such as the processing unit, to be reusable. The tray and/or base unit may in some embodiments comprise a USB or memory card interface or similar means of allowing the user to transfer information to the tray or base to, among other things, load or set settings and/or a user profile.

Figure 7:
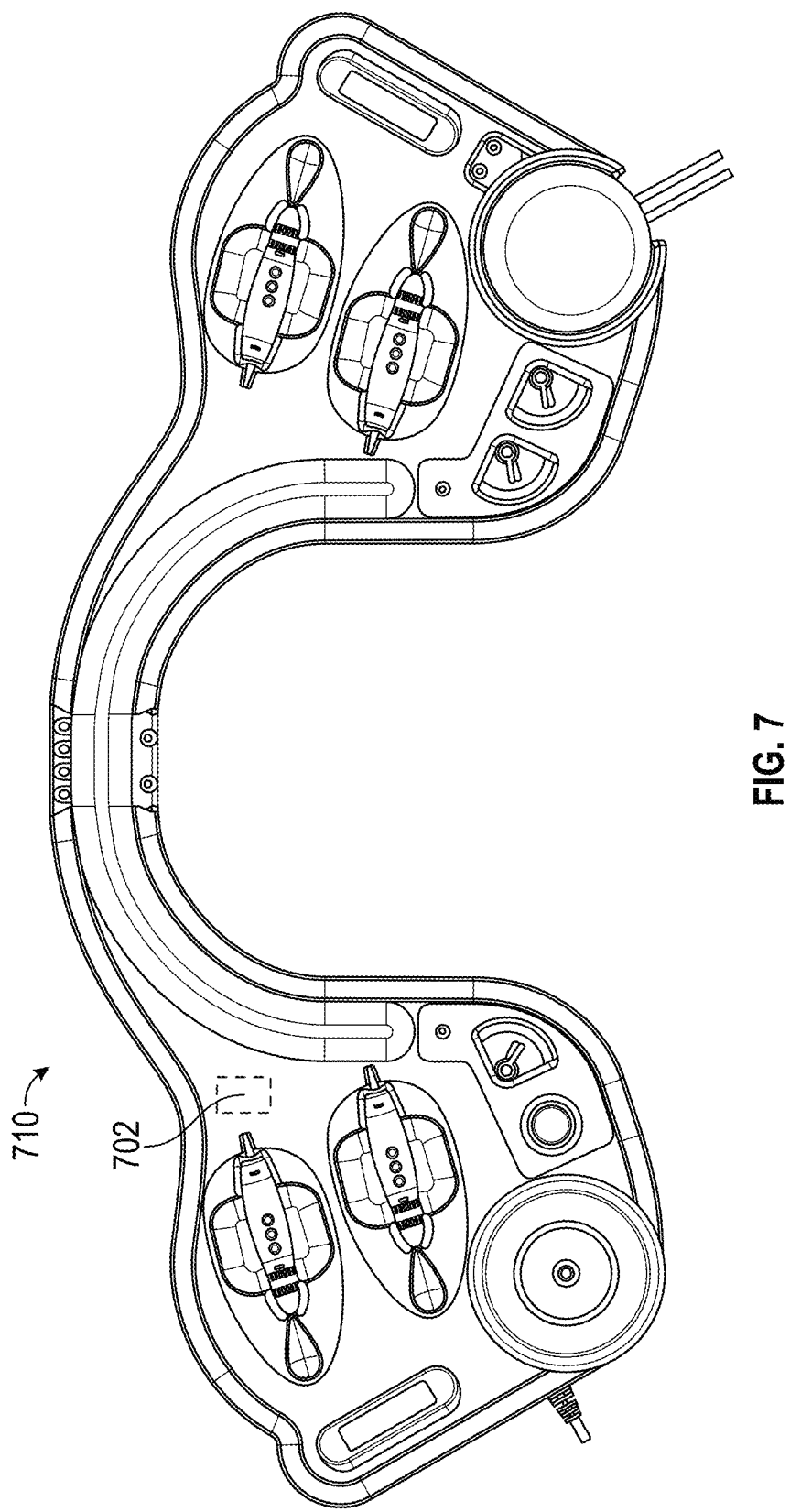
FIG. 7 illustrates another embodiment of a surgical tray system.

FIG. 7 illustrates a top view of a surgical tray 710 similar in design to the surgical tray 10 illustrated in FIG. 1A. The surgical tray 710, however, further comprises an antenna 702 configured to communicate wirelessly with a tag, near field communication device, and/or the like to enable configuration of parameters, user preferences, and/or the like. In some embodiments, the antenna 702 may be electrically coupled to a processing unit to enable the processing unit to configure the parameters, preferences, and/or the like.

Surgical Tray Components/Functions

A surgical tray in various embodiments can be configured to provide one or more of a multitude of components and/or functions for performing a surgical procedure. In addition to components and functions described above, the components and/or functions may comprise, but are not limited to: infusion, aspiration, one or more handpieces, illumination, laser therapy, display, audio feedback, one or more footpedals, and storage. These components and functions are described in greater detail below.

Infusion

The tray in some embodiments may provide infusion of fluids (balanced saline solution aka BSS and other fluids, including silicone oil, viscoelastic gels, dyes/stains, and/or the like) and/or gases into the eye, either the posterior or anterior chamber, for example by using a handpiece, such as one of the various handpiece embodiments disclosed herein. The infusion source (for example, a bottle or bag) may include a light (for example, an LED) to illuminate fill level, preferably but not necessarily the color red to minimize the impact on the surgeon's low light vision. The infusion fluid pathway may comprise in some embodiments a pressure and/or flow sensor to determine infusion and/or intraocular pressure and/or infusion flow rate. The fluid pathway and sensor may in some embodiments be separated by a filter or membrane to prevent contamination of the fluid and/or damage to the sensor, or in some embodiments non-contact measurement methods may be utilized. The tray may comprise in some embodiments a means of holding or securing the infusion fluid bottle or bag, such as a cup-holder or hook and/or the like, and a spike, needle, or fluidic attachment for extracting the contents of the bottle or bag. The tray may comprise one or more infusion systems to provide infusion for different fluids or gases simultaneously, on demand, or in a particular order. The tray may comprise stopcocks or other valves (manual or automated) to enable selection between different infusion sources (e.g. BSS or oil) or infusion locations (e.g. an infusion port next to the left eye vs. an infusion port next to the right eye).

In some embodiments, the tray may comprise multiple infusion systems, for example two separate systems located on opposite sides of the tray, each system designated for use with the adjacent eye. This can be advantageous to help ensure the tubing length from the infusion system to the patient's eye is minimized. The tray may also in some embodiments comprise multiple infusion systems (e.g. one for BSS and one for silicone oil) that are optimized for different viscosity fluids. In preferred embodiments, the total tubing length or fluid path length from either the infusion source (e.g. BSS bottle) or the infusion pump to the infusion cannula (which is inserted into the patient's eye) is minimized. Minimizing this fluid path length can improve the overall performance of the infusion system. The responsiveness of an infusion system that is actively maintaining an intraocular pressure level (e.g. via feedback control) during a surgical procedure is directly related to the length of the tubing set connecting the infusion source or infusion pump to the eye. Infusion systems with longer tubing sets, as is typical in commercially-available ophthalmology surgical consoles that are not located immediately adjacent to the patient, result in an undesirable lag or delay when measuring or adjusting the intraocular pressure as compared to those with shorter tubing sets. The infusion cannula can also be primed faster (before insertion into the patient's eye) in an infusion system with short tubing sets. In a preferred embodiment, this length (either source to cannula or pump to cannula) will not exceed 24 inches, but additional embodiments may be utilized that allow this length to reach 36 inches or more.

In one embodiment, the tray system comprises a separate infusion system for injecting silicone oil and similar viscous fluids. The oil infusion system may be a separate module that is utilized only in surgical cases that require oil infusion. The oil infusion system may be connected to a handpiece connector in order to supply power to the oil infusion system and provide a communications interface between the oil infusion system and the tray or base electronics. In some embodiments, the oil infusion system is designed as a handpiece with an endoscopic needle or tube that is used to infuse the oil or fluid into the eye. In other embodiments, the oil infusion system interfaces to the infusion cannula already inserted in the eye for BSS infusion. The infusion of oil may be done manually (for example, by depressing or squeezing a plunger and/or the like), it may be done pneumatically or hydraulically (for example, using a separate pump, compressor, compressed gas source, and/or the like), or it may be done electromechanically, for example with a motor, solenoid, or similar actuator that can infuse the oil (for example, a ballscrew/leadscrew, Hamilton syringe type configuration that moves a plunger to expel the oil from a syringe or cartridge, and/or the like).

Some embodiments utilize a pump or other means to provide fluid infusion. The pump style may be a standard Venturi, peristaltic, or diaphragm design, or another standard or non-standard pump variety. The infusion system may in some embodiments rely on other mechanisms of action to achieve fluid infusion, for example a fluid-filled syringe depressed either manually (for example, by the surgeon or an assistant) or automated (for example, via a syringe pump mechanism, actuator, motor, servo, ballscrew/leadscrew, spring, and/or the like).

Some embodiments may be configured to use a manually or automatically adjustable pole to raise or lower the BSS bottle or bag, exploiting gravity to provide a variable infusion pressure related to the height of the fluid source.

Some embodiments may be configured to pump air into or out of the fluid bottle to control the infusion pressure and therefore intraocular pressure (forced gas infusion). Pumping gas into the bottle increases the infusion pressure, while drawing air out of the bottle via pumping, vacuum, or venting (for example, through a tube or needle whose intake port is located above the water level) decreases the infusion pressure. Using this technique not only enables precise control of the infusion pressure but it also helps dampen pressure spikes and dips. The pulsating flow output of a peristaltic pump can also be minimized when using the peristaltic pump to pump air into the fluid bottle to increase infusion pressure.

Some embodiments utilize a compressed gas, e.g. a nitrogen or other gas (preferably inert) filled cartridge, canister, or tank as a source of pressure to enable fluid infusion (for example, via Venturi action or forced gas infusion). The cartridge, canister, or tank may be reusable/refillable or disposable and intended for single-use or limited use.

Some embodiments utilize a soft infusion fluid bag (as opposed to a glass or rigid plastic bottle). The soft bag may in some embodiments be located in a fixture between two or more plates that can squeeze or otherwise exert pressure on the bag in one or more axes. The distance between the plates (and thus the squeeze force) can be controlled manually by the surgeon or assistant or automatically, for example through a mechanical system comprising one or more of an actuator, motor, servo, cam, solenoid, gear, ratchet, rack and pinion, band, belt, pulley, chain, and/or the like. Increasing the squeeze force increases the infusion pressure; decreasing the squeeze force decreases the infusion pressure. Likewise, a similar mechanism can be used on a smaller container of infusion fluid, for example a reservoir into which infusion fluid drips or flows from the original infusion bottle or bag. A check valve can be included in some embodiments to prevent backflow into the original bottle or bag. The soft bag may also be located in an air-tight rigid container, which can have air pumped in or out (or vented) to increase or decrease the pressure on the external surface of the bag. Since the bag is not rigid, but compressible, the infusion pressure can be adjusted by adjusting the pressure in the rigid container. Likewise, a similar mechanism can be used on a smaller container of infusion fluid, for example a reservoir into which infusion fluid drips or flows from the original infusion bottle or bag. A check valve can be included to prevent backflow into the original bottle or bag.

In some embodiments the infusion fluid(s) are included in or integrated into the tray system so that the tray and fluid are packaged, sterilized, and shipped as a single system that can be disposed of after the surgical procedure. This is in contrast to a system wherein the tray is packaged, sterilized, and shipped as a separate component than the infusion fluid (e.g. BSS bottle) which may be from a different manufacturer altogether. Such a system may also include a separate additional means of introducing infusion fluids into the fluidic path of the system, for example if the included fluids are exhausted during the surgical procedure.

Aspiration

In some embodiments, the tray may provide aspiration functions, for example from a vitreous cutter, soft-tip, or phaco handpiece. The aspiration function may be provided through the use of a pump or by another means. The pump style may be a standard Venturi, peristaltic, or diaphragm design, or another variety. The aspiration pump system may also rely on other mechanisms of action to achieve vacuum draw at the needle tip, for example a syringe with a depressed plunger connected to the aspiration needle either directly or via a tube, the plunger being drawn back to produce a vacuum force, the action of being drawn back accomplished either manually (for example, by the surgeon or an assistant to the surgeon) or through a semi-automated or fully automated process (for example, a syringe pump mechanism, an actuator, motor, servo, ballscrew/leadscrew, spring, and/or the like), and/or the like. Some embodiments may utilize compressed gas (such as previously described), for example to generate a vacuum for aspiration through Venturi action. The aspiration fluid pathway may in some embodiments comprise a pressure or flow sensor to determine aspiration vacuum pressure and/or aspirated fluid flow rate. The fluid pathway and sensor may in some embodiments be separated by a filter or membrane to prevent contamination of the fluid and damage to the sensor, or non-contact measurement methods may be utilized.

In some embodiments, the tray may also incorporate a reservoir tank to hold the waste aspirated fluid and tissue. The tray may comprise a window and/or a light (e.g. LED) preferably but not necessarily the color red to minimize the impact on the surgeon's vision, to enable to the surgeon to visualize the fluid level in the reservoir tank. The reservoir tank may in some embodiments comprise a fluid level sensor to measure the level of aspirated fluid and remaining free volume. This may be utilized, for example, to alert the surgeon if the reservoir tank is near full capacity. The reservoir tank in some embodiments may be configured to expand as the volume of fluid inside increases (for example, as a balloon or bladder style reservoir, a reservoir with accordion-style collapsible walls, and/or the like).

Locating the aspiration pump and waste reservoir in or near the tray and in close proximity to the patient or within the sterile field can be preferable in some embodiments to, among other things, minimize the tubing length required, which improves the performance and responsiveness of the aspiration system. This reduces the path length of the aspirated fluid, thereby reducing the requirements of the aspiration mechanism and eliminating long tubing sets that slow the response time (for example, when the surgeon changes the rate of aspiration or switches from aspiration to reflux) and can entangle the surgeon and assistants in the operating room.

The tray may in some embodiments comprise stopcocks or other valves (manual or automated) to select between different aspiration intake sources (for example, a vitreous cutter handpiece and a soft trip extrusion handpiece).

Handpieces

In some embodiments, the tray system may comprise one or more handheld probes or handpieces that may comprise a needle (for example, 18 gauge, 20 gauge, 23 gauge, 25 gauge, 27 gauge or other size) inserted into either the anterior or posterior chamber of the eye during a surgical procedure (such as, for example, one or more of the various handpieces described herein with reference to FIGS. 1E, 4A, 5A, 6A, and 8A). Handpieces in some embodiments may comprise one or more of vitreous cutters/aspirators, endoilluminators, laser therapy/photocoagulation probes, diathermy/electrocautery/ablation probes, scissors, soft-tip extrusion probes, phacoemulsification/phacomorcellation probes, intraocular lens (IOL) inserters, forceps, mechanical probes, and/or other commonly used instruments. Some handpieces may incorporate more than one function. A handpiece may in some embodiments comprise one or more buttons and/or other user interfacing features that allow the surgeon to control the functions of that specific handpiece and/or possibly other functions as well (such as, for example, rates of infusion or aspiration).

Vitreous Cutter Handpiece

In some embodiments, a tray system comprises a vitreous cutter handpiece for removal of vitreous during a vitreoretinal procedure. The handpiece may in some embodiments be tethered to the tray via a multi-conductor cable that provides power and an optional communications interface (for example to communicate with the tray or base unit electronics, for example the status of button presses on the handpiece). In some embodiments, the cutter mechanism may be powered by a motor or motor and gear assembly inside the handpiece. In some embodiments, the cutter mechanism may be powered pneumatically by an external pneumatic source (for example, a pump, compressor, compressed gas source, and/or the like) that is connected to the handpiece via one or more flexible pneumatic tubes. The external pneumatic source may be located within the tray or the non-disposable base unit (for embodiments that incorporate a base as previously described). The cutter mechanism may in some embodiments be powered by a transmission cable or torque coil that rotates, reciprocates, or translates in one or more axes. Using the principles of electromagnetism, the cable or coil may be used to supply electrical power to the handpiece as well, for example by rotating or otherwise moving a magnet in proximity to a wire coil and generating a current that can power the electronics of the handpiece. The cable or coil may be driven by a motor, solenoid, electromagnet, linear actuator, and/or the like that is located external to the handpiece, for example in the tray or non-disposable base unit. The cable or coil connected to the handpiece may be coupled to the motor or drive actuator in the base via a shaft coupling, spline coupling, or similar to enable ease-of-setup by a surgeon or assistant in the operating room. In some embodiments, a magnetic coupling may be used to maintain a sterile field between the motor and the cable or coil. The cut speed, rate of aspiration and other functions may be controlled by buttons or other user interfaces on the handpiece itself, or through a footpedal.

Similar drive configurations may also be used for lens removal or phacomorcellation handpieces as well as other mechanically-driven instruments.

Figure 8A:
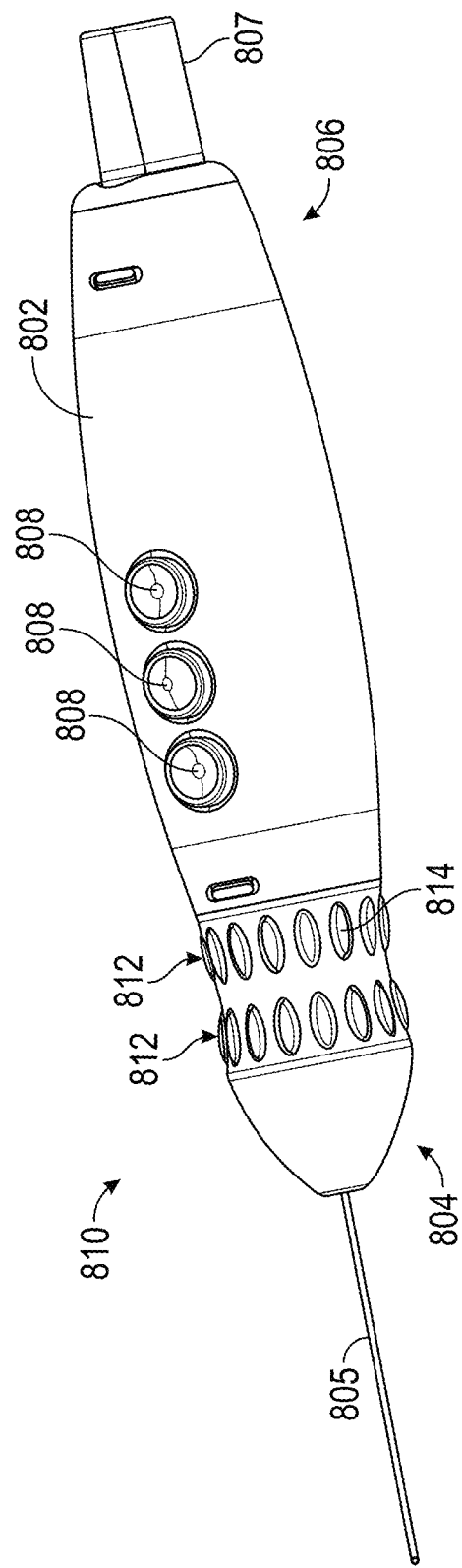
FIGS. 8A and 8B illustrate an embodiment of a handpiece having a plurality of buttons.
Figure 8B:
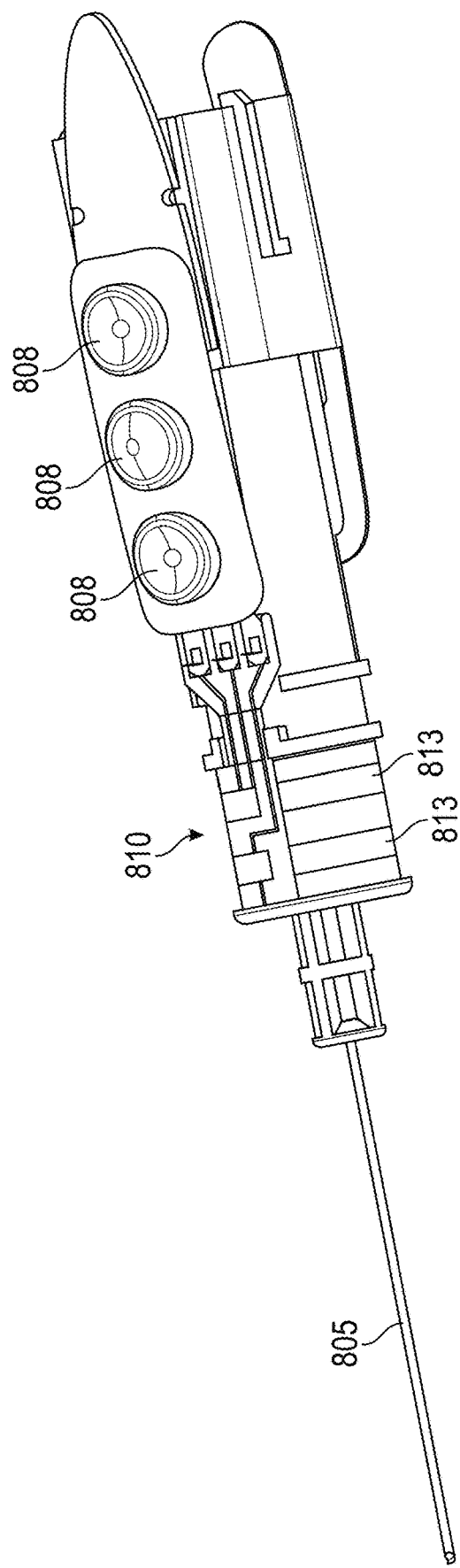

In some embodiments, a vitreous cutter handpiece may be a handpiece 810 as illustrated in FIGS. 8A and 8B, as further described below. In some embodiments, a vitreous cutter handpiece may comprise one or more features similar to as disclosed in U.S. Patent Application Publication No. 2008/0208233, entitled DISPOSABLE VITRECTOMY HANDPIECE, which is hereby incorporated by reference herein in its entirety.

Endoilluminator Handpiece

In some embodiments, a tray system may comprise an endoilluminator handpiece that provides illumination inside the eye. The handpiece may be tethered to the tray in some embodiments via a multi-conductor cable that provides power and an optional communications interface (for example to communicate with the tray or base unit electronics, for example the status of button presses on the handpiece). The endoilluminator may in some embodiments incorporate a light source (for example, white LED or RGB LED) that is coupled to a fiber or fiber bundle installed in an endoscopic needle. Alternately, the light source may be located in the tray or base unit and coupled (either permanently or using a detachable interface) to a fiber or fiber bundle that terminates in an endoscopic needle in the handpiece.

In some embodiments, an endoillumination handpiece may comprise one or more features similar to as disclosed in U.S. Pat. No. 8,172,834, entitled PORTABLE HANDHELD ILLUMINATION SYSTEM, which is hereby Incorporated by reference herein in its entirety.

Soft-Tip Extrusion Handpiece

The tray system may in some embodiments comprise a soft-tip extrusion handpiece that incorporates a soft tubing material (for example, silicone or the like) for aspirating vitreous and fluids from the retina. The handpiece may in some embodiments be tethered to the tray via a multi-conductor cable that provides power and an optional communications interface (for example, to communicate with the tray or base unit electronics, for example the status of button presses on the handpiece). The rate of aspiration and other functions may be controlled by buttons or other user interface features on the handpiece itself, or through a footpedal. The endoillumination power output and other functions (such as infusion rate) may in some embodiments be controlled by buttons or other user interface features on the handpiece itself, or through a footpedal.

Diathermy/Electrocautery Handpiece

The tray system in some embodiments may comprise a bipolar electrocautery handpiece that is capable of controlled cauterization of tissues. The handpiece in some embodiments may comprise two nested needles or tubes separated by an insulating layer (such as, for example, polyimide tubing or the like). The exposed distal end of the two needles or tubes act as electrodes for the bipolar electrocautery. The handpiece may in some embodiments be tethered to the tray via a multi-conductor cable that provides power and an optional communications interface (for example to communicate with the tray or base unit electronics, for example the status of button presses on the handpiece). The handpiece may in some embodiments have integrated electronics for generating the high voltage waveform required for electrocautery, or alternately the electrocautery circuitry may be located in the tray or base unit and supplied to the handpiece via insulated wires. The diathermy/electocautery function and other functions may be controlled by buttons or other user interface features on the handpiece itself, and/or through a footpedal.

Laser Therapy Handpiece

The tray system in some embodiments may comprise a fiber-based laser handpiece that is capable of photocoagulation. The handpiece may in some embodiments be tethered to the tray via a multi-conductor cable that provides power and an optional communications interface (for example to communicate button presses and system status with the tray electronics). The handpiece may in some embodiments incorporate a light source, such as a laser diode, that has sufficient power for photocoagulation. The laser diode may in some embodiments be coupled to a fiber or fiber bundle that is mounted inside an endoscopic needle for insertion into the eye or other surgical site. Alternately, the light source and associated optics may in some embodiments be located in the tray or base unit with either a permanent or interchangeable optical interface to a fiber or fiber bundle that terminates in an endoscopic needle located in the handpiece. The laser therapy power output and other functions may be controlled in some embodiments by buttons or other user interface features on the handpiece itself, or through a footpedal.

Scissors

The tray system in some embodiments may comprise a powered scissors handpiece that enables the surgeon to cut tissue without requiring manual manipulation, for example using fingers to squeeze, slide, or otherwise activate the cutting mechanism of the scissors. In one embodiment, the scissors are tethered to the tray via a multi-conductor cable that provides power and an optional communications interface (for example with the tray electronics). Power to the cutting mechanism is provided in some embodiments by the tray via the tethered cable. The cutting mechanism may in some embodiments comprise a motor, solenoid, linear actuator, nitinol or shape memory alloy wire (for example, a wire that contracts when a current is passed through the wire and expands when the current ceases and the wire cools), and/or the like. Alternate embodiments may position the actuator in the tray or base, and mechanical cutting may be provided via a linkage, such as a transmission cable or torque coil that is rotated, reciprocated, or translated along one or more axes.

Handpiece Storage

In some embodiments, a tray may comprise space configured to hold the handpiece(s) when they are not in use (such as, for example, the spaces 111 illustrated in FIG. 1E), and/or may provide connectivity to the handpiece(s) via one or more of an electrical, fluidic, pneumatic, optical, and/or mechanical interface. The spaces to hold the handpieces and the top surface of the tray in general may in some embodiments comprise features to cope with undesired fluids that may be present on the tray during the procedure. For example, the tray top and handpiece areas (which may be recessed pockets or wells) may have recessed channels or holes to drain any fluids or carry any fluids away. Likewise, any recessed areas may include absorbent or sponge-like materials to absorb any unwanted fluids. The handpieces may be mounted in the tray prior to packaging and sterilization to simplify the pre-op setup procedure. The tray may in some embodiments include clips, straps, or other locking mechanisms that enable the handpieces to be secured in place, for example during shipment or movement of the tray. Additional handpieces may be packaged and sterilized separately, for example to enable replacement of a failed handpiece during a procedure without having to open an entire new tray system.

Handpiece User Interface Features

Some embodiments of handpieces comprise one or more means of acquiring user input, such as one or more buttons or switches (including, for example, membrane, tactile, pushbutton, rotary, joystick, hall sensing, capacitive touch, pressure sensitive, and/or the like) located on the handpiece, and/or inertial sensors (including gyro(s), accelerometer(s), magnetometer(s), and/or the like). These input methods can be used to control one or more functions of the handpiece and/or console, such as, for example, activating, deactivating, and controlling the probe tip motion and aspiration functions. For example, in some embodiments, the surgeon may press and hold one button to activate emulsification/morcellation, and release the button to stop emulsification/morcellation. The surgeon may press and release another separate button repeatedly to cycle through aspiration rates. The inertial sensors can be used in some embodiments for position tracking as well as user input. For example, the surgeon may orient or move the handpiece in a particular manner to perform a function; an example would be deactivating the system when the handpiece is placed upside down on a tray or table (the system would recognize the upside down orientation of the handpiece and the lack of motion/movement); a second example would be lightly tapping on the handpiece with a finger to activate or deactivate a function (the accelerometer will detect the handpiece deflection caused by the tapping); yet another example would be rotating the handpiece in a clockwise fashion to increase the rate aspiration or some other function and rotating the handpiece in a counter-clockwise fashion to decrease the rate of aspiration or some other function (where the angular motion is detected by the gyro). The user input may in some embodiments be processed or otherwise acted upon internally within the handpiece, or the input may in some embodiments be relayed to a separate console or tray via a tethered electrical connection (for example, conductive wires/cables) or wireless connection (for example, RF, inductive, or infrared) for example. The handpiece may in some embodiments comprise a microcontroller or microprocessor for registering user input, controlling the functions of the handpiece, and/or communicating with external components of the system (for example a console or tray). The handpiece may in some embodiments comprise wireless capabilities to transmit and receive information to/from a separate console, tray, display, and/or other handpieces.

Some embodiments comprise analog buttons (such as, for example, a pressure or deflection sensitive button) that provide finer control over the handpiece functions than a standard binary (on/off) or momentary switch. For example, one or more analog buttons sensitive to pressure or deflection may be used to provide fine control of functions such as, for example, cut speed, aspiration, or illumination/laser power output. In one embodiment, one or more pressure-sensitive buttons in the grip of the handpiece can be used to control rate of aspiration or cut speed; the harder the surgeon squeezes, the higher the cut speed or rate of aspiration for example. Likewise, other sensors can be incorporated that measure flexion, deflection, or translation such that the further a surgeon pushes, slides, or otherwise moves a button, the higher the rate of, for example, aspiration or cut speed. This can be achieved, for example, with button implementations that vary a parameter (such as resistance or capacitance) based on an applied input (such as pressure or deflection). For example, one button implementation may be sensitive to pressure such that the harder the surgeon squeezes, the lower (or higher) the resistance, which can be measured by the handpiece electronics (and/or remote electronics, such as electronics located in a tray or base). Another implementation utilizes a change in capacitance, such that the distance (and therefore capacitance) between two parallel conductive plates varies with the force applied to a button. Another implementation may connect different circuits depending on how far a button is depressed or moved. Yet another implementation may utilize magnetic sensors to detect the location of a magnet and/or magnetic field strength to determine how far a button has been depressed or moved. Yet another implementation utilizes capacitive touch technology to provide analog control.

FIGS. 8A and 8B illustrate an embodiment of a handpiece or surgical instrument 810 comprising a housing or body 802 having a plurality of buttons 812, 808. FIG. 8A is a perspective view of the handpiece 810, and FIG. 8B is a perspective view of the handpiece 810 with the housing or body 802 removed to enable visualization of features positioned beneath the housing 802. The handpiece 810 comprises a proximal end 806 adjacent a cable interface 807, and a distal end 804 having a surgical tool 805, such as a needle, extending therefrom. In some embodiments, the surgical tool 805 is permanently or semi-permanently installed. In some embodiments, the distal end 804 is configured to enable a surgical tool 805 to be positioned in a coupled engagement with the distal end 804.

The handpiece 810 comprises three buttons 808 positioned adjacent to an exterior surface of the housing 802. In this embodiment, the buttons 808 comprise digital, binary, or momentary buttons or switches, meaning they have two states, namely on or off, for controlling of a feature. The buttons 808 may, for example, comprise mechanical switches that selectively open and close an electrical circuit when an actuation surface of the button 808 is moved relative to the housing 802.

The handpiece 810 further comprises in this embodiment two pressure sensitive buttons 812. In other embodiments, the handpiece may comprise fewer or more pressure sensitive buttons. Each of the two pressure sensitive buttons 812 comprises a circumferential force-sensitive resistor 813 that is configured to change a resistance value based on a magnitude of pressure applied against a surface of the force sensitive resistor 813. In some embodiments, the force sensitive resistor 813 comprises a thin multilayer polyimide sheet. In some embodiments, as can be seen in FIG. 8A, the buttons 812 comprise an actuation surface extending circumferentially around the handpiece 810 and/or housing 802 that, when depressed, presses against the force sensitive resistor 813. In some embodiments, the exterior surface of the buttons 812 comprise tactile regions or features 814, illustrated in FIG. 8A as a plurality of raised bumps spaced circumferentially around the handpiece 810 and/or housing 802. Such a configuration may be advantageous to, for example, enable a user or surgeon to precisely control a feature when the handpiece 810 is in any rotational position with respect to the user's hand.

As used herein, the word "button" may be used interchangeably with other words or phrases, such as switch, selector, user input, and/or the like. One of skill in the art will recognize that a variety of user interface features, including buttons or other similar features, may be used with the techniques disclosed herein to detect a user input.

In addition to traditional on/off or momentary buttons and analog buttons that depend on some type of electrical or electromechanical contacts, additional user input solutions are feasible that eliminate the need for electronics in the handpiece and/or the need for tethered power and communication interfaces to the handpiece. Such embodiments may be advantageous to, among other things, increase manufacturability and/or reduce cost of disposable components of the system, such as, in some embodiments, the handpieces.

Optical Buttons

In some embodiments, user input can be detected using buttons that rely on principles of optics and optical fiber, instead of (or in some embodiments, in addition to) electrical or electromechanical features. For example, in some embodiments, one or more buttons may have one or more fibers, light pipes, or optical waveguides associated with it, the fibers extending from the handpiece to the tray or base unit electronics (either as a continuous fiber or one or more fiber sections optically connected together). The fiber may be coupled to a light source (such as a light source located in the tray or base unit) and may propagate light to the button location. A button may be designed to bend or otherwise flex the fiber when the button is depressed, reducing or eliminating the light propagation through the fiber and/or changing the polarization of the light through the fiber, both of which are detectable by the electronics and can be used to indicate a button press. Other embodiments instead alter or route/reroute the light path (e.g. a reflective surface on a button, the surgeon's fingertip, etc.) such that the change can be detected and identified as a button press. The principles of fiber interferometry can also be used, such that a button press sufficiently alters the fiber so that the changes to phase altering interference fringes and the location thereof can be detected and interpreted as button presses. In a similar fashion, fiber Bragg grating sensors, long-period fiber grating sensors, and similar embodiments can be integrated into the fiber(s) to measure strain, thereby detecting changes in the fiber and their location(s). Some embodiments may utilize one of the optical techniques disclosed herein, and some embodiments may utilize more than one of the optical techniques and/or may utilize one or more of the optical techniques and one or more non-optical techniques.

In some embodiments, one or more buttons each have a single continuous fiber associated with it. The fiber is routed from the electronics in the tray or base to the handpiece button and back to the tray or base (either as a continuous fiber or as two or more sections optically coupled together). When the button is pressed, the fiber is bent in such a manner as to decrease or eliminate the light propagation, change the polarization of the light in a detectable manner, or induce strain in the fiber that alters the interference fringes in a detectable manner. In other embodiments, one or more buttons each have two fibers associated with it (each either as a continuous fiber or as two or more sections optically coupled together), one that carries the light from the tray to the button and another that acts as a return for the light back to the tray. The button is designed such that when it is depressed, light is allowed to propagate from the source fiber to the return fiber. This can be accomplished, for example, with a reflective surface or a transmissive or light pipe material that is angled or positioned properly when depressed, or even using the surgeon's fingertip to redirect the light from the source fiber to the return fiber.

Another embodiment comprises a single fiber for both the source and return path of the light, since fiber can simultaneously propagate light in both directions. For example, an optical circulator can be configured to allow light to be injected into the fiber at the source (such as the tray or base unit) while simultaneously separating any reflected light along the same fiber to be detected by a photodetector or other sensor in the electronics. Such reflections could be caused by a reflective surface (or even fingertip) at the end of the fiber, or even a bend, flex, or twist of the fiber.

In another embodiment, a single fiber or optical waveguide provides the source light to each button, and each button has an additional individual return fiber to indicate button presses.

In other embodiments, instead of individual fibers for each button, a single fiber is routed from the tray or base to each button in series and back to the tray or base. Different buttons are designed to alter the polarization or light propagation different amounts, such that each button can be distinguished from each other. Alternately, the optical path distance (such as the fiber length) between each button can be adjusted such that the principles of optical time domain reflectometry or similar can be used to determine the location along the fiber of the button press, and hence which button was pressed.

FIGS. 9A-9D illustrate example embodiments of handheld medical instruments or handpieces comprising one or more optical buttons. FIG. 9A illustrates schematically a handpiece comprising a housing or enclosure 802 having two optical fibers 906 passing therethrough. In this embodiment, an actuating member 904, when placed close to tips or ends 907 of the optical fibers 906 is configured to reflect light from one optical fiber 906 to another optical fiber 906, the reflection of which may be detected by hardware, for example, in a surgical tray or console. In some embodiments, the actuating member 904 is a portion of a physical button that is configured to reflect light. In some embodiments, the actuating member 904 is a user's finger, in some embodiments a gloved finger.

In some embodiments, the two separate optical fibers 906 may also be implemented as, for example, a single fiber with two or more waveguides, for example the source light would propagate down the core and the return light down one or more claddings of the fiber, or vice versa. Also note that a single source fiber may in some embodiments supply light to multiple buttons, with each button paired with an independent return fiber or independent waveguide, for example, multiple claddings, in a custom-designed return fiber. Alternatively, each button may have a separate source fiber providing light modulated at a different frequency for each button, with a common shared return fiber, with the modulated signal allowing the processing hardware to distinguish between different signals.

In some embodiments, a technique for enabling multiple buttons incorporates a filter or attenuator that attenuates the light propagation through each button differently (for example, 100%, 50%, 25%, and/or the like) or filters the wavelength (assuming a broadband light source) through one or more or each button so that the remaining wavelengths or the power attenuation could be measured by the processing hardware, such as, for example, in the surgical tray or console. In some embodiments, the wavelength of the light may be broadband (for example, white light or multi-wavelength light) or it may be single wavelength (for example infrared) and may be modulated to minimize interference issues with other ambient sources of light.

FIG. 9B illustrates another embodiment of a surgical handpiece comprising an optical button. The embodiment illustrated in FIG. 9B comprises an optical fiber 906 terminating at an end or tip 907. An actuating member 904 may have light reflective properties such that, when the actuating member 904 is positioned adjacent the tip 907, light is reflected back into the fiber 906, which can then be detected by, for example, tray or console hardware. Sensitivity in some embodiments can be adjusted to require contact by the actuating member 904 with the tip 907 and/or handpiece enclosure 802, or just a proximity to the tip 907 and/or handpiece enclosure 802.

FIG. 9C depicts another embodiment of an optical button. The embodiment illustrated in FIG. 9C comprises two optical fibers 906 and an actuating member 904 which, when moved relative to the enclosure 802 and/or fibers 906, moves a reflective member 908. When the reflective member 908 is positioned in front of tips or ends 907 of the optical fibers 906, light is reflected from one optical fiber 906 to the other optical fiber 906, enabling detection of the button press by processing hardware located at, for example, the surgical tray or console.

FIG. 9D depicts another embodiment of an optical button, wherein a deflectable member or portion 910 connected to or part of one or more optical fibers 906 is positioned to be deformed when an actuating member 904 is moved relative to the handpiece enclosure 802. For example, when the actuating member 904 contacts and/or presses against the deflectable member 910, the deflectable member 910 may bend or otherwise deformed in a manner that may be detectable by processing hardware, such as processing hardware located in or as a part of the surgical tray or console. In this embodiment, if the button is depressed, the actuating member 904 will bend the deflectable member 910. If the deflectable member or portion 910 is deflected sufficiently, the propagation of light through the fiber will be significantly decreased or eliminated, which can be detected by the processing hardware and interpreted as a button press. In an alternate embodiment, more light instead of less light is allowed to propagate the harder or further the button is pressed.

In some embodiments, the optical button configuration illustrated in FIG. 9D can also be configured to provide linear or pressure sensitive feedback through one or more of several techniques. First, the decrease in light throughput will correlate to how much deflection or bending the fiber is experiencing. The amount of light detected can be used to determine the overall position of the button. So, for example, the harder or further the user pushes the button, the greater the measured change in light throughput. Similarly, the bending of the fiber will change the polarization of the light through the fiber. This can also be detected by processing hardware and used to determine the magnitude of deflection. More advanced optical theory can also be used. For example, the fiber button can be one arm of a fiber-based interferometer (michelson, common path, mach zehnder, and/or the like) such that the change in optical path length and the phase changes induced in the fiber due to stress or bending can be detected in the processing hardware and measured to determine how hard or far the button was depressed. Another technique is to include gratings in the fiber during manufacturing to produce a strain sensor, such as a Fiber Bragg Grating Sensor or long-period fiber grating, that can be used to provide linear or pressure sensitive button functionality due to the correlated change in wavelength resulting from strain on the fiber (for example, caused by pressing or bending the fiber). These grating sensors can also be used for multiple buttons with only a single fiber by designing a grating along the fiber with different properties for each button such that the properties of each grating are distinguishable from each other by the processing hardware.

Yet another embodiment can use a single fiber for multiple linear or pressure sensitive buttons by detecting where along the fiber a strain or bend was induced, and correlating this to the position of the one or more buttons. This detection can be implemented using principles of time domain reflectometry, wherein the time for a light pulse to propagate through the fiber and reflect back to the source is measured and the distance determined, with the reflection caused by the button inducing a strain or impedance in the fiber. This is more difficult over a shorter fiber length and would benefit in some embodiments from the addition of fiber between the buttons to increase an optical path length between buttons.

In some embodiments, an optical button configuration may comprise one or more optical waveguides in addition to or in lieu of one or more optical fibers, such as a plastic light pipe or the like. Further, in various embodiments disclosed herein that refer to optical fibers, it should be understood that those optical fibers may be a continuous optical fiber and/or may comprise one or more sections coupled together, and or may comprise one or more optical waveguides in series with a fiber.

In some embodiments, an optical button is configured to enable, disable, or attenuate the propagation of light from a source waveguide (or fiber) to a return waveguide (or fiber), for example, with a reflective or absorptive surface, including a finger, to enable detection of a button press.

In some embodiments, an optical button uses a single fiber or waveguide in a loop configuration and alters a property of light in a detectable fashion, for example, by bending the fiber or waveguide. This property can be the power or magnitude (for example, attenuating or increasing the light throughput), the polarization of the light, the wavelength of the light (for example, by filtering out some wavelengths of a broadband light source and detecting the remaining wavelengths; or by shifting or filtering the wavelength for example through a grating design), the optical path length or phase of the light (for example, by bending or straining the fiber which can be detected in an interferometer setup). A related embodiment relies on the principles of total internal reflection and "evanescent waves." For example, by touching the outer surface of the fiber (stripped of any outer protective coating, if present), the refractive indices at the fiber interface are changed (for example, fiber to finger instead of fiber to air) which can alter the propagation of light through the fiber. This change may be detectable with sufficiently sensitive amplification and processing equipment.

In some embodiments, an optical button uses one fiber for multiple buttons, for example by using custom fibers with multiple waveguides (and possibly modulating the signal to or from different buttons); by filtering out different wavelengths depending on which button is pressed (for example, using multi-wavelength or broadband light); by attenuating the light by different amounts depending on which button is pressed; by using different fiber grating parameters for each button; by measuring the time for reflected pulses to propagate (time domain reflectometry) where the reflection is caused by a deformation or strain in the fiber caused by the activation of a button.

Pneumatic/Hydraulic Buttons

In some embodiments, buttons that utilize pneumatic and/or hydraulic principles are incorporated into the handpiece, which can in some embodiments (similarly to as with the optical button embodiments) eliminate the need for any electronics or electrical interfacing between the handpiece and the tray or base unit.

In some embodiments, one or more buttons of the handpiece may be attached to or fluidly coupled with a flexible pneumatic tube (for example, flexible silicone, vinyl or PVC tubing or the like) that is connected to the tray or base unit electronics (either using a continuous section of tubing or two or more sections in fluid communication). The electronics may comprise, for example, a pressure sensor that can measure the pressure inside the tube. This can be used to determine whether or not a button is pressed. For example, a depressed button may seal or pinch the tube that is otherwise open, unobstructed, or patent, in such a way that is detectable by the pressure sensor. Similarly, in some embodiments, the tubing may terminate in the handpiece such that the surgeon may cover the hole in the end of the tubing (such as with his or her finger) to indicate a button press. A bladder or balloon, for example at the end of the tubing, may be included such that when the bladder or balloon is depressed or otherwise modified (such as by an external force, for example, from a finger or from a movable component of the handpiece), the change in internal air/fluid pressure can be detected and interpreted as a button press. In some embodiments, instead of relying on ambient pressure, the tubing may be fluidly connected to an air or vacuum source such that the measured pressure will be different depending on whether or not the tubing is patent or sealed. In this embodiment, each button would have its own independent tubing. In another embodiment, multiple buttons can share a single tube, for example if each button restricted the flow through the tube to a different magnitude, such that each button would be distinguishable from the rest. For example, the first button may restrict the tubing completely, while the second button restricts the inner lumen of the tubing 75%, the third button 50%, the fourth button 25%, and so on, which may be distinguishable by a fluidly-coupled sensor.

FIGS. 10A-10C illustrate example embodiments of handpieces comprising pneumatic or hydraulic buttons. FIG. 10A illustrates schematically an example wherein an actuating member 904, such as a finger or a portion of a button, deforms a deformable member 1002 fluidly connected with tubing 1004 to enable detection of a change in pressure in the deformable member 1002 and/or the tubing 1004. In some embodiments, a flexible tube (e.g. vinyl or silicone tubing) 1004 with a balloon or bladder 1002 attached to the end of the tube that has some gas or fluid within it (e.g. air) can be used as a linear button. The harder the balloon or bladder 1002 is squeezed, pushed, or compressed, the higher the pressure inside the tube, which can be measured and processed by a pressure sensor and processing electronics located, for example, in the remote console or tray.

In some embodiments, the balloon or bladder 1002 may be directly pressed by the user's finger, or a button, lever, or other feature activated by the user's finger(s) or grip may apply the force to the balloon or bladder.

In some embodiments, the balloon or bladder 1002 does not have to be a separate component but can be integrated into the tubing 1004 itself. The tubing 1004 can be designed to have a ballooned area (for example, a segment with a larger diameter). A similar result can also be achieved (for example, the change in pressure can be detected and interpreted as a button press) by squeezing or compressing a tube that is simply sealed on the end. The advantage of a balloon or bladder with a larger diameter than the rest of the tubing is that the squeeze or compressive force will be amplified and therefore easier to measure by the pressure sensor and processing electronics and less susceptible to noise or interference.

In some embodiments, multiple buttons can be included in the handpiece by repeating the design of FIG. 10A; however it is also possible to incorporate multiple buttons using a single flexible tube with multiple balloons or bladders. Each balloon or bladder could, for example, in one embodiment, have a different diameter/volume, such that when pressed the processing hardware could determine which button was pressed (for example, which balloon was compressed) based on the amplitude of the signal. This permutation may be desirable to use with, for example, on/off or momentary buttons as opposed to linear buttons, although it could also be used with pressure-sensitive or linear buttons.

FIG. 10B illustrates another embodiment of a pneumatic or hydraulic button wherein a flexible tube 1004 (for example, vinyl or silicone tubing) that is open (for example unsealed) on the button end 1006 can be used to detect button presses. If the user presses their finger (or an another actuating surface) on the open end 1006 of the tube 1004, a pressure sensor and sensitive electronics that amplify and process the pressure signal can detect the changes in pressure and register a button press (for example, momentary or on/off).

FIG. 10C illustrates another embodiment of a pneumatic or hydraulic button wherein a flexible tube 1004 (for example, vinyl or silicone) can provide pressure sensitive, linear, or digital (for example, on/off or momentary) functionality. The tube 1004 is routed from the console or tray to the handpiece and back to the console or tray. There is an air source pumping air into one end of the tube and a pressure or flow sensor on the other end of the tube. When the user's finger (or another actuation surface) 904 presses against the tube (or against a button, lever, or similar, for example comprising opposing members 1008, 1010) the tube is constricted. The more the user squeezes, the more the tube is constricted, potentially to the point that no air can flow. Alternately, instead of squeezing the tube, the tube may be bent, which would likewise cause a reduction in air flow due to the collapsing wall of the pliable tubing. This change in air flow can be detected by the sensor and correlated to the amount of compression or deflection of the tube, thereby providing a linear style button output.

Embodiments of this and other designs can even use the pneumatic source that is often used to drive certain instruments such as aspirators and vitreous cutters.

Piezo Buttons

In some embodiments, buttons comprising piezo material (for example piezoelectric quartz or the like) provide user input functionality. Piezo crystals when bent, flexed, or otherwise deflected generate a voltage spike that can be used as an input mechanism. For example, a mechanical button designed to deflect a piezo material will generate a voltage when the button is pressed. If the piezo material is coupled via electrical wires to electronics in the tray or base unit (or in some embodiments in the handpiece), this voltage spike can be detected and interpreted as a button press. While the handpiece is tethered to the tray or base unit electronics with electrical wires in this embodiment, there are no active electronics required in the handpiece itself in this embodiment and it is not necessary to supply power to the handpiece via any wires or cables. Multiple buttons can be incorporated into the handpiece, each completing a separate circuit (for example, two independent wires per button or one independent wire and one shared ground wire); alternately, multiple buttons can share a single circuit or pair of wires to the tray or base unit by designing each piezo element to generate a different range of voltages such that each piezo element is distinguishable from the others based on the magnitude of the voltage generated when the button is pressed.

FIG. 11 illustrates an embodiment of a handpiece having a piezoelectric button comprising electrical wires 1102 coupled to piezoelectric material, such as a piezo crystal 1104 to detect deformation of the crystal via a voltage differential measured across the wires 1102. In some embodiments, the crystal 1104 is configured to be deformed by one or more of the actuating members 904, 904'.

In some embodiments, the piezo button incorporates one or more piezo crystals or elements that are connected electrically to the tray or console. No power is applied to the piezo crystal through the wires; instead the piezo element will produce a voltage when it is bent or deflected which can be detected by the tray or console electronics. The amplitude of the voltage that is generated is proportional to the amount of deflection of the piezo element—so the further the piezo is deflected, the higher the voltage spike. This property can be used to provide a pressure sensitive or linear-style output.

To incorporate multiple buttons without simply repeating the design for each button, multiple piezo elements can in some embodiments share a single set of wires if, for example, each piezo element is designed to provide a different voltage at a given deflection, such that the different voltage ranges are distinguishable from each other and can be correlated to a particular button. Alternately, each button can be designed to deflect its respective piezo element (assuming all piezo elements have approximately the same specifications) a different amount, thereby producing a different voltage amplitude range depending on which button is pressed.

In any of the illustrative embodiments disclosed in FIGS. 9A-11, the buttons can be binary on/off switches, or variable switches that produce responses or outputs that are linear, non-linear, or a combination of linear and non-linear with respect to the input received by the button.

Power Sources

Embodiments disclosed herein may employ one or more of a variety of power sources to perform the intended functions, including but not limited to actuation of the probe tip and aspiration as well as receiving and/or processing user input. The handpiece may in some embodiments be tethered to a console or tray that provides power (for example DC or AC voltage or current) via electrical wires. The handpiece may in some embodiments be powered by a rechargeable (secondary) internal battery (such as lithium ion/lithium polymer, NiMH, NiCd, or other chemistry), a non-rechargeable (primary) internal battery (such as alkaline, lithium manganese, or other chemistry), and/or an internal capacitor of sufficient capacity (such as a "super-capacitor" or "ultra-capacitor"). The handpiece can be in some embodiments powered wirelessly via a wireless power coupling system. For example, the handpiece may incorporate a "secondary" coil that can be inductively powered from a "primary" coil that is strategically located in proximity to the handpiece and driven by a power amplifier. For example, the primary coil can be mounted on the microscope and used to power a handpiece containing a secondary coil and positioned by the surgeon underneath the microscope during the surgical procedure. This inductive link (or a different inductive link) can also in some embodiments be used for bi-directional communication between the handpiece and the tray or console. The handpiece may also in some embodiments be powered pneumatically or hydraulically (tethered with tubing set to console or tray, for example) to provide emulsification and aspiration. The handpiece may in some embodiments be powered by a moving, reciprocating, or rotating cable transmission or torque transmission coil. The handpiece may in some embodiments be powered via a wound-up spring. The handpiece may in some embodiment comprise a turbine or other means of converting the cable, pneumatic or hydraulic power to electricity for powering, for example, internal microcontroller(s), sensor(s), actuator(s), and/or button(s). The handpiece may in some embodiments be powered by converting a squeezing, gripping, rotating, or sliding motion made by the surgeon on the handpiece grip into a useful motion (for example reciprocating or rotary motion to activate the probe tip). The handpiece may in some embodiments be powered by compressed air, for example a canister or cartridge inserted into the handpiece, or an external source. Additional power sources may be used to provide the desired functionality, and in some embodiments more than one power source may be used to power a handpiece (for example, an AC voltage driving a piezoelectric crystal mounted in a phaco handpiece for phacoemulsification and pneumatic power to provide the aspiration of the phaco handpiece).

Pressure-Sensitive Handpiece Tip

Some embodiments incorporate a pressure sensor in a distal tip of the handpiece to provide intra-ocular pressure readings from the anterior chamber or posterior chamber. The pressure sensor readings (and/or information derived from the pressure sensor readings) can be visually displayed (for example, on a stand-alone display, heads-up display, in-microscope display, or a display integrated into the tray or console) and/or audibly announced. In some embodiments, alarms and/or safety measures may be activated based on the pressure sensor readings. Furthermore the pressure sensor readings may be used in some embodiments in a feedback control loop to control the rate of infusion and/or aspiration during anterior segment or posterior segment procedures. The pressure sensor may in some embodiments be of the MEMS variety. The pressure sensor may in some embodiments be a fiber-based design. In some embodiments, the pressure sensor is incorporated into a separate component (for example, instead of distal tip of the handpiece) that is also inserted into or located adjacent to the anterior chamber or posterior chamber of the eye. For example, the pressure sensor may be incorporated into an infusion cannula or chandelier light source and the pressure measurements used to control the rate of infusion. Other embodiments may be configured to rely on external IOP measurements taken through established measurement techniques and processed by the handpiece or tray electronics.

Illumination

In some embodiments, the tray may comprise one or more light sources for providing illumination at the surgical site. Endoscope-based illuminators (endoilluminators) and other illumination devices, such as chandelier illuminators, can be coupled to the light source(s) via a single fiber or bundle of multiple fibers. The fiber(s) may in some embodiments have large numerical apertures to maximize coupling efficiency. The fiber(s) may in some embodiments be butt-coupled to the LED source or interfaced through a lensing system. The endoilluminator and chandelier illuminator, and/or the like can be permanently coupled to the light source via the fiber(s) or they may be coupled via an optical connector configuration that efficiently couples light from the light source into the fiber and allows the fiber of the handpiece to be attached and detached from the light source at will or on demand by the surgeon. The tray may in some embodiments comprise high brightness phosphor-based white LED(s) and/or RGB LED(s). More than one source may be provided to simultaneously accommodate, for example, one handpiece endoilluminator and one chandelier illumination device through an optical coupling; alternately, a single light source can be shared among two or more illumination components, for example through a free-space or fiber splitter. The constituent colors of the RGB LED(s) may in some embodiments be adjusted individually to provide improved visualization under different conditions, for example in the presence of a dye, stain, or indicator. Other embodiments comprise a xenon, mercury vapor, halogen, and/or other light source located in the tray and optical coupled to the handpiece via fiber. Alternate embodiments include a light source (for example, LED or laser) in the handpiece itself; the light source may be coupled (butt-coupled or otherwise) to a needle containing a light pipe, fiber, or fiber bundle that propagates the light to the distal tip of the endoilluminator probe. The fiber or fiber bundle may in some embodiments have a large numerical aperture to maximize coupling efficiency between the LED and the fiber. Alternately, the LED may be located at the distal tip of the needle, preferably sealed from the external environment (for example, behind a transparent window at the distal tip of the needle or potted in epoxy).

Laser Therapy

In some embodiments, the tray may comprise one or more laser sources for providing photocoagulation, ablation, cutting, and/or other laser therapy at the surgical site. For example, a laser therapy probe handpiece may comprise a fiber or fiber bundle mounted in an endoscopic needle inserted into the eye. The fiber probe may be configured to focus or collimate the therapeutic laser for use during surgery. The laser therapy probe can in some embodiments be permanently coupled to the light source via the fiber(s) or they may in some embodiments be coupled via a removable optical connector that couples light from the light source into the fiber. Alternate embodiments include a laser source in the handpiece itself; the laser source may be coupled (butt-coupled or otherwise) to a needle containing a light pipe, fiber, or fiber bundle that propagates the light to the distal tip of the laser therapy probe.

Display

In some embodiments, the tray may comprise one or more display(s) (for example, indicator(s), interface(s), LCD(s), and/or LED(s)) for displaying system information. The tray may also include audio feedback. The display(s) may also be located separate from the tray. Display(s) may be mounted in a heads-up configuration (for example, on the microscope) or projected into the optical path of the microscope for display within the visual field of the microscope. Display(s) may in some embodiments be located on or above the tray in the left and/or right periphery of the surgeon to enable viewing without turning the head. Display(s) may in some embodiments be located on the tray directly in front of the surgeon and viewable when looking downwards and provided with a shade or cover that prevents light pollution from the display from entering the microscope's objective lens or affecting the surgeon's vision. Alternately the display(s) may have a film, window, or other transparent cover that is polarized or contains lenticular grooves, parallax barriers, or other features that enable viewing from limited perspectives or are transparent from only a certain angle to prevent light pollution.

Audio Feedback

In some embodiments, the tray may comprise audio capabilities to provide feedback to the surgeon. The audio feedback may comprise in some embodiments a variety of tones with different frequencies, amplitudes, durations, and/ or the like. The audio feedback may in some embodiments comprise voice prompts that are capable of providing more useful and thorough feedback information to the surgeon. The voice prompts may be digitized audio recordings/samples or synthesized speech, and the voice prompts may be stored in non-volatile memory (for example, flash memory or a hard drive). The tray electronics may in some embodiments comprise a microcontroller or microprocessor that controls the voice prompts (and/or tones, and/or other audio feedback), activating the proper audio feedback based on input from the surgeon, a handpiece's hardware or software, the tray's hardware/software, and/or the like.

Foot Pedal

In some embodiments, the tray may comprise or be connected to one or more foot pedals (tethered or wireless) that enable control of the handpiece and/or tray functions (including, for example, infusion and aspiration rates, cutter speed, illumination power, and/or the like).

Storage

In some embodiments, the tray may comprise one or more areas (for example, holes, cavities, containers, voids, pockets, hooks, fasteners, magnets, and/or the like) configured to hold, store, or secure items used during the surgical procedure, including, for example, the handpieces, sutures, syringes/needles, trocars, and/or other instruments or supplies. The tray may also in some embodiments comprise an integrated sharps container to safely secure or dispose of sharps. The tray may in some embodiments comprise a magnet or magnetic surface to hold needles, sharps, and other metal items/instruments in place.

Example Disposable Tray Embodiments

In one preferred embodiment, a tray system comprises a disposable tray that comprises disposable electronics and disposable pumps (for infusion and/or aspiration). The tray system also comprises disposable handpieces with electronics and functional components integrated into one or more of the handpieces (for example, motor for vitreous cutter, LED for illumination, and/or the like). In some embodiments, the entire tray system is intended to be disposed of after a single use or limited number of uses.

In a second preferred embodiment, a tray system comprises a disposable tray with disposable pumps but with little or no active electronics. The electronics are integrated into a reusable base that interfaces with the disposable tray and handpieces. The handpieces may comprise integrated electronics and functional components.

In a third preferred embodiment, the tray itself comprises only disposable fluidic components. The reusable base unit incorporates the electronics and pump drivers (for example, motors) while the disposable pump heads or a portion thereof are located in the disposable tray. The handpieces may include integrated electronics and functional components.

In a related preferred embodiment, the tray itself comprises only disposable fluidic components. The reusable base unit incorporates the electronics and pump drivers (for example, motors) while the disposable pump heads or a portion thereof are located in the disposable tray. Other functional components are also incorporated into the base instead of the handpieces. These include: a mechanical source for the cutter and similar instruments, which may be a pneumatic or hydraulic source or a motor source to drive a transmission cable or torque coil; a light source for endoillumination; a laser source for photocoagulation. In some cases, the handpieces have no integrated electronics and rely on fiber-based, pneumatic, piezo, or similar non-electronic methods of acquiring user input. Alternately the handpieces may not incorporate any buttons and all control is done via a footpedal or buttons on the tray or reusable base unit.

Aseptic Container Modular or Hybrid Tray Embodiments

Some embodiments of surgical tray systems disclosed herein comprise a modular or hybrid design (as further discussed above), wherein one or more disposable portions couples with one or more reusable portions to create the complete surgical tray system. In some embodiments, the disposable portion is sterile and comprises (or otherwise provides for or creates) an aseptic cavity or enclosure configured to isolate a reusable portion from the sterile surgical field. In some embodiments, the aseptic cavity completely encapsulates the reusable portion. In other embodiments, the aseptic cavity covers at least enough of the reusable portion to isolate the reusable portion from the sterile surgical field, but does not completely encapsulate the reusable portion. For example, the cavity may be configured to cover a top and sides of the reusable portion, but to leave uncovered a bottom of the reusable portion, with the bottom intended to be positioned out of the sterile surgical field and thus not requiring covering, even though the reusable portion is placed in close proximity to the sterile surgical field.

In some embodiments, a sterile disposable tray (or one or more components of the tray) is configured to be opened up by the surgeon in a hinged, clamshell, or other fashion to enable a reusable module to be installed inside or underneath by the assistant (see, for example, FIGS. 12A-12C, further described below). The hinged lid or clamshell would then be closed, fully encasing or otherwise covering or isolating the reusable module and maintaining a sterile barrier between the reusable module (that may not be considered to be sterile) and the patient and surgeon. In another embodiment, instead of opening in a clamshell fashion, the disposable tray or a portion of it contains a drawer, lid, door, window, or similar feature that can be opened to allow the reusable module to be inserted (see, for example, FIGS. 13A-13C, further described below). In another embodiment, the reusable module is inserted into or mounted to the underside of the sterile disposable tray (or a component thereof), which may provide a cavity, pocket, recess or other mounting feature to hold or secure the reusable module (see, for example, FIGS. 14A-14C, further described below). In such an embodiment, a cover or lid may not be necessary because the manner and position in which the disposable tray is mounted to the surgical site (for example, the patient's bed or chair or the surgeon's armrest) may provide the proper boundary between the sterile and unsterile regions.

Figure 12A:
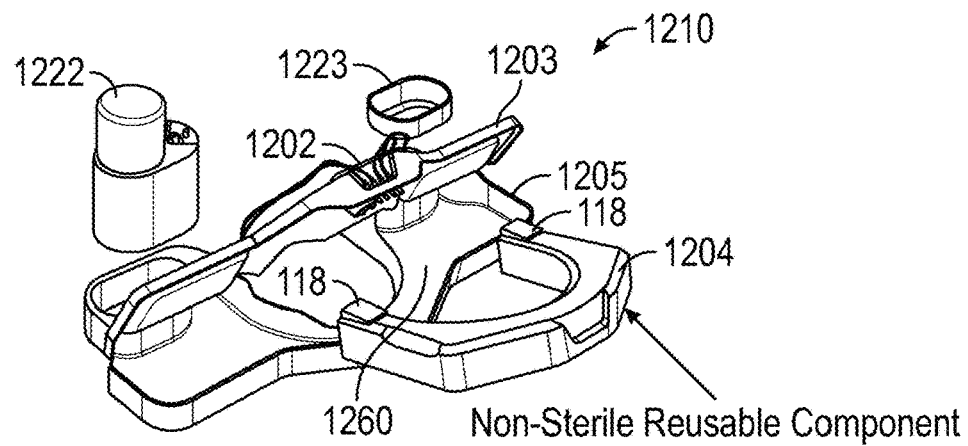
FIGS. 12A-12C illustrate an embodiment of a surgical tray system that isolates a non-sterile reusable component from a sterile surgical field.
Figure 12B:
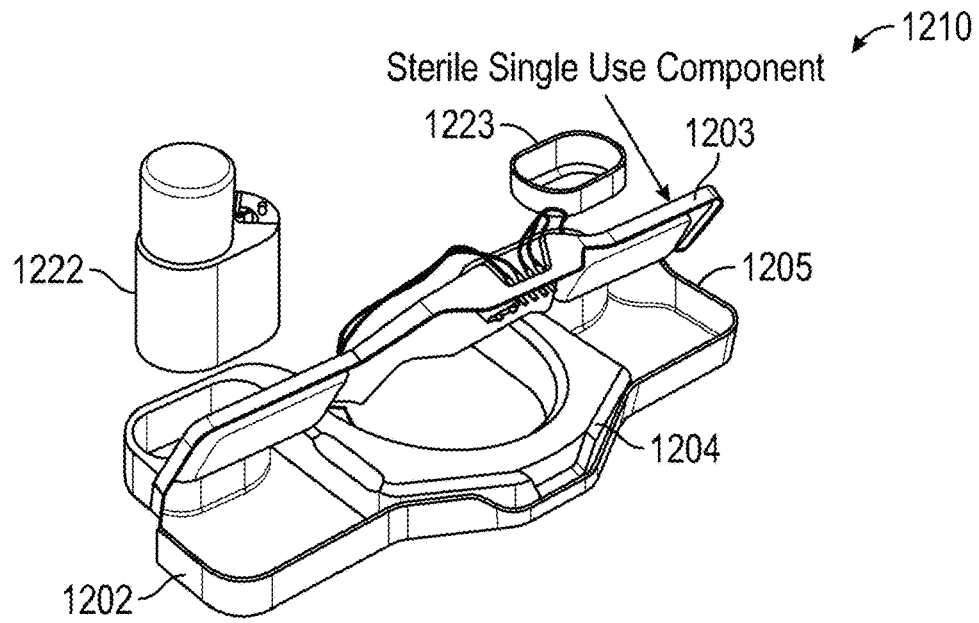
Figure 12C:
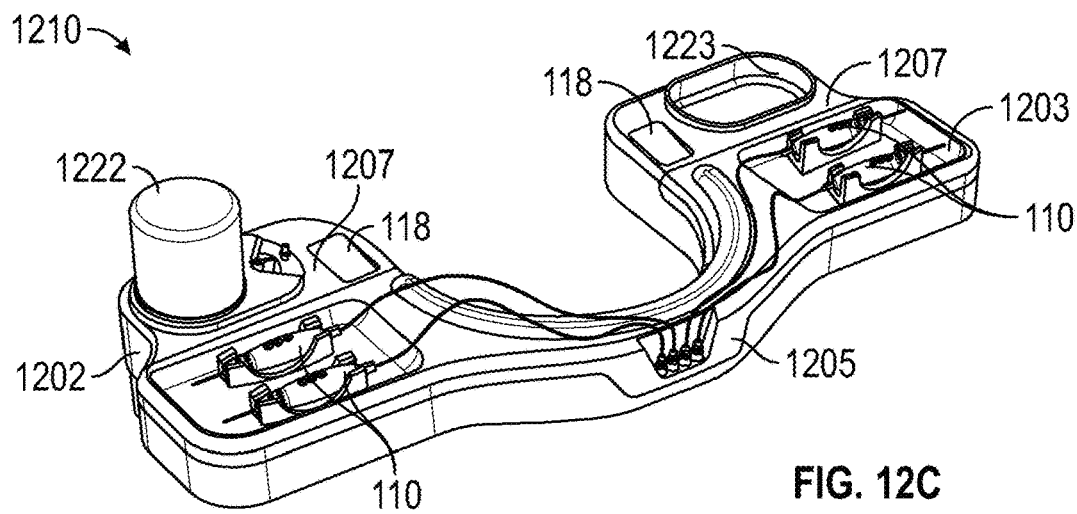

FIGS. 12A-12C illustrate an embodiment of a hinged or clamshell style surgical tray or apparatus 1210 comprising an aseptic container or cavity 1260 for insertion there in of a nonsterile reusable component 1204. Electrical, mechanical, optical, and/or fluidic connections are configured to be made between the reusable 1204 and single-use 1202 portions when the reusable portion 1204 is inserted into the single use portion 1202. Note that these drawings are only an example of such an embodiment. The actual single-use component 1202 can in some embodiments be smaller with some portions made to be reusable and simply draped or otherwise covered to provide a sterile barrier during a surgical procedure.

FIG. 12A is an exploded view of the surgical tray 1210, which comprises a disposable portion 1202 and a reusable portion 1204. In some embodiments, the disposable portion 1202 further comprises a fluid reservoir 1223 and/or a BSS bottle holder or infusion assembly 1222. In some embodiments, the BSS bottle holder 1222 and/or the fluid reservoir 1223 may be modular in nature, enabling them to be removed from and/or inserted within the disposable portion 1202, similarly to as described above with reference to other embodiments. In some embodiments, the BSS bottle and/or reservoir features may be integrated into the disposable portion 1202 and not be removable or interchangeable. FIG. 12B illustrates the surgical tray 1210 after the reusable portion 1204 has been inserted into the cavity 1260, but before the lid 1203 has been closed. FIG. 12C illustrates the surgical tray 1210 after the lid 1203 has been closed.

With further reference to FIGS. 12A-12C, this embodiment of a surgical tray or apparatus 1210 comprises a base portion 1205 and a lid 1203 hingedly connected to the base 1205 via hinged sections 1207. In this embodiment, the lid 1203 comprises areas for holding handheld medical instruments 110. In other embodiments, the lid may be smaller or larger than as illustrated in this embodiment, positioned elsewhere, and/or may not comprise areas for holding the instruments 110.

The reusable portion 1204 of the embodiment of FIGS. 12A-12C comprises one or more electronic displays 118 configured to be viewable through the disposable portion 1202 when the reusable portion 1204 is positioned within the aseptic cavity 1260 of the disposable portion 1202. Further, the reusable portion 1204 may in some embodiments comprise one or more other functional components configured to interface with the disposable portion 1202. For example, the reusable portion 1204 may comprise a computer processor configured to control one or more functions of the surgical tray, an optical light source, a laser source, a fluid source and/or reservoir, a motor, and/or the like. In some embodiments, the lid 1203 and reusable portion 1204 may comprise electrical connectors similar to as illustrated in FIG. 4C.

FIGS. 13A-13C illustrate another embodiment of a surgical tray or apparatus 1310 comprising a sterile disposable portion 1302 and a reusable portion 1304. The embodiment illustrated in FIGS. 13A-13C is similar to the embodiment illustrated in FIGS. 12A-12C. The surgical tray 1310, however, utilizes a drawer 1361 to access an aseptic cavity for placement therein of the reusable portion 1304, instead of utilizing a hinged or clamshell style design. Note that FIGS. 13A-13C are only an example of such an embodiment. In other embodiments, an opening for insertion of a reusable portion can be designed as a door or lid, instead of a drawer, that is opened to install the reusable module. As with other embodiments, electrical, mechanical, optical, and/or fluidic connections can be made between the reusable 1304 and single-use 1302 portions when the reusable portion 1304 is inserted into the single use portion 1302.

Figure 14A:
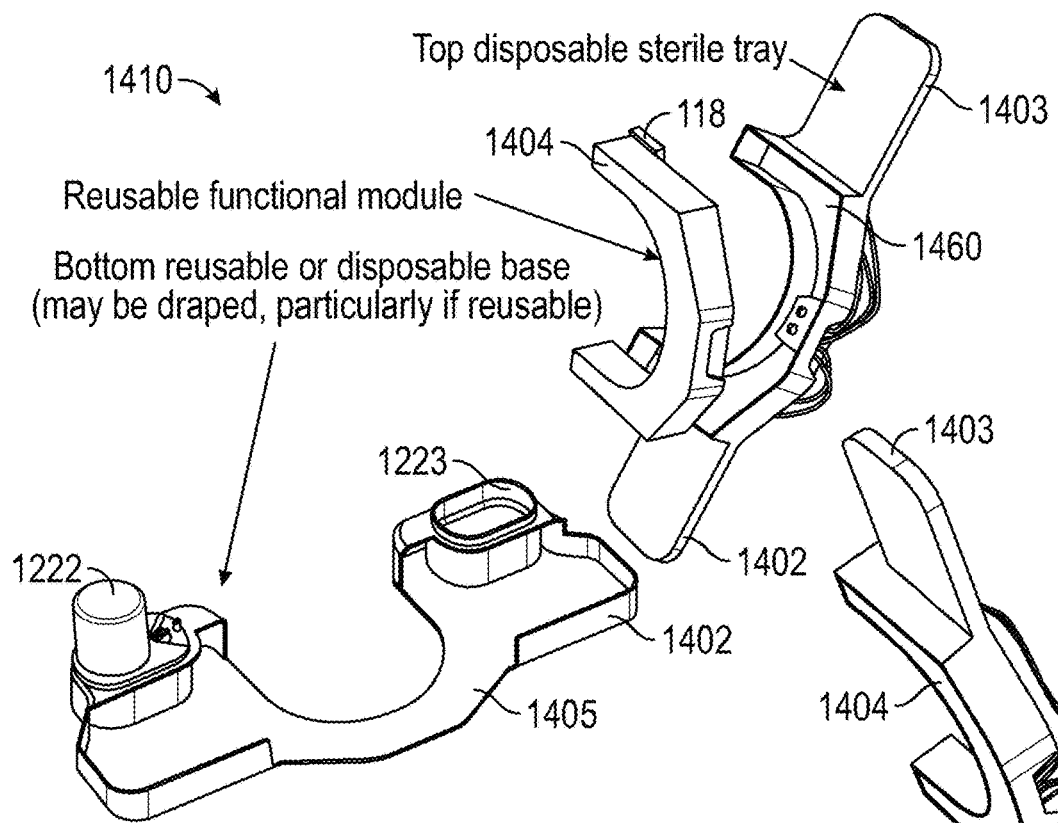
FIGS. 14A-14C illustrate another embodiment of a surgical tray system that isolates a non-sterile reusable component from a sterile surgical field.
Figure 14B:
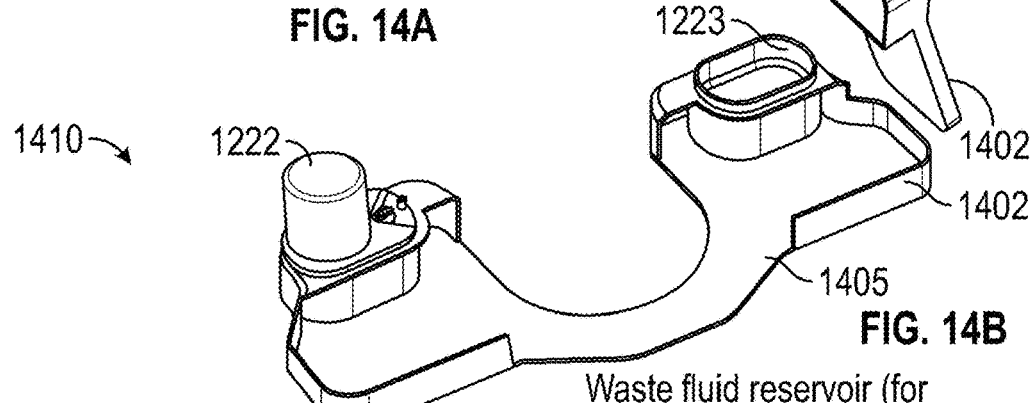
Figure 14C:
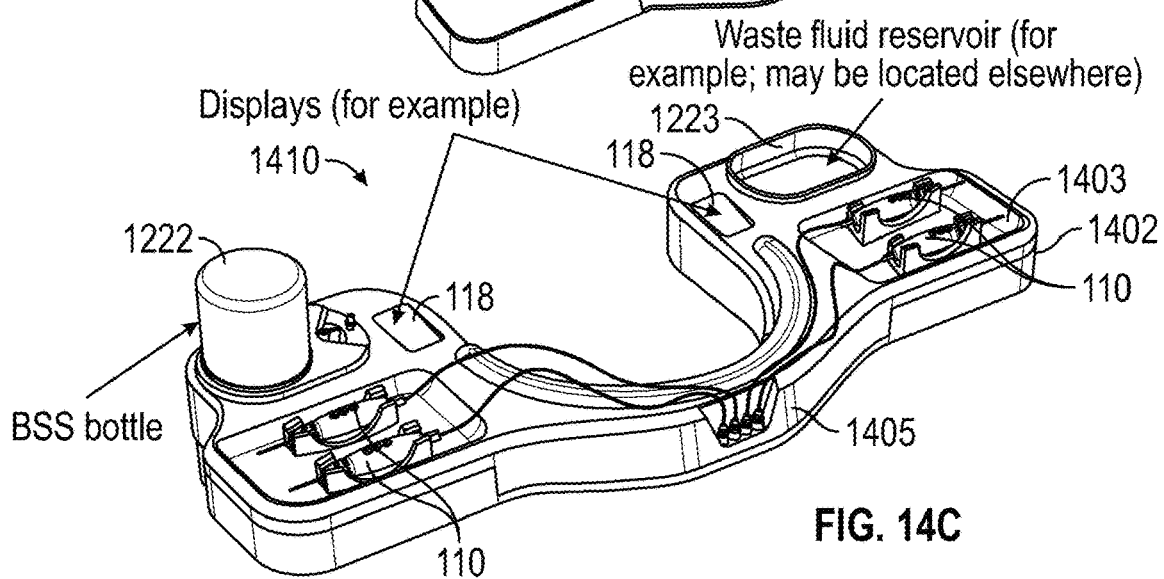

FIGS. 14A-14C illustrate another embodiment of a surgical tray or apparatus 1410 comprising a hollow shell forming at least part of an aseptic cavity or container 1460 for insertion therein of a reusable portion 1404. The surgical tray 1410 is similar to the surgical trays 1210 and 1310 described above. Surgical tray 1410, however, enables access to the cavity 1460 by detaching or removing a top portion or lid 1403 from a base or bottom portion 1405. In some embodiments, the base or bottom portion 1405 can be configured to be reusable and/or non-sterile, in which case the base or bottom portion 1405 may be draped. In some embodiments, the top portion 1403 and bottom portion 1405 together comprise a disposable portion 1402 of the surgical tray 1410. In some embodiments, more or less components may comprise the disposable portion 1402. For example, the disposable portion 1402 may further comprise the infusion and/or reservoir modules 1222, 1223. In some embodiments, the disposable portion 1402 comprises the lid or top portion 1403, but not the base 1405. Note that the embodiment shown in FIGS. 14A-14C is only an example of such a hollow shell embodiment. In this embodiment, the top tray 1403 is a shell, with the reusable module 1404 placed in the underside. When the top tray 1403 is mounted to the base portion 1405, mounting bracket, bed/chair, and/or armrest, the non-sterile reusable portion 1404 is effectively isolated from the patient and surgeon to provide a sterile barrier. Electrical, mechanical, optical, and/or fluidic connections are configured to be made between the reusable 1402 and single-use 1404 portions when the reusable portion 1404 is inserted into the single use portion 1402. In this embodiment, the bottom 1405 may be reusable (in some embodiments providing either only structural support or possibly including functional elements including but not limited to one or more power supplies, batteries, light sources, pumps, compressors, and/or the like) or it may be a separate disposable item. The bottom 1405 may be draped with a standard drape or a custom drape to provide a sterile barrier, particularly if it is a reusable component and sterility cannot be ensured for each surgical procedure. In various embodiments, the functionality may all be integrated into a single reusable functional module or it may be separated into multiple functional modules.

Additional Modular Surgical Tray Embodiments

Figure 15:
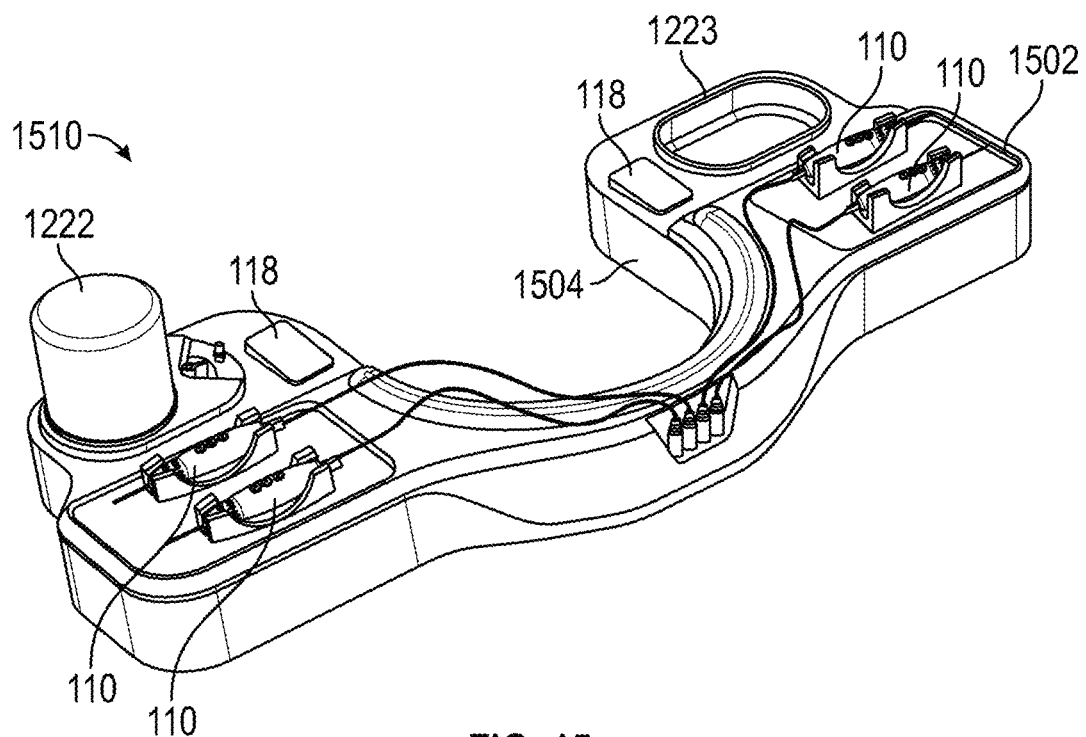
FIG. 15 illustrates another embodiment of a modular surgical tray system.

FIG. 15 illustrates another embodiment of a modular surgical tray or apparatus 1510. The surgical tray 1510 comprises a disposable portion 1502 and a reusable base portion 1504. The surgical tray 1510 further comprises aspiration and infusion modules 1223, 1222. FIG. 15 illustrates another example of having one or more disposable components that are separate from reusable aspects of the system. The reusable portions (in this embodiment, the base 1504, which comprises displays 118) may be draped with a sterile drape or they may be otherwise covered to maintain a sterile barrier, for example by a thin vacuum formed or molded plastic shell that may be integrated with some or all of the disposable portions 1502, 1222, 1223 or provided as a separate component. In some embodiments, disposable portion 1502 may be used to refer to just the handpieces unit, as shown in FIG. 15. In some embodiments, however, all disposable components or modules of the surgical tray 1510 may be collectively referred to as the disposable portion (for example, the unit 1502, the infusion module 1222, and the aspiration module 1223).

Figure 16A:
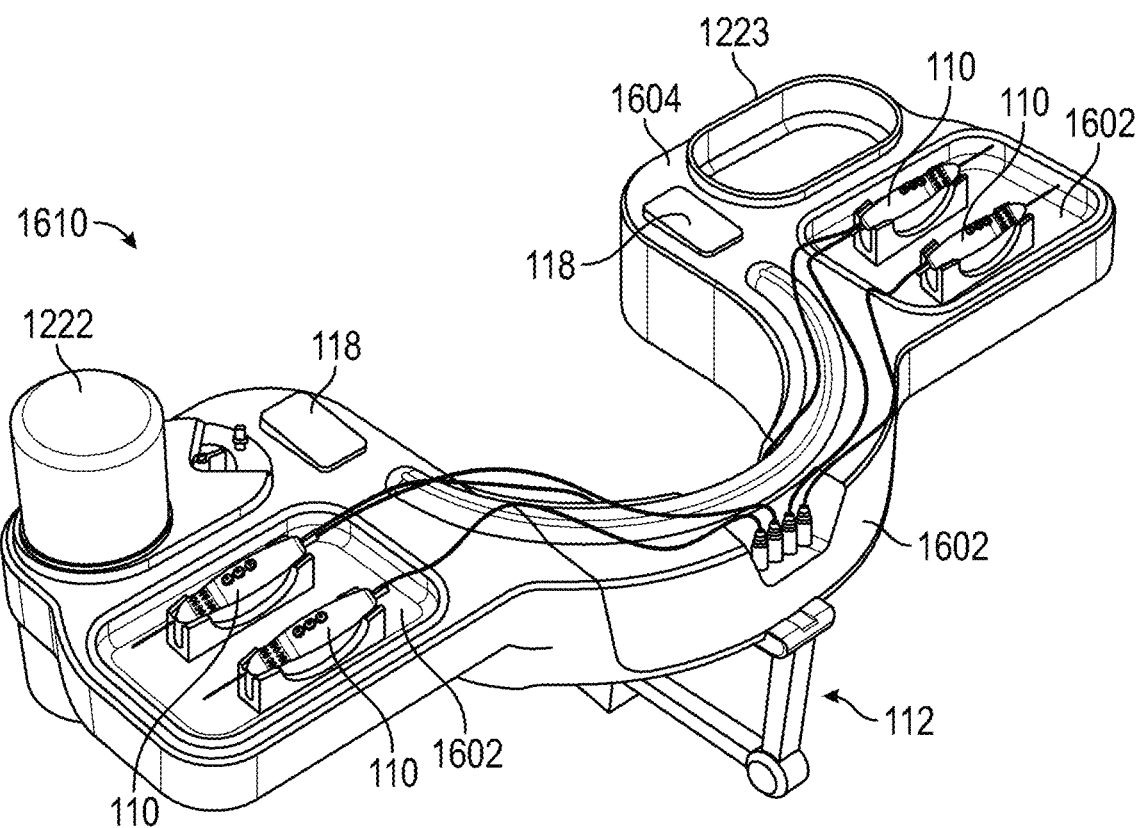
FIGS. 16A and 16B illustrates another embodiment of a modular surgical tray system.
Figure 16B:
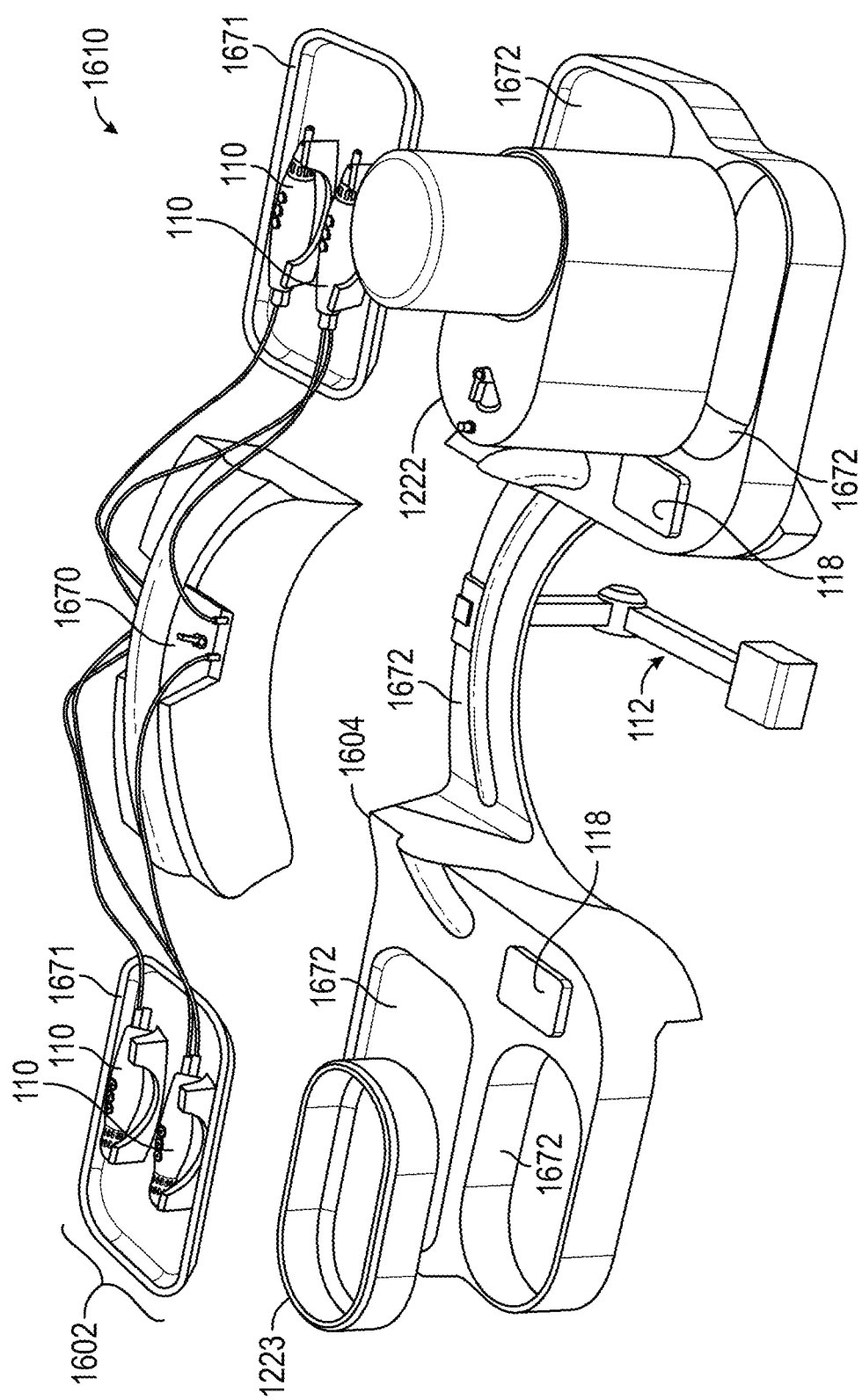

FIGS. 16A and 16B illustrate another embodiment of a modular surgical tray or apparatus 1610. This embodiment is similar to the tray 1510 illustrated in FIG. 15. In FIGS. 16A and 16B, however, the disposable handpieces unit 1602 is divided into three separate components: a central module 1670, and two outer trays 1671. Each disposable component of the surgical tray 1610 (for example, central module 1670, outer trays 1671, aspiration module 1223, and/or infusion module 1222) is configured to mate or couple with a different receiving or coupling feature 1672 of the reusable portion 1604. The base 1604 may be draped or otherwise covered with a sterile barrier if desired. In some embodiments, all disposable functional components may be primarily contained in a single functional module, but in other embodiments, such as shown in FIGS. 16A and 16B, the functional components may be distributed across multiple modules.

Aseptic BSS Bottle Holder

Figures 17A, 17B:
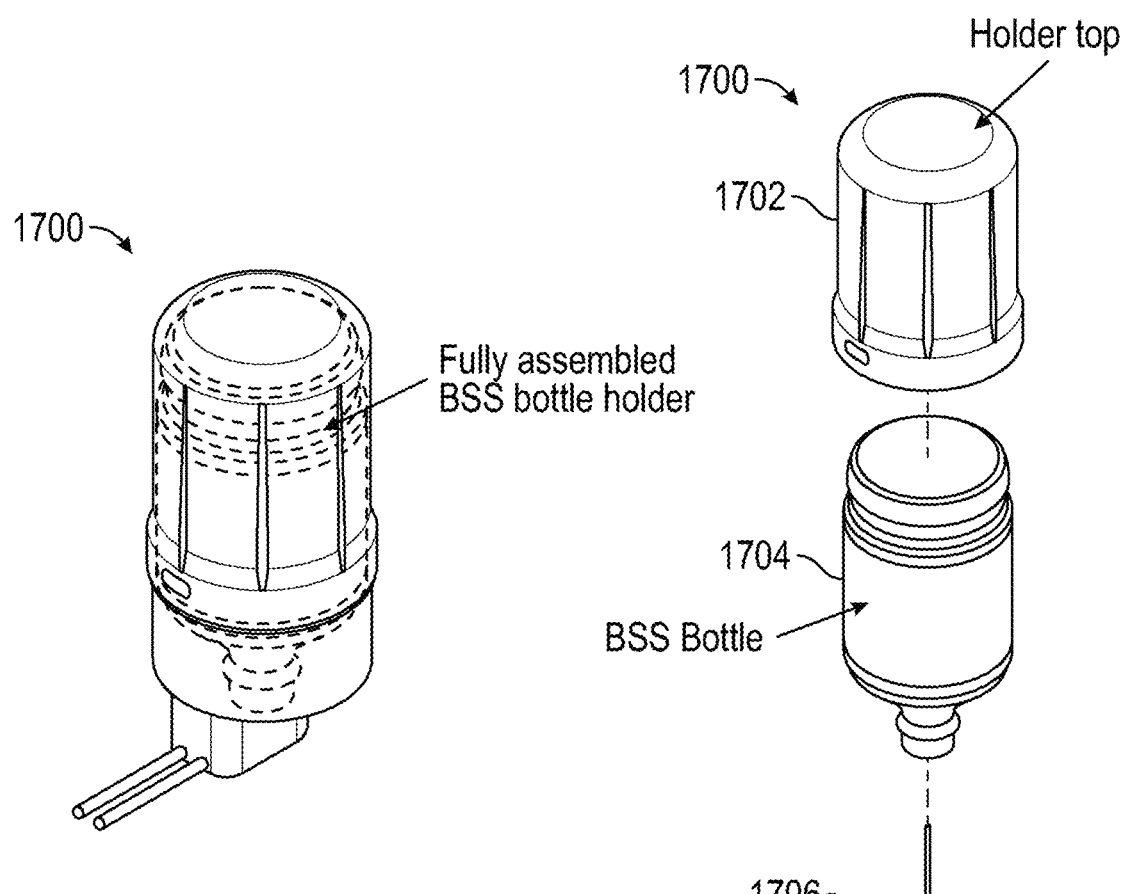
FIGS. 17A-17C illustrate an embodiment of a bottle holder that isolates a non-sterile BSS bottle from a sterile surgical field.
Figure 17C:
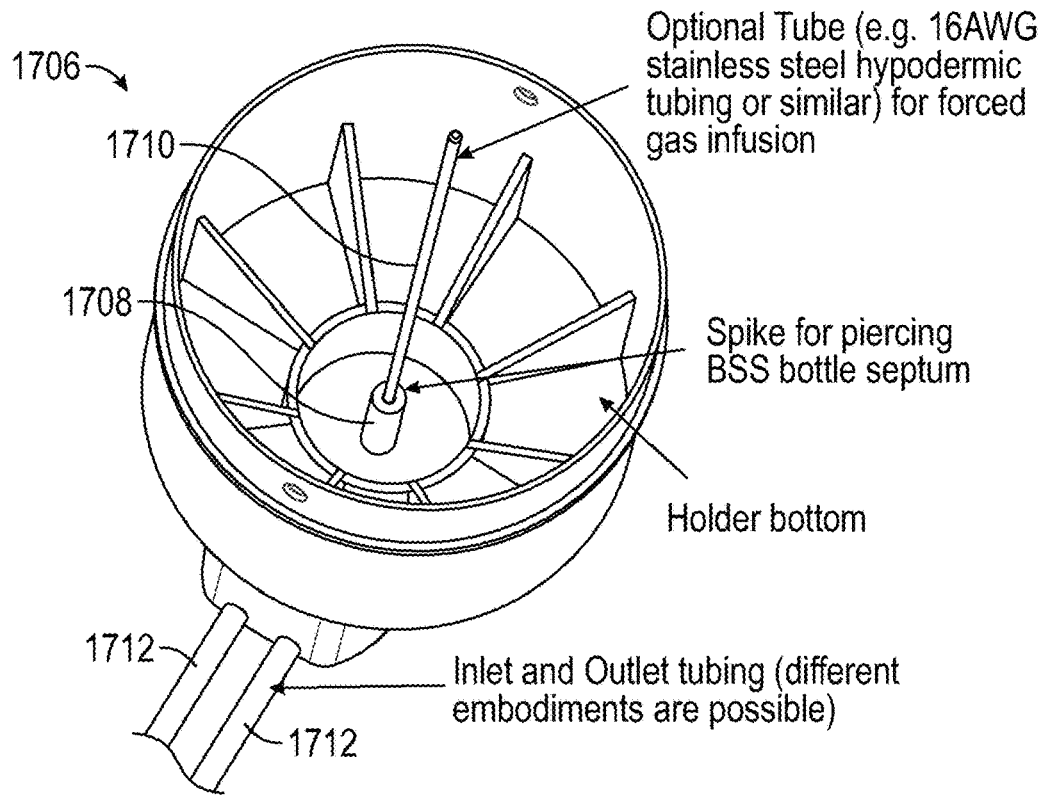

Some embodiments of surgical systems disclosed herein comprise an aseptic transfer enclosure as applied to a BSS bottle or other infusion source that is utilized in many surgeries. One example is shown in FIGS. 17A-17C, where a non-sterile BSS bottle 1704 is enclosed within a sterile BSS holder 1700 with a bottle spike 1708 located within the sterile work area. Such an embodiment allows a non-sterile BSS bottle to be brought into the sterile field, which may provide superior performance over current solutions, because of the reduced length of fluidic tubing between the infusion source (BSS bottle) and surgical site.

FIG. 17A illustrates the assembled BSS bottle holder 1700. FIG. 17B illustrates an exploded view of the BSS bottle holder 1700, comprising a top or cover 1702, a BSS bottle 1704, and a base or bottom 1706. In this embodiment, the cover 1702 comprises a mechanic twist lock feature to attach the cover 1702 to the base 1706. In other embodiments, however, various other locking or coupling mechanisms may be used. FIG. 17C illustrates more details of the base 1706, including inlet and outlet tubing 1712, a spike 1708 for piercing the BSS bottle 1704, and an optional tube 1710 for forced gas infusion. In some embodiments, the tube 1710 may comprise a tube that extends within the BSS bottle to an area above the fluid level of the BSS bottle. The tube 1710 may be used to introduce or remove gas to or from an interior of the BSS bottle, to change a pressure within the BSS bottle, enabling controlled infusion. The tube 1710 may in some embodiments comprise a medical-grade material, such as, for example, 16AWG stainless steel hypodermic tubing.

The example embodiment of FIGS. 17A-17C demonstrates the use of an aseptic container to house the non-sterile BSS bottle and provide a sterile barrier so that the BSS bottle can be located within the sterile field and in close proximity to the surgical site. Placing the BSS bottle closer to the patient and/or closer to the pumping source can allow for better and more precise fluidic management.

Peristaltic Pump

Peristaltic pumps may be utilized in various surgical procedures for pumping of fluids. In some embodiments, a peristaltic pump is configured or designed to accommodate gas sterilization such as ethylene oxide sterilization. In order to allow the gas to enter and escape from the tubing used in a peristaltic pump, it is desirable to avoid multiple occluding "pinch-points" that effectively trap a section or portion of the tubing such that there is no ingress or egress path for the gas to flow in or out. This for example may occur with a peristaltic pump with 3 or more rollers that are pinching the tubing in more than one location. Embodiments disclosed herein comprise a peristaltic pump or pump head with a roller or rollers (or components that perform the same purpose as the roller or rollers) that are configured to enable the pump to comprise a sterilization position or configuration, wherein a maximum of one pinch-point is created (or zero pinch points in some embodiments), enabling gas sterilization to occur without any "trapped" sections of tubing. The pump may also comprise a pumping or operational position or configuration, preferably to be utilized after sterilization has occurred, wherein more than one simultaneous pinch-points may be created while the pump is being used to pump fluids. For example, some embodiments comprise two rollers or a single roller (or components that perform the same purpose as the roller or rollers) such that a maximum of one part of the tubing is pinched at any given time in the sterilization configuration. Some embodiments may comprise even more than two rollers, as long as the pump is configurable such that no more than one part of the tubing is pinched in at least one configuration (for example, the sterilization configuration). The pump design may include keyways and/or other features that ensure proper alignment during assembly such that only a single roller is engaged with the tubing in the sterilization configuration. See FIG. 18 for an example that comprises two rollers 1806 that are capable of pinching the tubing 1808 simultaneously in two locations, but the rollers 1806 are arranged such that, if the rotor 1804 is in a particular position (for example, the position in which the rotor 1804 is shown in FIG. 18), only one pinch point will be created. Accordingly, such a pump could be configured to use the position or configuration illustrated in FIG. 18 as a "home," starting, or sterilization position, enabling gas sterilization prior to use in surgery.

With further reference to FIG. 18, FIG. 18 is a top view of a 2-roller peristaltic pump 1800 (or a pump head portion of a pump) showing in this configuration a single pinch point 1810 (at 12 o'clock in this figure). The bottom roller 1806 (at 6 o'clock) does not pinch the tubing 1808 in this orientation, allowing sterilization gas (for example, ethylene oxide) to enter and exit both ends of the tubing 1808 during the manufacturing process. When the pump 1800 is activated, the rotor 1804 and rollers 1806 will rotate clockwise or counter-clockwise providing a peristaltic pumping action (during which more than one pinch point will be created). In some embodiments, the pump components may contain keyed areas or other features to ensure proper alignment during assembly such that only a single roller is pinching the tubing.

In some embodiments, a peristaltic pump may enable gas sterilization in other ways. For example, a pump may include an expanding iris or aperture type configuration whereby prior to initial use or activation the rollers are disengaged along a smaller or greater diameter than the tubing itself (and therefore not pinching the tubing), and upon activating the motor the rollers engage along substantially the same radius as the tubing to provide a peristaltic pumping action.

Figure 19B:
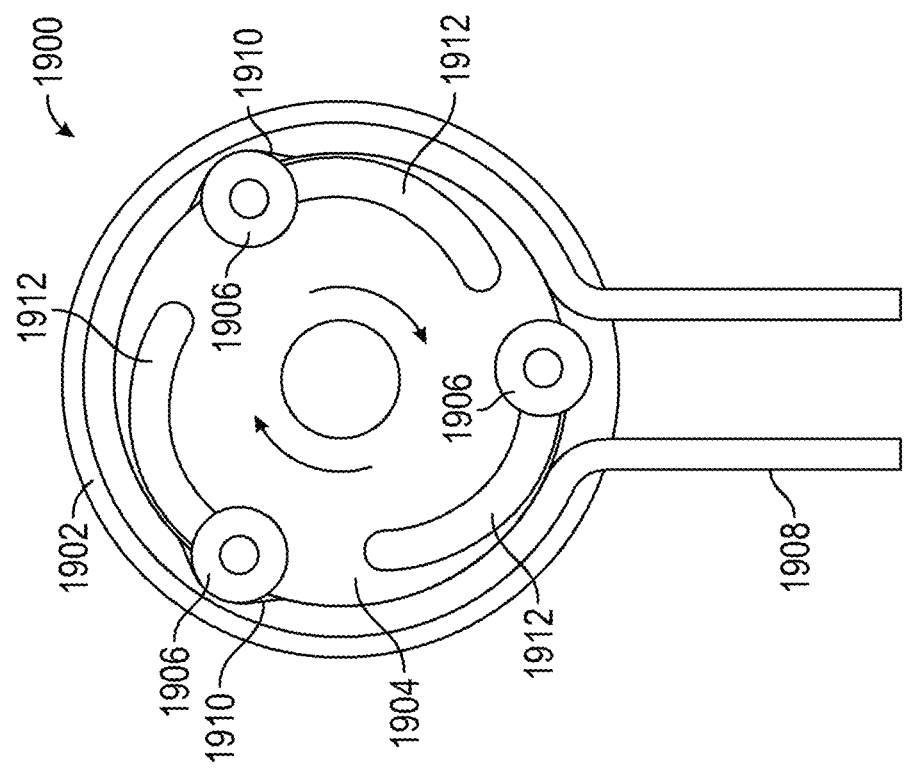
FIGS. 19A and 19B illustrate another embodiment of a peristaltic pump head configured to accommodate gas sterilization.
Figure 19A:
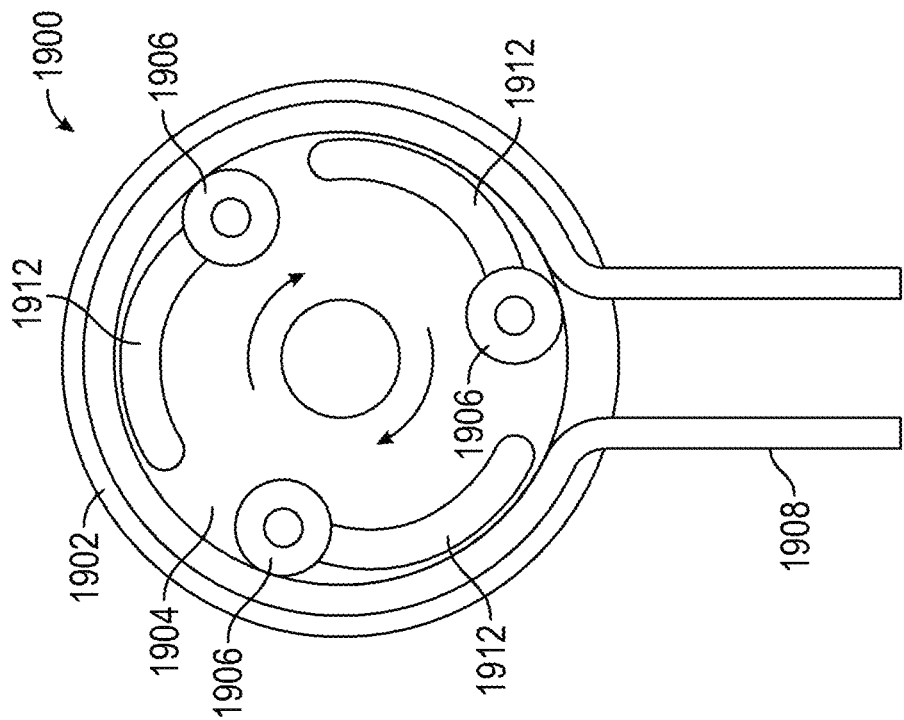

FIGS. 19A and 19B illustrate another embodiment of a peristaltic pump or pump head 1900 configured to enable efficient gas sterilization. Similar to the embodiment illustrated in FIG. 18, the peristaltic pumps 1900 comprises a sterilization configuration, wherein the tubing 1908 comprises no trapped pockets of air, and an operating configuration, wherein multiple pinch-points 1910 may be created. FIG. 19A illustrates the peristaltic pump 1900 in the sterilization configuration. In this embodiment, there are zero pinch-points in the sterilization configuration. In other embodiments, however, similar to as shown in FIG. 18, one pinch point may be utilized in the sterilization configuration. FIG. 19B illustrates the peristaltic pump 1900 in the operating configuration. In this figure, two simultaneous pinch-points 1910 are being created. Depending on the position of the rotor 1904, however, all three rollers 1906 may generate pinch-points 1910 simultaneously.

The peristaltic pump 1900 comprises a housing 1902, a rotor 1904 rotatably coupled to the housing 1902, and a plurality of rollers 1906, in this case three rollers. The peristaltic pump 1900 further comprises peristaltic tubing 1908 positioned around the rotor 1904 and positioned to be engageable by the rollers 1906 to enable fluid to be pumped within the tubing 1908. In the embodiment illustrated in FIGS. 19A and 19B, the rotor 1904 further comprises a channel 1912 (e.g., keyway, slot, guide, and/or the like) for each of the rollers 1906. The channels 1912 extend about the rotor 1904 in a curved fashion, wherein the channel 1912 is further from a central axis of the rotor 1904 at one end and closer to the central axis of the rotor 1904 at another end. Such a design can enable the rollers 1906 to be repositioned within the channel 1912 such that, at one end of the channel, as shown in FIG. 19A, no pinch-point is created between the roller 1906 and the tubing 1908. However, when the roller 1906 is at the other end of the channel, as illustrated in FIG. 19B, the roller 1906 is further away from the central axis of the rotor 1904 (and closer to the tubing 1908), creating an interference fit or pinch-point 1910 between the tubing 1908 and the roller 1906.

In some embodiments, the peristaltic pump 1900 illustrated in FIGS. 19A and 19B can be configured to automatically engage and/or disengage the rollers 1906. For example, the orientation of the channels 1912 can be such that a clockwise rotation of the rotor 1904 automatically results in the rollers 1906 moving counterclockwise with respect to the rotor 1904, and thus engaging the tubing 1908. Similarly, a counterclockwise rotation of the rotor 1904 can enable the rollers 1906 to automatically move within the channels 1912 in a clockwise direction with respect to the rotor 1904, thus automatically disengaging the tubing 1908 to enable gas sterilization. In some embodiments, the peristaltic pump 1900 may comprise springs or other mechanisms that bias the rollers 1906 toward one end of the channels 1912. For example, the peristaltic pump 1900 may comprise a spring that biases the rollers 1906 into the disengaged position, shown in FIG. 19A, to ensure that gas sterilization can occur with a pump that has not yet been activated or connected to a power source. As another example, the peristaltic pump 1900 may comprise a spring that biases the rollers 1906 into the engaged position, shown in FIG. 19B, to ensure that the rollers 1906 remain engaged with the tubing 1908 during operation. In some embodiments, instead of springs, or in addition to springs, a locking mechanism may be utilized that locks the rollers 1906 into position at either end of the channels 1912, to ensure the pump 1900 remains in either of the sterilization or operating configurations. In some embodiments, the face of the rotor 1904 may comprise a cam disk that comprises the channels 1912. The cam disk can be rotated with respect to the rest of the rotor to enable the rollers 1906 to move inwardly and outwardly.

The peristaltic pump 1900 illustrated in FIGS. 19A and 19B depicts one example embodiment of a peristaltic pump that comprises rollers selectively engageable with peristaltic tubing. One of skill in the art will recognize that various other designs may be utilized to perform such an action. For example, a peristaltic pump may comprise channels or keyways that enable a roller to move directly inward and outward with respect to the tubing 1908 (for example, in a direction perpendicular to a tangent of the tubing at the point where the roller would pinch the tubing). In such an embodiment, the rollers may be configured to move inwardly and outwardly by, for example, a cam mechanism that selectively engages the rollers with the tubing. In another embodiment, rollers may be mounted to pivoting and/or spring-loaded arms that may be moved inwardly or outwardly to selectively engage the rollers with the tubing.

Anterior Chamber Surgical System

In an embodiment, the surgical systems illustrated herein can be configured for anterior chamber surgical procedures, for example lens or cataract removal (commonly known as phacoemulsification or phacomorcellation). The surgical system can include one or more of the following: a handpiece, a console, a surgical tray, a display, a foot pedal.

Handpiece

In an embodiment, the system includes a handpiece held by the surgeon, the distal end of which is inserted into the anterior chamber of the eye through a small incision. The distal tip of the handpiece can be inserted into the eye and can be, for example, a hypodermic needle, tube, cannula, or trocar of size 17, 18, 19, 20, 21, 22, 23, 24, 25, 26, or 27 gauge, or in some cases larger or smaller gauge and made of any of a variety of materials, including stainless steel, titanium, plastic, polyimide, or the like.

In an embodiment, one function of the distal tip that is inserted into the eye is to break up, emulsify, and/or morcellate the cataract or lens, through ultrasonic vibrations, mechanical cutting and/or agitation, ablation, laser, and/or other techniques. In an embodiment, the system can include a hollow channel inside the probe tip for the aspiration or infusion of fluids and tissues. In an embodiment, the system can include a separate hollow channel for infusion and aspiration that is located adjacent to or positioned near the probe tip that breaks up the cataract or lens.

In an embodiment, the system can include mechanisms for vibrating, oscillating, reciprocating, rotating, cantilevering, and/or otherwise translating the position of the needle in one or more axes, for example, at a frequency in the kilohertz or higher range. This motion can be generated through the use of piezoelectric materials (such as Lead-Zirconate-Titanate, aka PZT or a commonly available piezo bender element) that vibrate when driven by a time varying voltage signal; it can be generated through the use of electromagnetics, for example in a voice-coil actuator, solenoid, or motor configuration; it can be generated through pneumatics or hydraulics; it can be generated through transmission drive systems, such as a rotating or reciprocating cable, drive belt, geared transmission, or push-pull mechanism.

In an embodiment, the system can comprise mechanisms for mechanically cutting or agitating a tissue sample (e.g. lens, cataract). This can include a guillotine or rotating (360 degrees or a portion thereof, for example 180 degrees reciprocating) cutting mechanism such as those used for vitreous removal or tissue debridement. Other mechanisms can include a rotating or otherwise moving/translating a whisk or whisks at the distal end of the probe that break up the tissue of interest through the mechanical movement of the whisk.

In an embodiment, the system can be configured to utilize a monochromatic or narrow-band light source (for example, laser or LED or the like) or a broadband light source to prepare the cataract, lens, or other tissue of interest for removal via photochemical, photomechanical, and/or photothermal means. The light source may be located in the handpiece itself or located elsewhere (for example, in the console or tray) and optically routed to the handpiece via a single mode or multi-mode fiber or fiber bundle (as previously described).

In an embodiment, the system can be configured to utilize heat or RF energy to cauterize or ablate tissue of interest (including but not limited to cataracts and lens material).

In an embodiment, a second function of the distal tip of the handpiece that is inserted into the eye can be to aspirate tissue and fluid, including the lens and cataract fragments generated by the action of the probe tip. The probe tip can be connected to a pump system that creates vacuum pressure at the needle tip to aspirate fragments smaller than the inner diameter of the needle tip and to hold fragments larger than the inner diameter until they are emulsified, morcellated, or broken up by the action of the needle tip to a size small enough for aspiration. The aspiration can be provided by a pump or other means as described earlier. In an embodiment, the locate the aspiration mechanism (pump or otherwise) can be in a console or tray separate from the handpiece and tethered to the handpiece via tubing suitable for the aspiration of fluids, for example flexible vinyl or PVC tubing. The close proximity of the tray reduces the length requirements of the tubing set, improving the performance and responsiveness of the aspiration. In an embodiment, the locate the aspiration mechanism (pump or otherwise) can be inside the handpiece or adjacent to the handpiece. This can be advantageous because such a design reduces the path length of the aspirated fluid, thereby reducing the requirements of the aspiration mechanism and eliminating long tubing sets that slow the response time (for example, when the surgeon changes the rate of aspiration) and can entangle the surgeon and assistants in the operating room.

Embodiments of the invention incorporate a pressure sensor in the distal tip of the handpiece as previously described, wherein the pressure sensor readings are used to control the rate of infusion (and/or aspiration) during a procedure. The control can be in the form of a feedback control loop (e.g. proportional-integral-derivative aka PID, a subset thereof, or similar). A simpler embodiment displays the pressure information to the surgeon, who can then manually control the rate of infusion. The system can alert the surgeon when the pressure falls outside of a preset range of pressures.

In an embodiment, the system can be configured to include some or all of the required functionality for anterior segment procedures, and in particular lens and cataract removal, in a single handpiece. The handpiece can include a mechanism for emulsification or morcellation (using one or more of the mechanisms previously described above). The handpiece can also comprise a mechanism for aspiration (such as a pump or one or more of the mechanisms previously described). The handpiece may include a mechanism for providing infusion into the eye (including any of the means previously described), or the infusion may be provided by a separate infusion cannula and infusion fluid source and controlled/driven by the handpiece or a separate nearby tray or console.

In the self-contained embodiments, the handpiece can include a reservoir that contains the infusion solution(s) (including BSS, viscoelastics, silicone oil, or the like) used during the procedure. The handpiece can also include a reservoir for the aspirated waste. The infusion and aspiration reservoirs can be contained within or fully integrated into the handpiece or they may be located directly adjacent to it (for example, a bag or bottle hanging from the handpiece or secured to the surgeon's hand, wrist, or arm). The reservoirs can also be located in, mounted on, or hanging from a nearby tray, surgeon arm support or patient headrest, or from the microscope.

In an embodiment, the system can be configured to use of a filter (for example, a porous membrane filter) in-line with the aspiration and infusions systems so that the aspirated fluid can be filtered and re-infused, significantly reducing the amount of required infusion solution and decreasing the size and weight requirements of a handheld system. The filter (and aspiration pump) can be located in the handpiece, or in some embodiments one or both may be located in a separate nearby tray or console with a short tubing set connecting the handpiece to the filter and/or pump. The filtered system can also be used for posterior segment and vitreo-retinal procedures.

In an embodiment, the self-contained handpiece can comprise the integrated pressure sensor previously described above, either in the distal tip of the needle or along the fluid path, utilized in a feedback control loop to control the rate of infusion (and/or aspiration).

In an embodiment, the system can be configured to be used with valved cannula(s) and/or valved trocar(s) to reduce leakage of infused fluid from the anterior chamber. These devices are commonly used in vitreoretinal surgery and orthopedic surgery but not typically in anterior segment procedures. However, incorporating them into the anterior procedure will reduce the required volume of infusion fluids, resulting in a smaller, lighter, and more compact system.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

What is claimed is:

1. A surgical apparatus for use by a surgeon during a surgical procedure, the surgical apparatus comprising:
one or more sealed sterilized surgical packs configured to be unsealed before a surgical procedure, the one or more sealed sterilized surgical packs comprising one of each of a removably receivable sterile infusion module and a removably receivable sterile aspiration module, the sterile infusion and aspiration modules each comprising:
a housing comprising walls, a top surface, and a bottom surface sized and configured to be removably received in a sterile module recess of a reusable support structure, and at least one outer surface configured to be part of the sterile field of the surgical procedure;
a pump for pumping fluids into or out of a surgical site; and
a motor coupled to the pump for rotating a rotor of the pump,
wherein the housing further comprises an electrical interface configured to receive electrical power from the reusable support structure for powering the motor,
wherein the sterile infusion module is configured to pump fluids into the surgical site, and the sterile aspiration module is configured to pump fluids out of the surgical site;

wherein the one or more sealed sterilized surgical packs further comprises:
a sterile surgical instrument; and
a sterile surgical instrument holder comprising a top surface configured to be part of the sterile field of the surgical procedure, the top surface comprising a receiving portion for positioning therein or thereon of the sterile surgical instrument, the sterile surgical instrument holder further comprising a bottom surface sized and configured to be received in an instrument holder recess of the reusable support structure;
wherein the sterile surgical instrument is configured to couple with one or more of: a light source of the reusable support structure, an electronic controller of the reusable support structure, a mechanical driver of the reusable support structure, a pneumatic driver of the reusable support structure, and a fluidic driver of the reusable support structure;
wherein the reusable support structure is non-sterile, and the one or more sealed sterilized surgical packs further comprises a surgical drape configured to be positioned between the non-sterile reusable support structure and at least one of the modules.

2. The surgical apparatus of claim 1, wherein the pump comprises a sterilization configuration wherein at most one pinch-point is created in peristaltic tubing of the pump.

3. The surgical apparatus of claim 1, wherein the sterile surgical instrument holder comprises at least two pieces selectively coupleable together to form a reusable non-sterile recess that encapsulates a reusable non-sterile module.

4. The surgical apparatus of claim 1, wherein the sterile surgical instrument holder comprises a hinged opening for access to the reusable non-sterile recess.

5. The surgical apparatus of claim 1, wherein the sterile surgical instrument holder comprises a drawer for access to the reusable non-sterile recess.

* * * * *